(12) United States Patent
Futerman et al.

(10) Patent No.: US 7,855,063 B2
(45) Date of Patent: Dec. 21, 2010

(54) PARTIALLY DEGLYCOSYLATED GLUCOCEREBROSIDASE POLYPEPTIDE AND CRYSTALS THEREOF

(75) Inventors: Anthony Futerman, Rehovot (IL); Joel L. Sussman, Rehovot (IL); Israel Silman, Rehovot (IL); Michal Harel, Rehovot (IL); Hay Dvir, San Diego, CA (US); Lilly Toker, Rehovot (IL)

(73) Assignee: Yeda Research And Development Co. Ltd., Rehovot (IL)

( * ) Notice: Subject to any disclaimer, the term of this patent is extended or adjusted under 35 U.S.C. 154(b) by 258 days.

(21) Appl. No.: 10/552,287

(22) PCT Filed: Apr. 18, 2004

(86) PCT No.: PCT/IL2004/000335

§ 371 (c)(1), (2), (4) Date: Jan. 4, 2007

(87) PCT Pub. No.: WO2004/091475

PCT Pub. Date: Oct. 28, 2004

(65) Prior Publication Data

US 2007/0166813 A1     Jul. 19, 2007

(30) Foreign Application Priority Data

Jun. 2, 2003    (IL) ..................................... 156273

(51) Int. Cl.
    *C12N 9/26*     (2006.01)
    *A61K 38/47*     (2006.01)

(52) U.S. Cl. .................................... 435/201; 424/94.61

(58) Field of Classification Search .................. None
See application file for complete search history.

(56) References Cited

U.S. PATENT DOCUMENTS

| 5,236,838 | A | | 8/1993 | Rasmussen et al. |
| 5,879,680 | A | | 3/1999 | Ginns et al. |
| 7,442,537 | B1 | * | 10/2008 | Benson et al. ............... 435/219 |
| 2007/0038380 | A1 | * | 2/2007 | Somers et al. ................ 702/19 |

FOREIGN PATENT DOCUMENTS

| WO | WO 01/77307 | 10/2001 |
| WO | WO 2004/091475 | 10/2004 |

OTHER PUBLICATIONS

Dvir et al., "X-ray structure of human acid-beta-glucosidase, the defective enzyme in Gaucher disease", EMBO Reports 4:704-709, 2003.*
Branden et al., "Introduction to Protein Structure Second Edition", Garland Publishing Inc., New York, 1999, pp. 374-375.*
Drenth et al., "Principles of X-ray Crystallography," Springer, New York, 1999, p. 1.*
Kierzek et al., "Models of protein crystal growth", Biophys Chem 91:1-20, 2001.*
Wiencek, "New Strategies for Protein Crystal Growth", Ann Rev Biomed Eng 1:505-534, 1999.*
Buts et al.,"Impact of natural variation in bacterial F17G adhesins on crystallization behaviour", Acta Cryst D61:1149-1159, 2005.*
Skarzynski et al., "Industrial perspective on X-ray data collection and analysis", Acta Cryst D62:102-107, 2006.*
Kundrot et al., "Which strategy for a protein crystallization project?", Cell. Mol. Life Sci. 2004, 61: 525-536.*
Weber, "Overview of Protein Crystallization Methods", Methods in Enzymology, 1997, vol. 276, pp. 13-22.*
Cudney, "Protein Crytallization and Dumb Luck", Rigaku Journal, 1999, vol. 16, No. 1, pp. 1-7.*
Cudney, "Protein Crytallization and Dumb Luck", Rigaku Journal, 1999, vol. 16, No. 1, pp. 1-7.*
McPherson et al., "Current approaches to macromolecular crytallization", Eur. J. Biochem. 189:1-23, 1990.*
Tonetti et al., Acta Crystallogr D Biol Crystallogr 54:684-687, Jul. 1998.*
Hogg et al., Acta Cryst. (2002). D58, 1734-1739, 2002.*
Kalisz et al., J. Mol. Biol. 213:207, 209, 1990.*
Tayebi et al., Mol. Genet. Metabol. 79:104-109, 2003.*
Grueninger-Leitch et al., Protein Science 5:2617-2622, 1996.*
Mills et al., Tetrahedron: Asymmetry 11:75-93, 2000.*
Blundell et al. "High-Throughput Crystallography for Lead Discovery in Drug Design", Nature Reviews: Drug Disvocery, 1(1): 45-54, 2002.

(Continued)

*Primary Examiner*—David J Steadman

(57) ABSTRACT

A method of identifying a compound capable of correcting an impaired enzymatic activity of a mutant glucocerebrosidase molecule, the method comprising: (a) obtaining a first set of structure coordinates, the first set of structure coordinates defining a 3D structure of a glucocerebrosidase molecule capable of displaying normal enzymatic activity or a portion thereof; (b) computationally generating using the first set of structure coordinates a second set of structure coordinates, the second set of structure coordinates defining a predicted 3D structure of the mutant glucocerebrosidase molecule or a portion thereof; and (c) computationally identifying, using the second set of structure coordinates, a compound capable of interacting with the mutant glucocerebrosidase molecule in such a way as to correct the impaired enzymatic activity thereof, thereby identifying the compound capable of correcting the impaired enzymatic activity of the mutant glucocerebrosidase molecule. A glucocerebrosidase preparation comprising a population of glucocerebrosidase molecules, wherein substantially each of said glucocerebrosidase molecules: (i) has an amino acid sequence at least 95 percent homologous to an amino acid sequence set forth by SEQ ID NO: 1 or 8; (ii) is glycosylated at, or has an aspartatic acid residue at, glycosylation residue 1 of said amino acid sequence; and (iii) is independently unglycosylated at one or more glycosylation residues selected from the group consisting of glycosylation residues 2, 3 and 4 of said amino acid sequence.

2 Claims, 12 Drawing Sheets

OTHER PUBLICATIONS

Brumshtein et al. "Structural Comparison of Differently Glycosylated Forms of Acid-β-Glucosidase, the Defective Enzyme in Gaucher Disease", Acta Crystallographica, Section D, Biological Crystallography, 62(Pt.12): 1458-1465, 2006.

Grabowski et al. "Enzyme Therapy for Gaucher Disease: The First 5 Years", Blood Reviews, 12(2): 115-133, 1998. p.118-119, 121-123, 127-131.

Rayon et al. "The Protein N-Glycosylation in Plants", Journal of Experimental Botany, 49(326): 1463-1472, 1998.

Zhao et al. "Gaucher Disease: Perspectives on A Prototype Lysosomal Disease", Cellular and Molecular Life Sciences, CMLS, 59(4): 694-707, 2002. Table 1, p. 698, 702, 704.

Grabowski et al. "Human Acid β-Glucosidase—Use of Conduritol B Epoxide Derivatives to Investigate the Catalytically Active Normal and Gaucher Disease Enzymes", The Journal of Biological Chemistry,261 (18): 8263-8269, 1986.

Berg-Fussman et al. "Human Acid β-Glucosidase—N. Glycosylation Site Occupancy and the Effect of Glycosylation on Enzymatic Activity", The Journal of Biological Chemistry, 268(20):14861-14866, 1993.

Roeber et al. "Crystallization and Preliminary X-Ray Analysis of Recombinant Human Acid Beta-Glucocerbrosidase, A Treatment for Gaucher's Disease", Biological Crystallography, D59: 343-344, 2003.

Sawkar et al. "Chemical Chaperones Increase the Cellular Activity of N370S β-Glucosidase:, A Therapeutic Strategy for Gaucher Disease", PNAS, 99(24): 15428-15433, 2002.

Erickson et al. "Biosynthesis of the Ltsomal Enzyme Glucocerebrosidase", The Journal of Biological Chemistry, 260(26): 14319-14324, 1985.

Ahn et al. "Crystal Structure of Saposin B Reveals A Dimeric Shell for Lipid Binding", Proc. Natl. Acad. Sci. USA, 100(1): 38-43, 2003.

Amaral et al. "Gaucher Disease: Expression and Characterization of Mild and Severe Acid β-Glucosidase Mutations in Portuguese Type 1 Patients", European Journal of Human Genetics, 8: 95-102, 2000.

Amaral et al. "Type 1 Gaucher Disease: Identification of N396T and Prevalence of Glucocerebrosidase Mutations in the Portuguese", Human Mutation, 8: 280-281, 1996.

Beutler "Economic Malpractice in the Treatment of Gaucher's Disease", The American Journal of Medicine, 97: 1-2, 1994.

Beutler et al. "Gaucher Disease", The Metabolic and Molecular Bases of Inherited Disease, Chap.146: 3635-3668, 2001.

Beutler et al. "Two New Gaucher Disease Mutations", Human Genetics, 93: 209-210, 1994.

Brünger et al. "Crystallography & NMR System: A New Software Suite for Macromolecular Structure Determination", Acta Crystallographica Section D, 54: 905-921, 1998.

Buccoliero et al. "The Role of Sphingolipids in Neural Development: Lessons From Models of Sphingolipid Storage Diseases", Neurochemical Research, 27(7/8): 565-574, 2002.

Charrow et al. "The Gaucher Registry. Demographics and Disease Characteristics of 1698 Patients With Gaucher Disease", Archive of Internal Medicine, 160: 2835-2843, 2000.

Chi et al. "Crystal Structure of the β-Glycosidase From the Hyperthermophile Thermosphaera Aggregans: Insights Into Its Activity and Thermostability", FEBS Letters, 445: 375-383, 1999.

Cox et al. "Novel Oral Treatment of Gaucher's Disease With N-Butyldeoxynojirimycin (OGT 918) to Decrease Substrate Biosynthesis", The Lancet, 355: 1481-1485, 2000.

Davies et al. "Structures and Mechanisms of Glycosyl Hydrolases", Structure, 3: 853-859, 1995.

Dinur et al. "Human Acid β-Glucosidase: Isolation and Amino Acid Sequence of A Peptide Containing the Catalytic Site", Proc. Natl. Acad. Sci. USA, 83: 1660-1664, 1986.

Fabrega et al. "Human Glucocerebrosidase: Heterologous Expression of Active Site Mutants in Murine Null Cells", Glycobiology, 10(11): 1217-1224, 2000.

Fan "A Contradictory Treatment for Lysosomal Storage Disorders: Inhibitors Enhance Mutant Enzyme Acitivity", Trends in Pharmacological Sciences, 24(7): 355-360, 2003.

De La Fortelle et al. "Maximum-Likelihood Heavy-Atom Parameter Refinement for Multiple Isomorphous Replacement and Multiwavelength Anamalous Diffraction Methods", Methods in Enzymology, 276: 472-494, 1997.

Futerman et al. The Cell Biology of Lysosomal Storage Disorders, Nature Reviews in Molecular & Cellular Biology, 5: 554-565, 2004.

Futerman et al. "New Directions in the Treatment of Gaucher Disease", Trends in Pharmacological Sciences, 25(3): 147-151, 2004.

Grabowski et al. "Enzyme Therapy for Lysosomal Storage Disease: Principles, Practice, and Prospects", Annual Reviews in Genomics & Human Genetics, 4: 403-436, 2003.

Grabowski et al. "Enzyme Therapy in Type 1 Gaucher Disease: Comparative Efficacy of Mannose-Terminated Glucocerebrosidase From Natural and Recombinant Sources", Annals of Internal Medicine, 122(1): 33-39, 1995.

Grabowski et al. "Acid β-Glucosidase: Enzymology and Molecular Biology of Gaucher Disease", Critical Reviews in Biochemistry and Molecular Biology, 25(6): 385-414, 1990.

Grace et al. "Analysis of Human Acid β-Glucosidase by Site-Directed Mutagenesis and Heterologous Expression", The Journal of Biological Chemistry, 269(3): 2283-2291, 1994.

Henrissat et al. "New Families in the Classification of Glycosyl Hydrolases Based on Amino Acid Sequence Similarities", Biochemical Journal, 293: 781-788, 1993.

Henrissat et al. "Updating the Sequence-Based Classification of Glycosyl Hydrolases", Biochemical Journal, 316: 695-696, 1996.

Henrissat et al. "Conserved Catalytic Machinery and the Prediction of A Common Fold for Several Families of Glycosyl Hydrolases", Proc. Natl. Acad. Sci. USA, 92: 7090-7094, 1995.

Hrmova et al. "Catalytic Mechanisms and Reaction Intermediates Along the Hydrolytic Pathway of A Plant β-D-Glucan Glucohydrolase", Structure, 9: 1005-1016, 2001.

Jones "A Graphics Model Building and Refinement System for Macromolecules", Journal of Applied Crystallography, 11: 268-272, 1978.

Jones et al. "Improved Methods for Building Protein Models in Electron Density Maps and the Location of Errors in These Models", Acta Crystallographica Section A, 47: 110-119, 1991.

Korkotian et al. "Elevation of Intracellular Glucosylceramide Levels Results in An Increase in Endoplasmic Reticulum Density and in Functional Calcium Stores in Cultured Neurons", The Journal of Biological Chemistry, 274(31): 21673-21678, 1999.

Lachmann "Miglustat Oxford GlycoSciences/Actelion", Current Opinion in Investigational Drugs, 4(4): 472-479, 2003.

Legler "Glucosidases", Methods in Enzymology, 46(Chap.40): 368-381, 1977.

Legler "Glycoside Hydrolases: Mechanistic Information From Studies With Reversible and Irreversible Inhibitors", Advances in Carbohydrate Chemistry and Biochemistry, 48: 319-384, 1990.

Lloyd-Evans et al. "Glucosylceramide and Glucosylsphingosine Modulate Calcium Mobilization From Brain Microsomes Via Different Mechanisms", The Journal of Biological Chemistry, 278(26): 23594-23599, 2003.

Meivar-Levy et al. "Analysis of Glucocerebrosidase Activity Using N-(1-[14C]Hexanoyl)-D-Erythro-Glucosylsphingosine Demonstrates A Correlation Between Levels of Residual Enzyme Activity and the Type of Gaucher Disease", Biochemical Journal, 303: 377-382, 1994.

Miao et al. "Identification of Glu340 as the Active-Site Nucleophile in Human Glucocerebrosidase by Use of Electrospray Tandem Mass Spectrometry", The Journal of Biological Chemistry, 269(15): 10975-10978, 1994.

Mistry et al. "Therapeutic Delivery of Proteins to Macrophages: Implications for Treatment of Gaucher's Disease", The Lancet, 348: 1555-1559, 1996.

Morel et al. "Effect of Mutations Within the Peripheral Anionic Site on the Stability of Acetylcholinesterase", Molecular Pharmacology, 55: 982-992, 1999.

Murshudov et al. "Efficient Anisotropic Refinement of Macromolecular Structures Using FFT", Acta Crystallographica Section D, 55: 247-255, 1999.

Nyholm et al. "The Effect of Hydrogen Bonds on the Conformation of Clycosphingolipids. Methylated and Unmethylated Cerebroside Studied by X-Ray Single Crystal Analysis and Model Calculations", Chemistry and Physics of Lipids, 52: 1-10, 1990.

Otwinowski et al. "Processing of X-Ray Diffraction Data Collected in Oscillation Mode", Methods in Enzymology, 276(Chap.20): 307-326, 1997.

Perrakis et al. "Automated Protein Model Building Combined With Iterative Structure Refinement", Nature Structural Biology, 6(5): 458-463, 1999.

Qasba et al. "Substrate-Induced Conformational Changes in Glycosyltransferases", Trends in Biochemical Sciences, 30(1): 53-62, 2005.

Schüttelkopf et al. "PRODRG: A Tool for High-Throughput Crystallography of Protein-Ligand Complexes", Acta Crystallographica Section D, 60: 1355-1363, 2004.

Usón et al. "Advances in Direct Methods for Protein Crystallography", Current Opinion in Structural Biology, 9: 643-648, 1999.

Weinreb et al. "Effectiveness of Enzyme Replacement Therapy in 1028 Patients With Type 1 Gaucher Disease After 2 to 5 Years of Treatment: A Report From the Gaucher Registry", American Journal of Medicine, 113: 112-119, 2002.

Westhead et al. "Protein Structural Topology: Automated Analysis and Diagrammatic Representation", Protein Science, 8: 897-904, 1999.

Wilkening et al. "Lysosomal Degradation on Vesicular Membrane Surfaces", The Journal of Biological Chemistry, 273(46): 30271-30278, 1998.

Kabsch, "Automatic Processing of Rotation Diffraction Data From Crystals of Initially Unknown Symmetry and Cell Constants", Journal of Applied Crystallography, 26: 795-800, 1993.

International Preliminary Report on Patentability Dated Mar. 29, 2007 From the International Bureau of WIPO Re.: Application No. PCT/IL04/00335.

Office Action Dated Mar. 17, 2009 From the Israeli Patent Office Re.: Application No. 171186 and Its Translation Into English.

Official Action Dated Mar. 16, 2010 From the US Patent and Trademark Office Re.: U.S. Appl. No. 10/552,287.

Office Action Dated Mar. 16, 2010 From the Israeli Patent Office Re.: Application No. 171186 and Its Translation Into English.

Communication Pursuant to Article 94(3) EPC Dated May 25, 2010 From the European Patent Office Re.: Application No. 04728128.2.

* cited by examiner

Fig. 6b   Fig. 6c

SEQUENCE LISTING

<160> NUMBER OF SEQ ID NOS: 16

<210> SEQ ID NO 1
<211> LENGTH: 497
<212> TYPE: PRT
<213> ORGANISM: Homo sapiens

<400> SEQUENCE: 1

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220
```

```
Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
            245                 250                 255

Arg Asp Phe Ile Ala Arg Asp Leu Gly Pro Thr Leu Ala Asn Ser Thr
        260                 265                 270

His His Asn Val Arg Leu Leu Met Leu Asp Asp Gln Arg Leu Leu Leu
    275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
            325                 330                 335

Phe Ala Ser Glu Ala Cys Val Gly Ser Lys Phe Trp Glu Gln Ser Val
        340                 345                 350

Arg Leu Gly Ser Trp Asp Arg Gly Met Gln Tyr Ser His Ser Ile Ile
    355                 360                 365

Thr Asn Leu Leu Tyr His Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
            405                 410                 415

Phe Tyr His Leu Gly His Phe Ser Lys Phe Ile Pro Glu Gly Ser Gln
        420                 425                 430

Arg Val Gly Leu Val Ala Ser Gln Lys Asn Asp Leu Asp Ala Val Ala
    435                 440                 445

Leu Met Asn Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp His Arg
            485                 490                 495

Gln

<210> SEQ ID NO 2
<211> LENGTH: 497
<212> TYPE: PRT
<213> ORGANISM: Homo sapiens
<220> FEATURE:
<221> NAME/KEY: misc_feature
<222> LOCATION: (370)..(370)
<223> OTHER INFORMATION: Asn to Ser mutant

<400> SEQUENCE: 2

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
```

-continued

```
                65                  70                  75                  80
        Phe Gly Gly Ala Met Thr Asp Ala Ala Leu Asn Ile Leu Ala Leu
                         85                  90                  95
        Ser Pro Pro Ala Gln Asn Leu Leu Lys Ser Tyr Phe Ser Glu Glu
                        100                 105                 110
        Gly Ile Gly Tyr Asn Ile Ile Arg Val Pro Met Ala Ser Cys Asp Phe
                        115                 120                 125
        Ser Ile Arg Thr Tyr Thr Tyr Ala Asp Thr Pro Asp Asp Phe Gln Leu
                130                 135                 140
        His Asn Phe Ser Leu Pro Glu Glu Asp Thr Lys Leu Lys Ile Pro Leu
        145                 150                 155                 160
        Ile His Arg Ala Leu Gln Leu Ala Gln Arg Pro Val Ser Leu Leu Ala
                        165                 170                 175
        Ser Pro Trp Thr Ser Pro Thr Trp Leu Lys Thr Asn Gly Ala Val Asn
                        180                 185                 190
        Gly Lys Gly Ser Leu Lys Gly Gln Pro Gly Asp Ile Tyr His Gln Thr
                        195                 200                 205
        Trp Ala Arg Tyr Phe Val Lys Phe Leu Asp Ala Tyr Ala Glu His Lys
                210                 215                 220
        Leu Gln Phe Trp Ala Val Thr Ala Glu Asn Glu Pro Ser Ala Gly Leu
        225                 230                 235                 240
        Leu Ser Gly Tyr Pro Phe Gln Cys Leu Gly Phe Thr Pro Glu His Gln
                        245                 250                 255
        Arg Asp Phe Ile Ala Arg Asp Leu Gly Pro Thr Leu Ala Asn Ser Thr
                        260                 265                 270
        His His Asn Val Arg Leu Leu Met Leu Asp Asp Gln Arg Leu Leu Leu
                        275                 280                 285
        Pro His Trp Ala Lys Val Val Leu Thr Asp Pro Glu Ala Ala Lys Tyr
                        290                 295                 300
        Val His Gly Ile Ala Val His Trp Tyr Leu Asp Phe Leu Ala Pro Ala
        305                 310                 315                 320
        Lys Ala Thr Leu Gly Glu Thr His Arg Leu Phe Pro Asn Thr Met Leu
                        325                 330                 335
        Phe Ala Ser Glu Ala Cys Val Gly Ser Lys Phe Trp Glu Gln Ser Val
                        340                 345                 350
        Arg Leu Gly Ser Trp Asp Arg Gly Met Gln Tyr Ser His Ser Ile Ile
                        355                 360                 365
        Thr Ser Leu Leu Tyr His Val Val Gly Trp Thr Asp Trp Asn Leu Ala
                370                 375                 380
        Leu Asn Pro Glu Gly Gly Pro Asn Trp Val Arg Asn Phe Val Asp Ser
        385                 390                 395                 400
        Pro Ile Ile Val Asp Ile Thr Lys Asp Thr Phe Tyr Lys Gln Pro Met
                        405                 410                 415
        Phe Tyr His Leu Gly His Phe Ser Lys Phe Ile Pro Glu Gly Ser Gln
                        420                 425                 430
        Arg Val Gly Leu Val Ala Ser Gln Lys Asn Asp Leu Asp Ala Val Ala
                        435                 440                 445
        Leu Met Asn Pro Asp Gly Ser Ala Val Val Val Leu Asn Arg Ser
                450                 455                 460
        Ser Lys Asp Val Pro Leu Thr Ile Lys Asp Pro Ala Val Gly Phe Leu
        465                 470                 475                 480
        Glu Thr Ile Ser Pro Gly Tyr Ser Ile His Thr Tyr Leu Trp His Arg
                        485                 490                 495
```

Gln

<210> SEQ ID NO 3
<211> LENGTH: 497
<212> TYPE: PRT
<213> ORGANISM: Homo sapiens
<220> FEATURE:
<221> NAME/KEY: misc_feature
<222> LOCATION: (394)..(394)
<223> OTHER INFORMATION: Val to Leu mutant

<400> SEQUENCE: 3

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
```

-continued

```
                340                 345                 350
Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
        370                 375                 380

Leu Asn Pro Glu Gly Gly Pro Asn Trp Leu Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met Asn Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp His Arg
                485                 490                 495

Gln

<210> SEQ ID NO 4
<211> LENGTH: 497
<212> TYPE: PRT
<213> ORGANISM: Homo sapiens
<220> FEATURE:
<221> NAME/KEY: misc_feature
<222> LOCATION: (409)..(409)
<223> OTHER INFORMATION: Asp to His mutant

<400> SEQUENCE: 4

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190
```

```
Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Pro Ser Ala Gly Leu
225                 230                 235                 240

Leu Ser Gly Tyr Pro Phe Gln Cys Leu Gly Phe Thr Pro Glu His Gln
        245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys His Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met Asn Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp His Arg
                485                 490                 495

Gln

<210> SEQ ID NO 5
<211> LENGTH: 497
<212> TYPE: PRT
<213> ORGANISM: Homo sapiens
<220> FEATURE:
<221> NAME/KEY: misc_feature
<222> LOCATION: (444)..(444)
<223> OTHER INFORMATION: Leu to Pro mutant

<400> SEQUENCE: 5

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
        35                  40                  45
```

```
Met Glu Leu Ser Met Gly Pro Ile Gln Ala Asn His Thr Gly Thr Gly
 50                  55                  60
Leu Leu Leu Thr Leu Gln Pro Glu Gln Lys Phe Gln Lys Val Lys Gly
 65                  70                  75                  80
Phe Gly Gly Ala Met Thr Asp Ala Ala Ala Leu Asn Ile Leu Ala Leu
                 85                  90                  95
Ser Pro Pro Ala Gln Asn Leu Leu Lys Ser Tyr Phe Ser Glu Glu
            100                 105                 110
Gly Ile Gly Tyr Asn Ile Ile Arg Val Pro Met Ala Ser Cys Asp Phe
            115                 120                 125
Ser Ile Arg Thr Tyr Thr Tyr Ala Asp Thr Pro Asp Asp Phe Gln Leu
 130                 135                 140
His Asn Phe Ser Leu Pro Glu Glu Asp Thr Lys Leu Lys Ile Pro Leu
 145                 150                 155                 160
Ile His Arg Ala Leu Gln Leu Ala Gln Arg Pro Val Ser Leu Leu Ala
                 165                 170                 175
Ser Pro Trp Thr Ser Pro Thr Trp Leu Lys Thr Asn Gly Ala Val Asn
            180                 185                 190
Gly Lys Gly Ser Leu Lys Gly Gln Pro Gly Asp Ile Tyr His Gln Thr
            195                 200                 205
Trp Ala Arg Tyr Phe Val Lys Phe Leu Asp Ala Tyr Ala Glu His Lys
 210                 215                 220
Leu Gln Phe Trp Ala Val Thr Ala Glu Asn Glu Pro Ser Ala Gly Leu
225                  230                 235                 240
Leu Ser Gly Tyr Pro Phe Gln Cys Leu Gly Phe Thr Pro Glu His Gln
                 245                 250                 255
Arg Asp Phe Ile Ala Arg Asp Leu Gly Pro Thr Leu Ala Asn Ser Thr
                 260                 265                 270
His His Asn Val Arg Leu Leu Met Leu Asp Asp Gln Arg Leu Leu Leu
            275                 280                 285
Pro His Trp Ala Lys Val Val Leu Thr Asp Pro Glu Ala Ala Lys Tyr
 290                 295                 300
Val His Gly Ile Ala Val His Trp Tyr Leu Asp Phe Leu Ala Pro Ala
305                  310                 315                 320
Lys Ala Thr Leu Gly Glu Thr His Arg Leu Phe Pro Asn Thr Met Leu
                 325                 330                 335
Phe Ala Ser Glu Ala Cys Val Gly Ser Lys Phe Trp Glu Gln Ser Val
            340                 345                 350
Arg Leu Gly Ser Trp Asp Arg Gly Met Gln Tyr Ser His Ser Ile Ile
            355                 360                 365
Thr Asn Leu Leu Tyr His Val Val Gly Trp Thr Asp Trp Asn Leu Ala
 370                 375                 380
Leu Asn Pro Glu Gly Gly Pro Asn Trp Val Arg Asn Phe Val Asp Ser
385                  390                 395                 400
Pro Ile Ile Val Asp Ile Thr Lys Asp Thr Phe Tyr Lys Gln Pro Met
                 405                 410                 415
Phe Tyr His Leu Gly His Phe Ser Lys Phe Ile Pro Glu Gly Ser Gln
            420                 425                 430
Arg Val Gly Leu Val Ala Ser Gln Lys Asn Asp Pro Asp Ala Val Ala
            435                 440                 445
Leu Met Asn Pro Asp Gly Ser Ala Val Val Val Leu Asn Arg Ser
 450                 455                 460
```

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp His Arg
            485                 490                 495

Gln

<210> SEQ ID NO 6
<211> LENGTH: 497
<212> TYPE: PRT
<213> ORGANISM: Homo sapiens
<220> FEATURE:
<221> NAME/KEY: misc_feature
<222> LOCATION: (463)..(463)
<223> OTHER INFORMATION: Arg to Cys mutant

<400> SEQUENCE: 6

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
        50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

```
Lys Ala Thr Leu Gly Glu Thr His Arg Leu Phe Pro Asn Thr Met Leu
            325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Gly Trp Thr Asp Trp Asn Leu Ala
        370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
                420                 425                 430

Arg Val Gly Leu Val Ala Ser Gln Lys Asn Asp Leu Asp Ala Val Ala
            435                 440                 445

Leu Met Asn Pro Asp Gly Ser Ala Val Val Val Leu Asn Cys Ser
        450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp His Arg
                485                 490                 495

Gln

<210> SEQ ID NO 7
<211> LENGTH: 497
<212> TYPE: PRT
<213> ORGANISM: Homo sapiens
<220> FEATURE:
<221> NAME/KEY: misc_feature
<222> LOCATION: (496)..(496)
<223> OTHER INFORMATION: Arg to His mutant

<400> SEQUENCE: 7

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
```

-continued

```
                165                 170                 175
Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met Asn Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp His Arg
                485                 490                 495

Gln

<210> SEQ ID NO 8
<211> LENGTH: 497
<212> TYPE: PRT
<213> ORGANISM: Homo sapiens

<400> SEQUENCE: 8

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
```

```
                 35                  40                  45
Met Glu Leu Ser Met Gly Pro Ile Gln Ala Asn His Thr Gly Thr Gly
 50                  55                  60

Leu Leu Leu Thr Leu Gln Pro Glu Gln Lys Phe Gln Lys Val Lys Gly
 65                  70                  75                  80

Phe Gly Gly Ala Met Thr Asp Ala Ala Ala Leu Asn Ile Leu Ala Leu
                     85                  90                  95

Ser Pro Pro Ala Gln Asn Leu Leu Lys Ser Tyr Phe Ser Glu Glu
                    100                 105                 110

Gly Ile Gly Tyr Asn Ile Ile Arg Val Pro Met Ala Ser Cys Asp Phe
                115                 120                 125

Ser Ile Arg Thr Tyr Thr Tyr Ala Asp Thr Pro Asp Asp Phe Gln Leu
            130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                    165                 170                 175

Ser Pro Trp Thr Ser Pro Thr Trp Leu Lys Thr Asn Gly Ala Val Asn
                180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
            210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                    245                 250                 255

Arg Asp Phe Ile Ala Arg Asp Leu Gly Pro Thr Leu Ala Asn Ser Thr
                260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                    325                 330                 335

Phe Ala Ser Glu Ala Cys Val Gly Ser Lys Phe Trp Glu Gln Ser Val
                340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                    405                 410                 415

Phe Tyr His Leu Gly His Phe Ser Lys Phe Ile Pro Glu Gly Ser Gln
                420                 425                 430

Arg Val Gly Leu Val Ala Ser Gln Lys Asn Asp Leu Asp Ala Val Ala
            435                 440                 445

Leu Met Asn Pro Asp Gly Ser Ala Val Val Val Leu Asn Arg Ser
            450                 455                 460
```

```
Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 9
<211> LENGTH: 497
<212> TYPE: PRT
<213> ORGANISM: Homo sapiens
<220> FEATURE:
<221> NAME/KEY: misc_feature
<222> LOCATION: (370)..(370)
<223> OTHER INFORMATION: Asn ot Ser mutant

<400> SEQUENCE: 9

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
```

-continued

```
              305                 310                 315                 320
Lys Ala Thr Leu Gly Glu Thr His Arg Leu Phe Pro Asn Thr Met Leu
                    325                 330                 335

Phe Ala Ser Glu Ala Cys Val Gly Ser Lys Phe Trp Glu Gln Ser Val
                340                 345                 350

Arg Leu Gly Ser Trp Asp Arg Gly Met Gln Tyr Ser His Ser Ile Ile
            355                 360                 365

Thr Ser Leu Leu Tyr His Val Val Gly Trp Thr Asp Trp Asn Leu Ala
        370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
                420                 425                 430

Arg Val Gly Leu Val Ala Ser Gln Lys Asn Asp Leu Asp Ala Val Ala
            435                 440                 445

Leu Met Asn Pro Asp Gly Ser Ala Val Val Val Leu Asn Arg Ser
        450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln
```

<210> SEQ ID NO 10
<211> LENGTH: 497
<212> TYPE: PRT
<213> ORGANISM: Homo sapiens
<220> FEATURE:
<221> NAME/KEY: misc_feature
<222> LOCATION: (394)..(394)
<223> OTHER INFORMATION: Val to Leu mutant

<400> SEQUENCE: 10

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
        50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160
```

```
Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Leu Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met Asn Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln
```

<210> SEQ ID NO 11
<211> LENGTH: 497
<212> TYPE: PRT
<213> ORGANISM: Homo sapiens
<220> FEATURE:
<221> NAME/KEY: misc_feature
<222> LOCATION: (409)..(409)
<223> OTHER INFORMATION: Asp to His mutant

<400> SEQUENCE: 11

```
Ala Arg Pro Cys Ile Pro Lys Ser Phe Gly Tyr Ser Ser Val Val Cys
1               5                   10                  15
```

-continued

```
Val Cys Asn Ala Thr Tyr Cys Asp Ser Phe Asp Pro Thr Phe Pro
             20                  25                  30

Ala Leu Gly Thr Phe Ser Arg Tyr Glu Ser Thr Arg Ser Gly Arg Arg
             35                  40                  45

Met Glu Leu Ser Met Gly Pro Ile Gln Ala Asn His Thr Gly Thr Gly
             50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Leu Asn Ile Leu Ala Leu
                 85                  90                  95

Ser Pro Pro Ala Gln Asn Leu Leu Lys Ser Tyr Phe Ser Glu Glu
             100                 105                 110

Gly Ile Gly Tyr Asn Ile Ile Arg Val Pro Met Ala Ser Cys Asp Phe
             115                 120                 125

Ser Ile Arg Thr Tyr Thr Tyr Ala Asp Thr Pro Asp Asp Phe Gln Leu
             130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                 165                 170                 175

Ser Pro Trp Thr Ser Pro Thr Trp Leu Lys Thr Asn Gly Ala Val Asn
             180                 185                 190

Gly Lys Gly Ser Leu Lys Gly Gln Pro Gly Asp Ile Tyr His Gln Thr
             195                 200                 205

Trp Ala Arg Tyr Phe Val Lys Phe Leu Asp Ala Tyr Ala Glu His Lys
             210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                 245                 250                 255

Arg Asp Phe Ile Ala Arg Asp Leu Gly Pro Thr Leu Ala Asn Ser Thr
             260                 265                 270

His His Asn Val Arg Leu Leu Met Leu Asp Asp Gln Arg Leu Leu Leu
             275                 280                 285

Pro His Trp Ala Lys Val Val Leu Thr Asp Pro Glu Ala Ala Lys Tyr
             290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                 325                 330                 335

Phe Ala Ser Glu Ala Cys Val Gly Ser Lys Phe Trp Glu Gln Ser Val
             340                 345                 350

Arg Leu Gly Ser Trp Asp Arg Gly Met Gln Tyr Ser His Ser Ile Ile
             355                 360                 365

Thr Asn Leu Leu Tyr His Val Val Gly Trp Thr Asp Trp Asn Leu Ala
             370                 375                 380

Leu Asn Pro Glu Gly Gly Pro Asn Trp Val Arg Asn Phe Val Asp Ser
385                 390                 395                 400

Pro Ile Ile Val Asp Ile Thr Lys His Thr Phe Tyr Lys Gln Pro Met
                 405                 410                 415

Phe Tyr His Leu Gly His Phe Ser Lys Phe Ile Pro Glu Gly Ser Gln
             420                 425                 430
```

```
Arg Val Gly Leu Val Ala Ser Gln Lys Asn Asp Leu Asp Ala Val Ala
        435                 440                 445

Leu Met Asn Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 12
<211> LENGTH: 497
<212> TYPE: PRT
<213> ORGANISM: Homo sapiens
<220> FEATURE:
<221> NAME/KEY: misc_feature
<222> LOCATION: (444)..(444)
<223> OTHER INFORMATION: Leu to Pro

<400> SEQUENCE: 12

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
                100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
    195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
    275                 280                 285
```

-continued

```
Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Pro Asp Ala Val Ala
        435                 440                 445

Leu Met Asn Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 13
<211> LENGTH: 497
<212> TYPE: PRT
<213> ORGANISM: Homo sapiens
<220> FEATURE:
<221> NAME/KEY: misc_feature
<222> LOCATION: (463)..(463)
<223> OTHER INFORMATION: Arg to Cys mutant

<400> SEQUENCE: 13

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
        50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
```

```
            130                 135                 140
His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met Asn Pro Asp Gly Ser Ala Val Val Val Leu Asn Cys Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 14
<211> LENGTH: 497
<212> TYPE: PRT
<213> ORGANISM: Homo sapiens
<220> FEATURE:
<221> NAME/KEY: misc_feature
<222> LOCATION: (496)..(496)
<223> OTHER INFORMATION: Arg to His mutant
```

<400> SEQUENCE: 14

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Leu Asn Ile Leu Ala Leu
            85                  90                  95

Ser Pro Pro Ala Gln Asn Leu Leu Lys Ser Tyr Phe Ser Glu Glu
            100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
            165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
            245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
            325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
```

```
                    405                 410                 415
Phe Tyr His Leu Gly His Phe Ser Lys Phe Ile Pro Glu Gly Ser Gln
                420                 425                 430

Arg Val Gly Leu Val Ala Ser Gln Lys Asn Asp Leu Asp Ala Val Ala
            435                 440                 445

Leu Met Asn Pro Asp Gly Ser Ala Val Val Val Leu Asn Arg Ser
        450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 15
<211> LENGTH: 3
<212> TYPE: PRT
<213> ORGANISM: Artificial sequence
<220> FEATURE:
<223> OTHER INFORMATION: N-linked glycosylation consensus sequence
<220> FEATURE:
<221> NAME/KEY: misc_feature
<222> LOCATION: (2)..(2)
<223> OTHER INFORMATION: Any amino acid
<220> FEATURE:
<221> NAME/KEY: misc_feature
<222> LOCATION: (3)..(3)
<223> OTHER INFORMATION: Ser or Thr

<400> SEQUENCE: 15

Asn Xaa Xaa
1

<210> SEQ ID NO 16
<211> LENGTH: 497
<212> TYPE: PRT
<213> ORGANISM: Pan troglodytes

<400> SEQUENCE: 16

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Thr Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
```

-continued

|     | 165 |     |     |     | 170 |     |     |     | 175 |     |     |
|-----|-----|-----|-----|-----|-----|-----|-----|-----|-----|-----|-----|
| Ser | Pro | Trp | Thr | Ser | Pro | Thr | Trp | Leu | Lys | Thr | Asn | Gly | Ala | Val | Asn |

Ser Pro Trp Thr Ser Pro Thr Trp Leu Lys Thr Asn Gly Ala Val Asn
                180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
        210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
                260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
        290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
                340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
            435                 440                 445

Leu Met His Pro Asp Gly Ser Ala Val Val Val Leu Asn Arg Ser
        450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

PARTIALLY DEGLYCOSYLATED GLUCOCEREBROSIDASE POLYPEPTIDE AND CRYSTALS THEREOF

RELATED PATENT APPLICATION

This application is a National Phase Application of PCT/IL2004/000335 having International Filing Date of 18 Apr. 2004, which claims priority from IL Patent Application No. 156273, filed on Jun. 2, 2003. The contents of the above Applications are all incorporated herein by reference.

SEQUENCE LISTING

A Sequence Listing appendix may be found following the Abstract.

FIELD AND BACKGROUND OF THE INVENTION

The present invention relates to methods of identifying compounds capable of regulating the activity of mutant enzymes, to computing platforms capable of generating models representing 3D structures of crystallized enzymes, to crystallized enzymes, and to methods of crystallizing enzymes. In particular, embodiments of the present invention relate to methods of identifying compounds capable of correcting impaired enzymatic activity of mutant human glucocerebrosidase molecules associated with Gaucher disease, to computing platforms capable of generating models representing essentially complete experimentally determined 3D structures of crystallized human glucocerebrosidase polypeptide, to crystallized human glucocerebrosidase polypeptide, and to methods of crystallizing human glucocerebrosidase polypeptide. The present invention further relates to preparations of partially glycosylated glucocerebrosidase molecules having about the same capacity to catalyze hydrolysis of a glucocerebroside as preparations of fully glycosylated glucocerebrosidase molecules, such as Cerezyme®, having optimal stability of such capacity under physiological conditions, and being capable of undergoing significant internalization/uptake by a phagocyte, such as a macrophage. In particular, the present invention relates to methods of using such preparations for treating diseases associated with glucocerebrosidase deficiency, such as Gaucher disease.

Gaucher disease, the most common lysosomal storage disease (Meikle P J. et al., 1999. JAMA 281:249-54), is a highly debilitating disease occurring with a frequency of 1 in 40,000-60,000 in the general population, and 1 in 500-1,000 amongst Ashkenazi Jews [Beutler E. and Grabowski G A., in: "The Metabolic and Molecular Bases of Inherited Disease", Scriver C R. et al. (eds.), McGraw-Hill Inc., pp. 3635-3668 (2001)]. Due to its genetic component, Gaucher disease represents a genetic testing dilemma for potential carriers. The disease occurs in various forms, in particular Type 1 which is predominantly characterized by hepatosplenomegaly; and Types 2 and 3 which are characterized by early or chronic onset of severe neurological symptoms. In Gaucher disease, deficiency in enzymatic activity of the lysosomal enzyme glucocerebrosidase due to mutations in the enzyme [Beutler E. and Grabowski G A., in: "The Metabolic and Molecular Bases of Inherited Disease", Scriver C R. et al. (eds.), McGraw-Hill Inc., pp. 3635-3668 (2001)] leads to pathological lysosomal accumulation of the lipid glucosylceramide (GlcCer or glucocerebroside), principally in macrophages, but also in monocytes, and, in severe cases, in neurons. The lysosomal accumulation of glucosylceramide leads to buildup of congested lysosomes at various anatomic sites throughout the body, including the liver, spleen and bone marrow, which in turn causes anemia and osteopenia. Gaucher disease may also be associated with highly debilitating conditions, such as glomerulonephritis, pericarditis, pericardial calcification, haemorrhagic colitis and/or amyloidosis.

Glucosylceramide, whose pathological accumulation is associated with Gaucher disease, belongs to a family of lipids called sphingolipids which play important roles in normal cell physiology. Gaucher disease is one of the group of "sphingolipid storage diseases" which also include Tay-Sachs and Niemann-Pick disease. Sphingolipids have received huge attention over the past couple of decades since it was shown that they are involved in regulation of cell physiology via signal transduction. While thousands of scientific papers have been published during this period on basic aspects of sphingolipid research, surprisingly little is known about the molecular mechanisms by which sphingolipid accumulation leads to sphingolipid storage diseases, or in the case of Gaucher disease, how glucosylceramide accumulation causes cell dysfunction. In 1999, the present inventors performed an experiment which gave clues to the pathophysiological mechanism that might be responsible for neurological disease in types 2 and 3 Gaucher disease. Over the past 4 to 5 years, these findings have been formulated into the "calcium hypothesis" in which the present inventors suggested that defective calcium homeostasis is responsible for the altered neuronal dysfunction in neuronopathic forms of Gaucher disease, which results in brain dysfunction (work summarized in: Korkotian, E. et al., 1999. J. Biol. Chem. 274:21673-21678; Pelled, D. et al., 2000. J. Inh. Met. Dis. 23, 175-184; Lloyd-Evans, E. et al., 2003. J. Biol. Chem. 278:23594-23599; Pelled, D. et al., Enhanced calcium release in the acute neuronopathic form of Gaucher disease. Submitted for publication).

The enzyme glucocerebrosidase (EC 3.2.1.45, acid beta-glucosidase, D-glucosyl-N-acylsphingosine glucohydrolase, glucosylceramidase) is a peripheral membrane protein which hydrolyzes the beta-glucosyl linkage of glucosylceramide in lysosomes, thereby generating beta-glucose and ceramide (FIG. 1a). This enzymatic activity requires the coordinate action of saposin C and negatively-charged lipids for maximal activity [Beutler E. and Grabowski G A., in: "The Metabolic and Molecular Bases of Inherited Disease", Scriver C R. et al. (eds.), McGraw-Hill Inc., pp. 3635-3668 (2001); Grabowski G A. et al., 1990. Critical Rev Biochem Mol Biol. 25:385-414]. Based on sequence similarity, glucocerebrosidase is classified as a member of glycoside hydrolase family 30 (see website of ARCHITECTURE ET FONCTION DES MACROMOLECULES BIOLOGIQUES, France).

Of the approximately 200 known glucocerebrosidase mutations, homozygosity for the common mutations Asn370Ser and Leu444Pro is associated with non-neuronopathic (Charrow J. et al., 2000. Arch Intern Med. 160:2835-43) and neuronopathic [Erikson A. et al. in: "Gaucher Disease", Zimran A. (ed.), Bailliere Tindall, London, pp. 711-723 (1997)] Gaucher disease, respectively. Mutation Asn370Ser is the most common mutation, accounting for about 70 and 25 percent of the mutant alleles in Ashkenazi Jewish and non-Jewish patients, respectively [Beutler E. and Grabowski G A., in: "The Metabolic and Molecular Bases of Inherited Disease", Scriver C R. et al. (eds.), McGraw-Hill Inc., pp. 3635-3668 (2001)]. Many of the glucocerebrosidase mutations (FIG. 1d) are rare and restricted to a few individuals, and most partially or entirely decrease catalytic activity (Meivar-Levy, I. et al., 1994. Biochem. J. 303:377-382) or may reduce glucocerebrosidase stability (Grace M E. et al., 1994. J Biol. Chem. 269:2283-2291).

Whole-enzyme replacement therapy with Cerezyme®, a recombinant variant of human glucocerebrosidase (Grabowski G A. et al., 1995. Ann Intern Med. 122:33-9) is the main treatment for Type 1 Gaucher disease. Such treatment, however, is not curative, nor does it satisfactorily alleviate the symptoms of the disease. Furthermore, such whole-enzyme replacement therapy has numerous significant disadvantages, including: (i) administration of a molecule having various suboptimal pharmacokinetic characteristics, including suboptimal tissue penetration as a result of its large size; and suboptimal plasma membrane permeability and in-vivo half-life due to its polypeptidic composition; (ii) incapacity to correct endogenous glucocerebrosidase enzyme activity, and thereby incapacity to therapeutically confer such activity with optimal spatial (cell type/subcellular location), temporal, and activity level regulation; (iii) for optimal therapeutic results, the need to administer the enzyme via injection, a painful, inconvenient, and expensive process; and (iv) elicitation of harmful immune responses against the administered enzyme in a substantial proportion of treated subjects as a result of its polypeptidic/modified oligosaccharide chemical composition (see entry for "Cerezyme" in the website of the Gaucher Registry. Hence, there is a clearly felt need for novel/improved Gaucher disease drugs.

One approach for attempting to correct the defective enzymatic activity of the glucocerebrosidase Asn370Ser mutant which has been proposed in the prior art involves utilizing deoxynijirimycin (DNJ)-based compounds (Sawkar et al., 2002. Proc Natl Acad Sci USA. 99:15428-33). Such an approach, however, suffers from significant drawbacks, including: (i) the nonspecific inhibitory effect of DNJ compounds on enzymes that make and break glucosyl bonds, such as endoplasmic reticulum oligosaccharide-processing enzymes alpha-glucosidase I/II, ceramide glucosyl transferase, and both non-lysosomal and lysosomal glucocerebrosidase; (ii) the significant toxicity displayed by DNJ compounds; and (iii) the fact that DNJ compounds have not been demonstrated to have a significant restorative effect on the impaired enzymatic activity of any glucocerebrosidase mutant other than Asn370Ser, including a demonstrated ineffectiveness for correcting impaired enzymatic activity of the common Leu444Pro glucocerebrosidase mutant.

Thus, in sharp contrast to prior art Gaucher disease drugs, optimal Gaucher disease drugs, would be compounds having optimally small dimensions, a non-polypeptidic chemical composition, a capacity to correct impaired enzymatic activity of any of various glucocerebrosidase mutants, and would be capable of correcting the impaired enzymatic activity of glucocerebrosidase mutants associated with Gaucher disease in-vivo with optimal effectiveness and safety.

Ideally, such compounds could be computationally identified by obtaining sets of structure coordinates defining experimentally determined 3D structures of glucocerebrosidase at atomic resolution, using such sets of structure coordinates for producing computational platforms capable of generating models representing such 3D structures of human glucocerebrosidase at such atomic resolution, and using such computing platforms for computationally identifying compounds capable of interacting with mutant human glucocerebrosidase molecules associated with Gaucher disease in such a way as to correct impaired enzymatic activity thereof.

One prior art approach which has been employed involves using two-dimensional hydrophobic cluster analysis in attempts to provide sets of structure coordinates defining predictive structures of human glucocerebrosidase molecules (Fabrega S. et al., 2002. J Soc Biol. 196:151-60; Fabrega S. et al., 2000. Glycobiology 10:1217-24).

Another approach which has been employed involves crystallizing Cerezyme® and analyzing such crystals via X-ray crystallography in attempts to generate X-ray diffraction data defining 3D structures of Cerezyme® suitable for computational identification of novel Gaucher disease drugs (Roeber D. et al., 2003. Acta Cryst. D59:343-344).

These prior art approaches, however, have essentially failed. Approaches involving predictive methods based on two-dimensional hydrophobic cluster analysis are suboptimal due to the significant inaccuracies inherent to such predictive methods, and, in any case, have not provided sets of structure coordinates defining the structure of glucocerebrosidase, nor of significant portions thereof, at adequately high resolution, with satisfactory completeness, and with a satisfactory degree of accuracy. Furthermore, approaches involving crystallization of Cerezyme® have not succeeded in producing crystals capable of generating X-ray diffraction data defining structures of Cerezyme® or portions thereof.

Various partially glycosylated glucocerebrosidase preparations have been described in the prior art (as used herein, the phrase "partially glycosylated glucocerebrosidase" refers to a glucocerebrosidase molecule whose amino acid sequence includes at least one fully unglycosylated amino acid residue at a position normally corresponding to a glycosylated Asn residue).

One such approach involves individually or collectively replacing in human glucocerebrosidase via site-directed mutagenesis Asn residues which are glycosylated with a non-glycosylated amino acid residue (Berg-Fussman A. et al., 1993. J Biol Chem. 268:14861-14866) to generate, for each amino acid residue at a position corresponding a normally glycosylated Asn residue, a point-mutant glucocerebrosidase preparation having one unglycosylated amino acid residue at a position corresponding a normally glycosylated Asn residue, or a quadruple point-mutant glucocerebrosidase preparation having all four amino acid residues at positions corresponding a normally glycosylated Asn residue such residues being unglycosylated.

Another approach involves subjecting porcine glucocerebrosidase to sequential deglycosylation with endoglycosidase H so as to obtain preparations of porcine glucocerebrosidase having only three, only two or only one glycosylated Asn residues out of the four normally glycosylated Asn residues (Erickson A H et al., 1985. J Biol Chem. 260:14319-24).

These prior art partially glycosylated glucocerebrosidase preparations are suboptimal for treatment of a disease associated with glucocerebrosidase deficiency, such as Gaucher disease in humans, via enzyme replacement therapy for various reasons. The approach involving mutagenesis failed to generate a mutant glucocerebrosidase preparation demonstrably having either improved enzymatic activity, or improved stability of such activity under physiological conditions. The approach employing enzymatic deglycosylation failed to demonstrate that any of the glycoforms generated has any enzymatic activity, failed to characterize which Asn residues were glycosylated/deglycosylated in any of the preparations, and involve a glucocerebrosidase of porcine origin.

Thus, all prior art approaches have failed to provide an adequate solution for producing computational platforms suitable for computationally identifying compounds capable of interacting with mutant human glucocerebrosidase molecules associated with Gaucher disease in such a way as to correct impaired enzymatic activity thereof, and have failed to provide an adequate solution for treatment of Gaucher disease via enzyme replacement therapy.

There is thus a widely recognized need for, and it would be highly advantageous to have, a computing platform for identifying optimal Gaucher disease drugs, and a glucocerebrosidase preparation for treating Gaucher disease devoid of the above limitations.

SUMMARY OF THE INVENTION

According to one aspect of the present invention there is provided a method of crystallizing a glucocerebrosidase molecule, the method comprising: (a) partially deglycosylating the glucocerebrosidase molecule, thereby generating a partially glycosylated glucocerebrosidase molecule; and (b) subjecting the partially glycosylated glucocerebrosidase molecule to crystallization-inducing conditions, thereby crystallizing the glucocerebrosidase molecule.

According to further features in preferred embodiments of the invention described below, the step of partially deglycosylating the glucocerebrosidase molecule is effected by treating the glucocerebrosidase molecule with N-glycosidase F.

According to still further features in the described preferred embodiments, an amino acid sequence of the glucocerebrosidase molecule comprises a first N-linked glycosylation consensus sequence, wherein the first N-linked glycosylation consensus sequence is attached to a sugar moiety comprising a monosaccharide or a disaccharide directly attached to the first N-linked glycosylation consensus sequence, and whereas the step of partially deglycosylating the glucocerebrosidase molecule is effected so as to leave the monosaccharide or the disaccharide attached to the first N-linked glycosylation consensus sequence.

According to still further features in the described preferred embodiments, the step of partially deglycosylating the glucocerebrosidase molecule is further effected so as to effectively fully deglycosylate all glycosylated N-linked glycosylation consensus sequences of the amino acid sequence of the glucocerebrosidase molecule other than the first N-linked glycosylation consensus sequence of the amino acid sequence of the glucocerebrosidase molecule.

According to still further features in the described preferred embodiments, the crystallization-inducing conditions comprise inducing evaporation of a crystallization solution containing the at least partially deglycosylated glucocerebrosidase molecule at a concentration of about 5 mg/ml, and a component selected from the group consisting of a buffer, a sodium salt, an ammonium salt, a sulfate salt, a chaotropic compound, a potassium salt, and a chloride ion.

According to still further features in the described preferred embodiments, the buffer is a Zwitterionic buffer or an acetate buffer.

According to still further features in the described preferred embodiments, the buffer is 2-morpholinoethanesulfonic acid buffer or sodium acetate buffer.

According to still further features in the described preferred embodiments, the crystallization solution contains the buffer at a concentration of about 0.5 millimolar or about 0.05 molar.

According to still further features in the described preferred embodiments, the solution of a buffer has a pH of about 6.6 or about 4.6.

According to still further features in the described preferred embodiments, the sodium salt is sodium chloride.

According to still further features in the described preferred embodiments, the crystallization solution contains the sodium salt at a concentration of about 0.05 molar.

According to still further features in the described preferred embodiments, the ammonium salt is ammonium sulfate.

According to still further features in the described preferred embodiments, the crystallization solution contains the ammonium salt at a concentration of about 0.5 molar.

According to still further features in the described preferred embodiments, the crystallization solution contains the sulfate salt at a concentration of about 0.5 molar.

According to still further features in the described preferred embodiments, the chaotropic compound is guanidine hydrochloride.

According to still further features in the described preferred embodiments, the crystallization solution contains the chaotropic compound at a concentration of about 0.085 molar.

According to still further features in the described preferred embodiments, the potassium salt is potassium chloride.

According to still further features in the described preferred embodiments, the crystallization solution contains the potassium salt at a concentration of about 0.01 molar.

According to still further features in the described preferred embodiments, the crystallization solution contains the chloride ion at a concentration of about 0.06 molar.

According to still further features in the described preferred embodiments, the crystallization solution has a pH of about 4.6.

According to still further features in the described preferred embodiments, inducing evaporation of the crystallization solution is effected at a temperature of about 22 degrees centigrade.

According to another aspect of the present invention there is provided a method of identifying a compound capable of correcting an impaired enzymatic activity of a mutant glucocerebrosidase molecule, the method comprising: (a) obtaining a first set of structure coordinates, the first set of structure coordinates defining a 3D structure of a glucocerebrosidase molecule capable of displaying normal enzymatic activity or a portion thereof, (b) computationally generating using the first set of structure coordinates a second set of structure coordinates, the second set of structure coordinates defining a predicted 3D structure of the mutant glucocerebrosidase molecule or a portion thereof, and (c) computationally identifying, using the second set of structure coordinates, a compound capable of interacting with the mutant glucocerebrosidase molecule in such a way as to correct the impaired enzymatic activity thereof, thereby identifying the compound capable of correcting the impaired enzymatic activity of the mutant glucocerebrosidase molecule.

According to further features in preferred embodiments of the invention described below, the step of computationally identifying using the second set of structure coordinates a compound capable of interacting with the mutant glucocerebrosidase molecule is effected further using the first set of structure coordinates.

According to still further features in the described preferred embodiments, the method of identifying a compound capable of correcting an impaired enzymatic activity of a mutant glucocerebrosidase molecule further comprises biochemically qualifying a capacity of the compound to correct the impaired enzymatic activity of the mutant glucocerebrosidase molecule.

According to still further features in the described preferred embodiments, the amino acid sequence of the glucocerebrosidase molecule capable of displaying normal enzymatic activity is set forth in SEQ ID NO: 1.

According to still further features in the described preferred embodiments, the amino acid sequence of the glucocerebrosidase molecule capable of displaying normal enzymatic activity is composed of 497 amino acid residues, and the portion of the glucocerebrosidase molecule capable of displaying normal enzymatic activity comprises a set of amino acid residues of the amino acid sequence of the glucocerebrosidase molecule having normal activity having amino acid sequence coordinates selected from the group consisting of: (i) 76, 81, 285, 312, 314, 320, 324, 325, 336, 364-378, 423, and 433; (ii) 244-247, and 390-397; (iii) 20, 21, 95-100, and 404-411; (iv) 65-67, 440-447, 460-464, 468, and 469; (v) 360-366, 443-446, 460-467, and 484-89; and (vi) 33-35, 69, 71, 450-456, 474-478, and 493-497.

According to still further features in the described preferred embodiments, the amino acid sequence of the mutant glucocerebrosidase molecule is composed of 497 amino acid residues, and the portion of the mutant glucocerebrosidase molecule comprises a set of amino acid residues of the amino acid sequence of the mutant glucocerebrosidase molecule having amino acid sequence coordinates selected from the group consisting of: (i) 76, 81, 285, 312, 314, 320, 324, 325, 336, 364-378, 423, and 433; (ii) 244-247, and 390-397; (iii) 20, 21, 95-100, and 404-411; (iv) 65-67, 440-447, 460-464, 468, and 469; (v) 360-366, 443-446, 460-467, and 484-89; and (vi) 33-35, 69, 71, 450-456, 474-478, and 493-497.

According to still further features in the described preferred embodiments, the first set of structure coordinates comprises a set of structure coordinates set forth in Table 4, 5, 6, 7, 8, 9, and/or 10.

According to still further features in the described preferred embodiments, the amino acid sequence of the mutant glucocerebrosidase molecule is set forth in SEQ ID NO: 2, 3, 4, 5, 6, or 7.

According to still further features in the described preferred embodiments, the second set of structure coordinates comprises a set of structure coordinates set forth in Table 11, 12, 13, 14, 15, 16, 17, 18, 19, 20, 21, and/or 22.

According to still further features in the described preferred embodiments, the glucocerebrosidase molecule capable of displaying normal enzymatic activity is a crystallized glucocerebrosidase molecule.

According to yet another aspect of the present invention there is provided a computing platform capable of generating a model representing a 3D structure of a glucocerebrosidase molecule or a portion thereof, the computing platform comprising: (a) a data-storage device storing data comprising a set of structure coordinates defining the 3D structure of the glucocerebrosidase molecule or the portion thereof; and (b) a processing unit being for generating the model representing the 3D structure from the data stored in the data-storage device.

According to further features in preferred embodiments of the invention described below, the glucocerebrosidase molecule is a glucocerebrosidase molecule capable of displaying normal enzymatic activity, or is a mutant glucocerebrosidase molecule.

According to still further features in the described preferred embodiments, the amino acid sequence of the glucocerebrosidase molecule is set forth in SEQ ID NO: 1, 2, 3, 4, 5, 6, or 7.

According to still further features in the described preferred embodiments, the amino acid sequence of the glucocerebrosidase molecule is composed of 497 amino acid residues, and the portion of the glucocerebrosidase molecule comprises a set of amino acid residues of the amino acid sequence having amino acid sequence coordinates selected from the group consisting of: (i) 76, 81, 285, 312, 314, 320, 324, 325, 336, 364-378, 423, and 433; (ii) 244-247, and 390-397; (iii) 20, 21, 95-100, and 404-411; (iv) 65-67, 440-447, 460-464, 468, and 469; (v) 360-366, 443-446, 460-467, and 484-89; and (vi) 33-35, 69, 71, 450-456, 474-478, and 493-497.

According to still further features in the described preferred embodiments, the set of structure coordinates comprises a set of structure coordinates set forth in Table 4, 5, 6, 7, 8, 9, 10, 11, 12, 13, 14, 15, 16, 17, 18, 19, 20, 21, and/or 22.

According to still further features in the described preferred embodiments, the glucocerebrosidase molecule is a crystallized glucocerebrosidase molecule.

According to still another aspect of the present invention there is provided a composition-of-matter comprising a crystallized glucocerebrosidase molecule, wherein the crystallized glucocerebrosidase molecule is characterized by an X-ray diffraction capacity enabling generation of a set of structure coordinates defining a 3D structure of the glucocerebrosidase molecule or a portion thereof, to a resolution of 2.9 angstroms or higher; and/or wherein an amino acid sequence of the glucocerebrosidase molecule is partially glycosylated.

According to further features in preferred embodiments of the invention described below, the crystallized glucocerebrosidase molecule is characterized by unit cell dimensions of a=about 107.7 angstroms, b=about 285.2 angstroms and c=about 91.8 angstroms.

According to still further features in the described preferred embodiments, the crystallized glucocerebrosidase molecule is characterized by a crystal space group of $C222_1$.

According to a further aspect of the present invention there is provided a computer-readable medium comprising, in a retrievable format, data including a set of structure coordinates defining a 3D the set of structure coordinates defines the 3D structure at a resolution of 2.9 angstroms or higher, and/or wherein an amino acid sequence of the glucocerebrosidase molecule is partially glycosylated.

According to yet a further aspect of the present invention there is provided a computer generated model representing a 3D structure of a glucocerebrosidase molecule or a portion thereof, wherein the model represents the glucocerebrosidase molecule or a portion thereof at a resolution of 2.9 angstroms or higher, and/or wherein the an amino acid sequence of the glucocerebrosidase molecule is partially glycosylated.

According to still further features in the described preferred embodiments, the partially glycosylated amino acid sequence comprises a first N-linked glycosylation consensus sequence attached to a sugar.

According to still further features in the described preferred embodiments, the set of structure coordinates defines the 3D structure to a resolution of 2.9 angstroms or higher According to still further features in the described preferred embodiments, the amino acid sequence of the glucocerebrosidase molecule is partially glycosylated.

According to still further features in the described preferred embodiments, the glucocerebrosidase molecule is capable of displaying normal enzymatic activity.

According to still further features in the described preferred embodiments, the amino acid sequence of the glucocerebrosidase molecule is set forth in SEQ ID NO: 1.

According to still further features in the described preferred embodiments, the set of structure coordinates comprises a set of structure coordinates set forth in Table 4, 5, 6, 7, 8, 9, and/or 10.

According to one aspect of the present invention there is provided a method of producing a glucocerebrosidase preparation suitable for treatment of a disease associated with glucocerebrosidase deficiency, the method comprising exposing a plurality of glucocerebrosidase molecules to conditions suitable for partial deglycosylation thereof so as to form a population of partially deglycosylated glucocerebrosidase molecules each characterized by an amino acid sequence: (i) glycosylated at, or having an aspartatic acid residue at, glycosylation residue 1 thereof, and (ii) lacking glycosylation at one or more glycosylation residues thereof selected from the group consisting of glycosylation residues 2, 3 and 4, thereby producing a glucocerebrosidase preparation suitable for treatment of a disease associated with glucocerebrosidase deficiency.

According to further features in preferred embodiments of the invention described below, the method of producing a glucocerebrosidase preparation further comprises, prior to and/or concomitantly with the exposing the plurality of glucocerebrosidase molecules to the conditions, subjecting the plurality of glucocerebrosidase molecules to conditions suitable for exposing at least one mannose residue of at least one glycosylation moiety of each of at least some of the glucocerebrosidase molecules of the plurality of glucocerebrosidase molecules.

According to still further features in the described preferred embodiments, the method of producing the glucocerebrosidase preparation further comprises subjecting the plurality of partially deglycosylated glucocerebrosidase molecules to conditions suitable for exposing at least one mannose residue of at least one glycosylation moiety of each at least some of the partially glycosylated glucocerebrosidase molecules.

According to still further features in the described preferred embodiments, the conditions suitable for partial deglycosylation of the glucocerebrosidase molecules include treating the plurality of glucocerebrosidase molecules with a glycosidase.

According to still further features in the described preferred embodiments, the conditions suitable for partial deglycosylation of the glucocerebrosidase molecules include treating the plurality of glucocerebrosidase molecules with peptide N-glycosidase F.

According to still further features in the described preferred embodiments, the amino acid sequence is at least 95 percent homologous to an amino acid sequence set forth by SEQ ID NO: 1 or 8;

According to another aspect of the present invention there is provided a method of increasing glucocerebrosidase activity in a cell, the method comprising exposing the cell to a glucocerebrosidase preparation comprising a population of glucocerebrosidase molecules, wherein substantially each of the glucocerebrosidase molecules: (i) has an amino acid sequence at least 95 percent homologous to an amino acid sequence set forth by SEQ ID NO: 1 or 8; (ii) is glycosylated at, or has an aspartatic acid residue at, glycosylation residue 1 of the amino acid sequence; and (iii) is independently unglycosylated at one or more glycosylation residues selected from the group consisting of glycosylation residues 2, 3 and 4 of the amino acid sequence, thereby inducing substantial glucocerebrosidase activity in a cell.

According to further features in preferred embodiments of the invention described below, exposing the cell to the glucocerebrosidase preparation is effected by administering the glucocerebrosidase preparation to a subject.

According to further features in preferred embodiments of the invention described below, exposing the cell to the glucocerebrosidase preparation is effected in-vitro.

According to still further features in the described preferred embodiments, the cell is a phagocyte.

According to yet another aspect of the present invention there is provided a method of treating a disease associated with glucocerebrosidase deficiency in a subject in need thereof, the method comprising administering to the subject in need thereof a therapeutically effective amount of a glucocerebrosidase preparation comprising a population of glucocerebrosidase molecules, wherein substantially each of the glucocerebrosidase molecules: (i) has an amino acid sequence at least 95 percent homologous to an amino acid sequence set forth by SEQ ID NO: 1 or 8; (ii) is glycosylated at, or has an aspartatic acid residue at, glycosylation residue 1 of the amino acid sequence; and (iii) is independently unglycosylated at one or more glycosylation residues selected from the group consisting of glycosylation residues 2, 3 and 4 of the amino acid sequence, thereby treating a disease associated with glucocerebrosidase deficiency in a subject in need thereof.

According to further features in preferred embodiments of the invention described below, administering to the subject in need thereof a therapeutically effective amount of a glucocerebrosidase preparation is effected via systemic administration.

According to still further features in the described preferred embodiments, the administering to the subject in need thereof a therapeutically effective amount of a glucocerebrosidase preparation is effected via local administration.

According to still another aspect of the present invention there is provided a pharmaceutical composition for treating a disease associated with glucocerebrosidase deficiency in a subject in need thereof, the pharmaceutical composition comprising a pharmaceutically acceptable carrier and, as an active ingredient, a glucocerebrosidase preparation comprising a population of glucocerebrosidase molecules, wherein substantially each of the glucocerebrosidase molecules: (i) has an amino acid sequence at least 95 percent homologous to an amino acid sequence set forth by SEQ ID NO: 1 or 8; (ii) is glycosylated at, or has an aspartatic acid residue at, glycosylation residue 1 of the amino acid sequence; and (iii) is independently unglycosylated at one or more glycosylation residues selected from the group consisting of glycosylation residues 2, 3 and 4 of the amino acid sequence.

According to further features in preferred embodiments of the invention described below, the pharmaceutically acceptable carrier is selected so as to enable administration of the pharmaceutical composition via a route selected from the group consisting of the intravenous, topical, intranasal, transdermal, intradermal, oral, buccal, parenteral, rectal and inhalation route.

According to a further aspect of the present invention there is provided an article of manufacture comprising packaging material and a pharmaceutical composition, the article of manufacture being identified for treatment of a disease associated with glucocerebrosidase deficiency in a subject in need thereof; the pharmaceutical composition comprising a pharmaceutically acceptable carrier and, as an active ingredient, a glucocerebrosidase preparation comprising a population of glucocerebrosidase molecules, wherein substantially each of the glucocerebrosidase molecules: (i) has an amino acid sequence at least 95 percent homologous to an amino acid sequence set forth by SEQ ID NO: 1 or 8; (ii) is glycosylated at, or has an aspartatic acid residue at, glycosylation residue 1 of the amino acid sequence; and (iii) is independently unglycosylated at one or more glycosylation residues selected from the group consisting of glycosylation residues 2, 3 and 4 of the amino acid sequence.

According to further features in preferred embodiments of the invention described below, the disease associated with glucocerebrosidase deficiency is Gaucher disease.

According to yet a further aspect of the present invention there is provided a glucocerebrosidase preparation comprising a population of glucocerebrosidase molecules, wherein substantially each of the glucocerebrosidase molecules: (i) has an amino acid sequence at least 95 percent homologous to an amino acid sequence set forth by SEQ ID NO: 1 or 8; (ii) is glycosylated at, or has an aspartatic acid residue at, glycosylation residue 1 of the amino acid sequence; and (iii) is independently unglycosylated at one or more glycosylation residues selected from the group consisting of glycosylation residues 2, 3 and 4 of the amino acid sequence.

According to further features in preferred embodiments of the invention described below, the glycosylation residue 1 is represented by Asn19 of SEQ ID NO: 1, 8 or 16.

According to still further features in the described preferred embodiments, the glycosylation residue 2 is represented by Asn59 of SEQ ID NO: 1, 8 or 16.

According to still further features in the described preferred embodiments, the glycosylation residue 3 is represented by Asn146 of SEQ ID NO: 1, 8 or 16.

According to still further features in the described preferred embodiments, the glycosylation residue 4 is represented by Asn270 of SEQ ID NO: 1, 8 or 16.

According to still further features in the described preferred embodiments, the population of glucocerebrosidase molecules, following an incubation in phosphate-buffered saline solution at a temperature of 25 degrees centigrade for a duration of at least 40 hours, has about the same capacity to catalyze hydrolysis of a glucocerebroside as a population of fully glycosylated glucocerebrosidase molecules each having an amino acid sequence selected from the group consisting of SEQ ID NO: 1 or 8.

According to still further features in the described preferred embodiments, the population of glucocerebrosidase molecules has about the same capacity to catalyze hydrolysis of a glucocerebroside as a population of fully glycosylated glucocerebrosidase molecules having an amino acid sequence selected from the group consisting of SEQ ID NO: 1 or 8.

According to still further features in the described preferred embodiments, at least one glycosylation moiety of each of at least some of the glucocerebrosidase molecules has at least one exposed mannose residue.

According to still further features in the described preferred embodiments, at least some of the glucocerebrosidase molecules are capable of being internalized by a phagocyte.

The present invention successfully addresses the shortcomings of the presently known configurations by providing: (i) a composition-of-matter comprising crystallized human glucocerebrosidase having an X-ray diffraction capacity enabling generation of structure coordinates defining the 3D structure of human glucocerebrosidase with optimal resolution; (ii) a method of generating such a composition-of-matter; (iii) a computing platform utilizing such structure coordinates for generating, at optimally high resolution, models representing the experimentally determined, essentially complete 3D structure of human glucocerebrosidase, including that of mutable portions thereof, and the predicted, essentially complete, 3D structure of mutant human glucocerebrosidase molecules, including that of mutant portions thereof; and (iv) methods of utilizing such structure coordinates for computationally identifying compounds capable of serving as optimal Gaucher disease drugs.

The present invention further successfully addresses the shortcomings of the presently known configurations by providing a glucocerebrosidase preparation comprising partially glycosylated glucocerebrosidase molecules, a pharmaceutical composition comprising such a preparation as an active ingredient and a pharmaceutically acceptable carrier, and an article of manufacture identified for treatment of a disease associated with glucocerebrosidase deficiency in a subject in need thereof comprising such pharmaceutical composition and packaging material, where such composition: (v) has about the same enzymatic activity as a preparation of fully glycosylated glucocerebrosidase molecules having an amino acid sequence set forth by SEQ ID NO: 1, 8 or 16; (vi) is significantly more enzymatically stable under physiological conditions than such a preparation of fully glycosylated glucocerebrosidase molecules; (vii) can be used for optimally increasing glucocerebrosidase activity in a cell; and (viii) can be used for optimally treating such a disease associated with glucocerebrosidase deficiency.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 6a-c depict partial deglycosylation of human glucocerebrosidase by N-glycosidase F. FIG. 6a is a photograph of a Coomassie blue-stained SDS-PAGE gel depicting the lower molecular weight of deglycosylated compared to non-deglycosylated glucocerebrosidase. FIGS. 6b-c are mass spectrometry data plots depicting the higher molecular weight of non-deglycosylated versus deglycosylated glucocerebrosidase, respectively.

FIGS. 8a and 8b are light photomicrographs respectively depicting macrophages exposed to fully glycosylated or partially glycosylated rhodamine-conjugated glucocerebrosidase, and FIGS. 8c and 8d are corresponding fluorescent photomicrographs of the macrophages shown in FIGS. 8a and 8b, respectively.

DESCRIPTION OF THE PREFERRED EMBODIMENTS

Figure 1A:
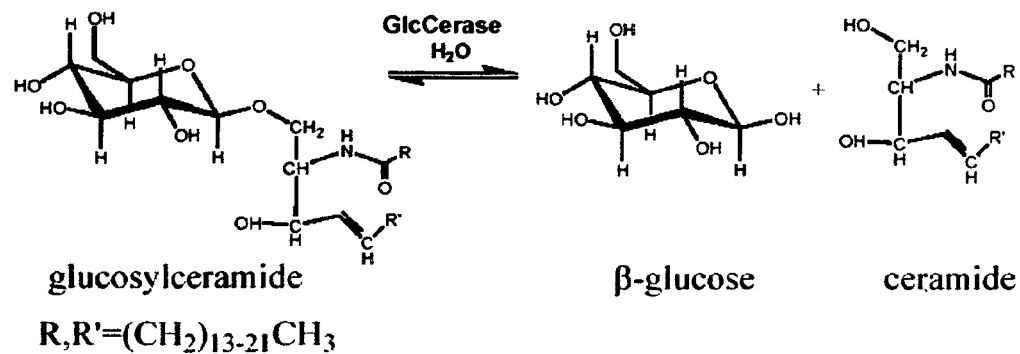
FIG. 1a is a prior art diagram depicting hydrolysis of the beta-glucosyl linkage of glucosylceramide by glucocerebrosidase in lysosomes to generate beta-glucose and ceramide.

The present invention is of a method of identifying a compound capable of correcting an impaired enzymatic activity of a mutant glucocerebrosidase molecule, a composition-of-matter comprising a crystallized glucocerebrosidase molecule having X-ray diffraction capacity enabling generation of structure coordinates defining a 3D structure of such a molecule or portion thereof, a method of generating such a crystallized molecule, a computing platform capable of generating a model representing a 3D structure of a glucocerebrosidase molecule or portion thereof, a computer-readable medium comprising, in a retrievable format, data including a set of structure coordinates defining such a structure, and a computer generated model representing such a structure. Specifically, the present invention can be used for identifying a compound capable of optimally correcting an impaired enzyme activity of a mutant glucocerebrosidase molecule associated with Gaucher disease, such compound having optimal physical, chemical, and/or biological characteristics for use as a drug. As such, the present invention can be used for identifying a Gaucher disease drug being markedly superior to all prior art Gaucher disease drugs. The present invention is further of preparations of partially glycosylated glucocerebrosidase molecules having about the same capacity to catalyze hydrolysis of a glucocerebroside as preparations of fully glycosylated glucocerebrosidase molecules, such as Cerezyme®, having optimal retention of such capacity under physiological conditions, and being capable of undergoing significant internalization/uptake by a phagocyte, such as a macrophage. The present invention is yet further of pharmaceutical compositions comprising as an active ingredient such partially glycosylated glucocerebrosidase molecule preparations, of articles of manufacture comprising such pharmaceutical compositions, and of methods of preparing such preparations. Such preparations of partially glycosylated glucocerebrosidase molecules can be used for optimally increasing glucocerebrosidase activity in a cell, such as a macrophage, under physiological conditions, and, as such, can be used for treating diseases associated with glucocerebrosidase deficiency, such as Gaucher disease, with optimal therapeutic efficacy, minimal drug administration, and optimal economy.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Gaucher disease is a devastating disorder resulting from impaired glucocerebrosidase enzymatic activity, and for which the main treatment, whole-enzyme replacement therapy with fully glycosylated glucocerebrosidase molecules, such as Cerezyme®, has numerous and significant drawbacks, as described above, including having suboptimal therapeutic effectiveness, requiring suboptimally high drug dosing regimens, being suboptimally economical, having harmful side-effects, and involving an undesirable preferred route of administration.

One approach for restoring defective enzymatic activity of a glucocerebrosidase mutant has been attempted in the prior art using deoxynijirimycin (DNJ)-based chemicals. Such an approach, however, suffers from the significant drawbacks of employing a type of compound having broadly non-specific inhibitory effects on numerous vital enzymes, of not having demonstrated effectiveness in correcting defective activity in numerous common glucocerebrosidase mutants, and of being potentially highly toxic.

Ideally, optimal Gaucher disease drugs could be computationally identified using sets of structure coordinates defining the 3D atomic structure of glucocerebrosidase. Such sets of structure coordinates could be used for computationally generating a model representing the predicted 3D structure of a human glucocerebrosidase mutant associated with Gaucher disease. Such models could in turn be used for computationally identifying a compound capable of optimally correcting a defective enzymatic activity of the mutant glucocerebrosidase molecule in-vivo.

Various approaches for obtaining sets of structure coordinates representing the 3D atomic structure of human glucocerebrosidase have been described by the prior art.

One such approach involves using two-dimensional hydrophobic cluster analysis in attempts to provide sets of structure coordinates defining predictive structures of human glucocerebrosidase molecules. Another approach involves crystallizing Cerezyme® and analyzing such crystals via X-ray crystallography in attempts to generate X-ray diffraction data defining 3D structures of Cerezyme®.

Such prior art approaches, however, have failed to provide a set of structure coordinates defining a 3D atomic structure of glucocerebrosidase or a portion thereof enabling computational identification of optimal Gaucher disease drugs.

Various partially glycosylated glucocerebrosidase preparations have been described in the prior art (as used herein, the phrase "partially glycosylated glucocerebrosidase" refers to glucocerebrosidase whose amino acid sequence includes at least one fully unglycosylated amino acid residue at a position corresponding to a glycosylated Asn residue).

One such approach involves individually or collectively replacing in human glucocerebrosidase via site-directed mutagenesis Asn residues which are glycosylated with a non-glycosylated amino acid residue to generate single point-mutant glucocerebrosidase preparations having individual glycosylated Asn residues mutated to non-glycosylated residues, or a quadruple point-mutant glucocerebrosidase preparation, having all four glycosylated Asn residues replaced with non-glycosylated residues. Another such approach involves sequentially deglycosylating porcine glucocerebrosidase with endoglycosidase H so as to obtain preparations of porcine glucocerebrosidase having only three, only two, or only one glycosylated Asn residues out of the four normally glycosylated Asn residues. Such prior art partially deglycosylated glucocerebrosidase preparations are suboptimal for treatment of a disease associated with glucocerebrosidase deficiency, such as Gaucher disease in humans, for various reasons, including: failure to generate a mutant glucocerebrosidase preparation demonstrably having either improved enzymatic activity, or improved stability of such activity under physiological conditions; failure to demonstrate that any of the preparations generated has any enzymatic activity; failure to characterize which Asn residues were deglycosylated in any of the preparations; and/or involve a glucocerebrosidase of porcine origin.

While reducing the present invention to practice, the present inventors succeeded in crystallizing a human glucocerebrosidase molecule having normal enzymatic activity of which crystallographic analysis was used for successfully generating for the first time a set of structure coordinates defining the essentially complete structure of the crystallized glucocerebrosidase molecule at atomic resolution. The present inventors further used this set of structure coordinates to generate for the first time sets of structure coordinates defining with optimally high resolution and accuracy essentially complete predicted 3D structures of mutant glucocerebrosidase molecules associated with Gaucher disease, including mutant portions thereof. While conceiving the present invention, the present inventors hypothesized that such sets of structure coordinates defining predicted 3D structures of mutant glucocerebrosidase molecules, in particular mutant portions thereof, could be used for identifying a compound capable of correcting in-vivo, with optimal efficacy and safety, the impaired enzymatic activity of a mutant glucocerebrosidase molecule associated with Gaucher disease.

Thus, according to the present invention there is provided a composition-of-matter comprising a crystallized glucocerebrosidase molecule having an X-ray diffraction capacity enabling generation of a set of structure coordinates defining a 3D structure of the glucocerebrosidase molecule or a portion thereof.

The composition-of-matter of the present invention can be used for generating for the first time a set of structure coordinates defining at atomic resolution an essentially complete 3D structure of a correctly folded glucocerebrosidase molecule, and in particular a portion thereof comprising an amino acid residue whose mutation may be associated with Gaucher disease (hereinafter referred to as "mutable portion"). Hence, as described hereinbelow, such a set of structure coordinates can be used for the first time for generating a computational model representing at atomic resolution a 3D structure of such a glucocerebrosidase molecule or a portion thereof. By using such a suitable computing platform, the data provided therein can be used for the first time for generating a set of structure coordinates defining, at atomic resolution and with optimal accuracy, an essentially complete predicted 3D structure of a glucocerebrosidase molecule having a mutated amino acid sequence associated with Gaucher disease (referred to hereinafter as "mutant glucocerebrosidase molecule"), or a portion thereof comprising a mutated amino acid residue associated with Gaucher disease (referred to hereinafter as "mutant portion"). The present inventors further hypothesized that such a computing platform could be used, preferably in conjunction with the set of structure coordinates defining the structure of the correctly folded glucocerebrosidase molecule, or a portion thereof, for computationally identifying a molecule capable of optimally correcting an impaired enzymatic activity of the mutant glucocerebrosidase molecule, and hence for identifying an optimal Gaucher disease drug.

Alternate art nomenclature for the chemical name "glucocerebrosidase" includes acid beta-glucosidase, D-glucosyl-N-acylsphingosine glucohydrolase, and glucosylceramidase. Gaucher disease may also be referred to in the art as glucosylceramide storage disease; GSDI)

As used herein, the phrase "3D structure" refers to the spatial positioning of a set of atoms, including a set of atoms which are not directly interconnected, and is used interchangeably with the phrase "three dimensional structure".

As used herein, an "essentially complete structure" of a glucocerebrosidase molecule or a portion thereof corresponds to a structure covering at least 95 percent of the complete structure of the glucocerebrosidase molecule or the portion thereof, respectively.

Preferably the crystallized glucocerebrosidase molecule of the present invention is essentially of mammalian origin, most preferably essentially of human origin.

The crystallized glucocerebrosidase molecule of the present invention may be characterized by:

(i) an X-ray diffraction capacity enabling generation of a set of structure coordinates defining a 3D structure of the crystallized glucocerebrosidase molecule or a portion thereof at any of various resolutions at least as high as 2.9 angstroms;

(ii) an X-ray diffraction capacity enabling generation of a set of structure coordinates defining an essentially complete 3D structure of the glucocerebrosidase molecule or essentially any portion thereof;

(iii) any of various unit cell dimensions;

(iv) any of various crystal space groups;

(v) a glucocerebrosidase molecule having any of various capacities to display enzymatic activity;

(vi) a glucocerebrosidase molecule having any of various amino acid sequences; and/or (vii) a glucocerebrosidase molecule having an amino acid sequence characterized by any of various glycosylation patterns.

As described hereinabove, the crystallized glucocerebrosidase molecule may be characterized by an X-ray diffraction capacity enabling generation of a set of structure coordinates defining a 3D structure of the glucocerebrosidase molecule or a portion thereof at any of various resolutions at least as high as 2.9 angstroms.

The crystallized glucocerebrosidase molecule preferably has an X-ray diffraction capacity enabling generation of a set of structure coordinates defining a 3D structure of the glucocerebrosidase molecule or a portion thereof at a resolution of 2.9 angstroms or higher, more preferably at a resolution of 2.8 angstroms or higher, more preferably at a resolution of 2.8 angstroms or higher, more preferably at a resolution of 2.7 angstroms or higher, more preferably at a resolution of 2.6 angstroms or higher, more preferably at a resolution of 2.5 angstroms or higher, more preferably at a resolution of 2.4 angstroms or higher, more preferably at a resolution of 2.3 angstroms or higher, more preferably at a resolution of 2.2 angstroms or higher, more preferably at a resolution of 2.1 angstroms or higher, and most preferably at a resolution of 2.0 angstroms.

As is described and illustrated in Example 1 of the Examples section below, the crystallized glucocerebrosidase molecule of the present invention has an X-ray diffraction capacity enabling for the first time generation of a set of structure coordinates defining an essentially complete 3D structure of the glucocerebrosidase molecule or essentially any portion thereof at a resolution of 2.0 angstroms. Such a set of structure coordinates of the present invention can be used for generating for the first time a model representing an essentially complete 3D atomic structure of a glucocerebrosidase molecule.

X-Ray Crystallography:

Utilizing an X-ray diffraction capacity of a crystallized molecule, such as that of an enzyme, for generating a set of structure coordinates defining a 3D structure of the crystallized molecule or a portion thereof is well within the purview of the ordinarily skilled artisan. The process of utilizing an X-ray diffraction capacity of a crystallized molecule, such as that of an enzyme, for generating a set of structure coordinates defining a 3D structure of the crystallized molecule or a portion thereof is referred to in the art as X-ray crystallography. X-ray crystallography is generally effected by exposing crystals to an X-ray beam and collecting the resultant X-ray diffraction data. This process usually involves the measurements of many tens of thousands of data points over a period of one to several days depending on the crystal form and the resolution of the data required. The crystals diffract the rays, creating a geometrically precise pattern of spots recorded on photographic film or electronic detectors. The distribution of atoms within the crystal influences the pattern of spots. The quality of protein crystals is determined by the ability of the crystal to scatter X-rays of wavelengths (typically 1.0-1.6 angstroms) suitable for determining the atomic coordinates of the macromolecule. The measure of the quality is determined as a function of the highest angle of scatter (the ultimate or intrinsic resolution) and according to Bragg's Law: $(n)(\lambda)=(2d)(\sin\theta)$, where $\theta$ is the angle of incidence of the reflected X-ray beam, d is the distance between atomic layers in a crystal, lambda is the wavelength of the incident X-ray beam, and n is an integer; d may be determined, and represents the resolution of the crystal form in angstroms. Thus, this measurement is routinely used to judge the ultimate usefulness of protein crystals. Group theory shows that there are 230 unique ways in which chemical substances, proteins or otherwise, may assemble in 3D to form crystals. These are called the 230 "space groups". The designation of the space group in addition to the unit cell constants (which define the explicit size and shape of the cell which repeats periodically within the crystal) is routinely used to uniquely identify a crystalline substance. Certain conventions have been established to ensure the proper identification of crystalline materials and these conventions have been set forth and documented in the International Tables for Crystallography, incorporated herein by reference.

While X-ray crystallography of a crystallized glucocerebrosidase molecule of the present invention may be effected in various ways, it is preferably effected according to the protocol set forth in Example 1 of the Examples section.

As described hereinabove, the crystallized glucocerebrosidase molecule of the present invention may be characterized by any of various unit cell dimensions.

Preferably, the crystallized glucocerebrosidase molecule of the present invention is characterized by unit cell dimensions of about a=about 107.7 angstroms, b=about 285.2 angstroms, and c=about 91.8.

As used herein the term "about" refers to ±10 percent.

As described hereinabove, the crystallized glucocerebrosidase molecule of the present invention may be characterized by any of various crystal space groups.

Preferably, the crystallized glucocerebrosidase molecule of the present invention is characterized by a crystal space group of $C222_1$.

As described hereinabove, the crystallized glucocerebrosidase molecule of the present invention may be capable of displaying any of various enzymatic activity levels.

Preferably, the crystallized glucocerebrosidase molecule of the present invention is capable of displaying normal enzymatic activity.

As used herein, the phrase "normal enzymatic activity" refers to a specific glucocerebrosidase enzymatic activity level normally displayed by a wild-type glucocerebrosidase molecule (having an amino acid sequence set forth by SEQ ID NO: 8). As is widely understood in the art glucocerebrosidase enzymatic activity is hydrolysis of the beta-glucosyl linkage of glucosylceramide (for example, refer to FIG. 1 of the Examples section for a schematic diagram depicting the enzymatic reaction) or of a synthetic beta-glucoside.

A specific glucocerebrosidase enzymatic activity level displayed by a wild-type glucocerebrosidase molecule will typically be:

(i) 2320-2560 nmol of the synthetic beta-glucoside 2-N-(NBD-dodecanoyl-)-sphingosyl-1-O-beta-glucoside hydrolyzed per hour per milligram of glucocerebrosidase, as determined according to "Method 1" set forth in Grabowski et al., 1986. 261:8263;

(ii) 2090-2178 nmol of the synthetic beta-glucoside 2-N-(NBD-dodecanoyl-)-sphingosyl-1-O-beta-glucoside hydrolyzed per hour per milligram of glucocerebrosidase, as determined according to "Method 2" set forth in Grabowski et al., 1986. 261:8263.

(iii) 2,790-3,610 nmol of the synthetic beta-glucoside 2-N-(NBD-hexanoyl-)-sphingosyl-1-O-beta-glucoside hydrolyzed per hour per milligram of glucocerebrosidase, as determined according to "Method 2" set forth in Grabowski et al., 1986. 261:8263;

(iv) 729-818 nmol of the synthetic beta-glucoside 4-methylumbelliferyl-11-O-beta-glucoside hydrolyzed per hour per milligram of glucocerebrosidase, as determined according to "Method 2" set forth in Grabowski et al., 1986. 261:8263;

(v) 1,973-2,460 nmol of the synthetic beta-glucoside 4-methylumbelliferyl-9-O-beta-glucoside hydrolyzed per hour per milligram of glucocerebrosidase, as determined according to "Method 2" set forth in Grabowski et al., 1986. 261:8263;

(vi) 1,820-2,124 nmol of the synthetic beta-glucoside 4-methylumbelliferyl-7-O-beta-glucoside hydrolyzed per hour per milligram of glucocerebrosidase, as determined according to "Method 2" set forth in Grabowski et al., 1986. 261:8263;

(vii) 2,240-2,280 nmol of the synthetic beta-glucoside 4-methylumbelliferyl-1-O-beta-glucoside hydrolyzed per hour per milligram of glucocerebrosidase, as determined according to "Method 1" set forth in Grabowski et al., 1986. 261:8263;

(viii) 2,038-2,430 nmol of the synthetic beta-glucoside 4-methylumbelliferyl-1-O-beta-glucoside hydrolyzed per hour per milligram of glucocerebrosidase, as determined according to "Method 2" set forth in Grabowski et al., 1986. 261:8263; and/or (ix) 830-1,000 nmol of the synthetic beta-glucoside 4-methylumbelliferyl-1-O-beta-glucoside hydrolyzed per hour per milligram of glucocerebrosidase, as determined according to "Method 1" set forth in Grabowski et al., 1986. 261:8263.

The above-described enzyme assay methods may be advantageously employed for measuring glucocerebrosidase enzymatic activity in various relevant contexts and applications of the present invention.

It will be appreciated that a normal glucocerebrosidase molecule of the present invention, by virtue of being capable of displaying normal enzymatic activity, will have normally folded 3D structure, in particular with respect to a portion thereof comprising an amino acid residue which, when mutated, alters glucocerebrosidase structure so as to lead to the glucocerebrosidase enzymatic activity deficiency associated with Gaucher disease.

Hence, it will be further appreciated that a normal glucocerebrosidase molecule of the present invention can be advantageously employed for generating a set of structure coordinates defining a 3D structure of a correctly folded glucocerebrosidase molecule, in particular of a correctly folded mutable portion thereof. By virtue of defining such correctly folded 3D structures, such a set of structure coordinates enables generation of a set of structure coordinates defining with optimal accuracy a predicted 3D structure of a mutant glucocerebrosidase molecule, or portion thereof, in particular of a mutant portion thereof.

As described hereinabove, a glucocerebrosidase molecule of the present invention may be characterized by having any of various amino acid sequences, including amino acid sequences displaying any of various partial glycosylation patterns.

Amino acid sequences of normal glucocerebrosidase molecules of the present invention are described hereinbelow.

The glucocerebrosidase molecule may be crystallized using any of various methods, according to the teachings of the present invention.

A glucocerebrosidase molecule of the present invention may be advantageously crystallized according to the method of crystallizing a glucocerebrosidase molecule of the present invention described hereinbelow.

As is described and illustrated in the Examples section below, the present invention provides a crystallized glucocerebrosidase molecule capable of displaying normal enzymatic activity characterized by: (i) an X-ray diffraction capacity enabling generation of a set of structure coordinates defining at 2.0 angstroms an essentially complete 3D structure thereof, including mutable portions thereof, (ii) unit cell dimensions of a=107.7 angstroms, b=285.2 angstroms, and c=91.8 angstroms; (iv) a crystal space group of C222$_1$; and (v) a partially glycosylated amino acid sequence.

As mentioned hereinabove, and as described and illustrated in the Examples section below, while reducing the present invention to practice, the present inventors used the crystallized glucocerebrosidase molecule of the present invention to generate for the first time a set of structure coordinates defining an essentially complete 3D structure thereof, including that of mutable portions thereof. This set of structure coordinates was used to generate for the first time a computational model representing at atomic resolution such structure. Crystal-derived data of normal and mutant glucocerebrosidase molecules can be used for the first time for computationally identifying a compound or compounds capable of correcting an impaired enzymatic activity of the mutant glucocerebrosidase molecule.

Thus, according to the present invention there is provided a method of identifying a compound capable of correcting an impaired enzymatic activity of a mutant glucocerebrosidase molecule. In a first step, the method is effected by obtaining a set of structure coordinates defining a 3D structure of a crystallized glucocerebrosidase molecule of the present invention capable of normal enzymatic activity, or a portion thereof. In a second step the set of structure coordinates defining the 3D structure of the normal glucocerebrosidase molecule is used to computationally generate a set of structure coordinates defining a predicted 3D structure of the mutant glucocerebrosidase molecule, or a portion thereof. In a third step, the set of structure coordinates defining the predicted 3D structure of the mutant glucocerebrosidase molecule, or portion thereof, is used to computationally identify a compound capable of interacting with the mutant glucocerebrosidase molecule in such a way as to correct the impaired enzymatic activity thereof.

It will be appreciated by one of ordinary skill in the art that a compound capable of interacting with a mutant glucocerebrosidase molecule in such a way as to correct the impaired enzymatic activity thereof, represents a potential Gaucher disease drug, and hence by virtue of enabling identification of such a compound, the method can thereby be used for identifying a candidate Gaucher disease drug.

Preferably, the step of computationally identifying the compound is effected further using the set of structure coordinates defining the 3D structure of the normal glucocerebrosidase molecule of the present invention or the portion thereof.

Following computational identification thereof, the capacity of the compound to correct the impaired enzymatic activity of the mutant glucocerebrosidase molecule is preferably biochemically qualified.

Obtaining the set of structure coordinates defining the 3D structure of the normal glucocerebrosidase molecule or portion thereof may be effected in various ways.

Preferably, the set of structure coordinates is obtained by subjecting the crystallized glucocerebrosidase molecule of the present invention to crystallographic analysis, as described hereinabove.

Computationally generating the set of structure coordinates defining the predicted 3D structure of the mutant glucocerebrosidase capable of normal molecule, or portion thereof, may be performed in various ways. Preferably, such a set of coordinates is computationally generated according to the method set forth in the Examples section below. Ample guidance for computationally generating such a set of coordinates is provided in the literature of the art, as extensively described hereinbelow.

According to the teachings of the present invention, computationally generating the set of structure coordinates defining the predicted 3D structure of the mutant glucocerebrosidase molecule or portion thereof, is achieved by using as a computationally modified template structure a set of structure coordinates defining a 3D structure of a mutable portion of a normal glucocerebrosidase molecule corresponding to a mutant portion of the mutant glucocerebrosidase molecule. It will be appreciated that since the set of structure coordinates defining a 3D structure of a mutable portion of a normal glucocerebrosidase molecule of the present invention defines an experimentally determined, and hence accurate, 3D atomic structure of the mutable portion of the normal glucocerebrosidase molecule, such a set of coordinates can be utilized for generating a set of structure coordinates defining an optimally accurate 3D atomic structure of a mutant glucocerebrosidase molecule of the present invention.

As described hereinbelow, according to the teachings of the present invention a mutable portion of a normal glucocerebrosidase molecule and a mutant portion of a mutant glucocerebrosidase molecule which correspond to each other preferably comprise sets of amino acid residues which substantially differ from each other only with respect to amino acid residues associated with the impaired glucocerebrosidase enzymatic activity of the mutant glucocerebrosidase molecule. Preferably, such difference will correspond to a single amino acid substitution in the amino acid sequence of the mutant portion of the mutant glucocerebrosidase molecule relative to the amino acid sequence of the mutable portion of the normal glucocerebrosidase molecule, as described hereinbelow.

The step of using the set of structure coordinates for computationally identifying the compound of the present invention may be effected in various ways. The use of sets of structure coordinates for computationally identifying a compound capable of exerting a desired effect on the functionality of a target enzyme, such as a mutant glucocerebrosidase molecule of the present invention is widely practiced in the art and ample guidance for practicing such computational identification is provided in the literature of the art, as extensively described hereinbelow.

Preferably, computationally identifying the compound of the present invention is effected by computationally qualifying the capacity of a candidate compound to interact with the mutant portion of the mutant glucocerebrosidase molecule, in such a way as to: (i) alter the 3D structure of the mutant portion of the mutant glucocerebrosidase molecule to assume a 3D structure maximally similar to that of the mutable portion of the normal glucocerebrosidase molecule; or (ii) form a complex with the mutant portion of the mutant glucocerebrosidase molecule having a resultant 3D structure maximally similar to that of the mutable portion of the normal glucocerebrosidase molecule. Preferably, in order to optimally computationally qualify the 3D structure of the mutant portion of the glucocerebrosidase molecule, or of a complex thereof with the compound, following interaction of the mutant glucocerebrosidase molecule with the compound, such computational qualifying preferably further comprises using the set of coordinates defining the 3D structure of the mutable portion of the normal glucocerebrosidase molecule as a reference structure to which a 3D structure of the mutant portion of the glucocerebrosidase molecule, or of a complex thereof with the compound, resulting from interaction of the mutant glucocerebrosidase molecule with the compound is compared.

Preferably, the above-described computational processes are reiterated so as to screen a computational library of candidate compound 3D structures so as to identify a compound which interacts with the mutant glucocerebrosidase molecule or mutant portion thereof in such a way as to optimally correct the 3D structure of the mutant glucocerebrosidase molecule or mutant portion thereof, or in such a way as to generate a complex of the compound with the mutant glucocerebrosidase molecule or mutant portion thereof having a desired glucocerebrosidase enzymatic activity when combined. It will be appreciated that a mutant glucocerebrosidase molecule having a mutant portion whose 3D structure, or of a complex thereof with the compound, is substantially similar to that of the mutable portion of the normal glucocerebrosidase molecule as a result of interacting with the compound will be capable of displaying an increased enzymatic activity relative to such activity in the absence of the compound.

As described hereinabove, since the present invention provides a set of structure coordinates defining at atomic resolution an essentially complete 3D structure of a normal glucocerebrosidase molecule, in particular that of a mutable portion thereof, the method can be used for generating a set of structure coordinates defining with optimal resolution and accuracy a predicted 3D structure of essentially any mutable portion of the normal glucocerebrosidase molecule. It will be appreciated that a set of structure coordinates defining a predicted 3D structure of essentially any mutable portion of a normal glucocerebrosidase molecule can be used for optimally qualifying a capacity of a candidate compound to interact with a mutant portion of a mutant glucocerebrosidase molecule in such a way as to correct a 3D structure of a mutant portion thereof, and hence for optimally correcting the impaired enzymatic activity of the mutant glucocerebrosidase molecule. Hence, as described hereinbelow, the method of identifying the compound of the present invention can be used for identifying an optimal Gaucher disease drug.

Depending on the desired mutant glucocerebrosidase molecule specificity of the compound of the present invention, the mutant glucocerebrosidase molecule may have any of various amino acid sequences. Preferably, the mutant glucocerebrosidase molecule comprises a mutant portion corresponding to the desired mutant glucocerebrosidase molecule specificity of the compound of the present invention.

Amino acid sequences of mutant glucocerebrosidase molecules of the present invention, and specific applications thereof are described hereinbelow.

It will be appreciated that by virtue of enabling computational screening of libraries of compounds having essentially any of various chemical, biological and/or physical characteristics, the method enables identification of a compound capable of displaying optimal in-vivo pharmacokinetics, optimally low immunogenicity, and optimal effectiveness relative to all prior art compounds capable of correcting impaired glucocerebrosidase enzymatic activity of a mutant glucocerebrosidase molecule, such as DNJ-based compounds, or prior art compounds capable of providing exogenous glucocerebrosidase activity, such as Cerezyme®. Hence, the method can be utilized to identify an optimal Gaucher disease drug.

For optimal effectiveness as a Gaucher disease drug in-vivo, the compound of the present invention should be as small as possible while still being capable of correcting the impaired enzymatic activity of the mutant glucocerebrosidase molecule since, keeping all other parameters equal, the smaller a molecule, the better its overall biodistribution capacity will generally be. An optimally small compound of the present invention will circumvent the limitations of prior art Gaucher disease drugs such as Cerezyme® whose active ingredient is a full-sized protein.

The molecule is preferably a non-polypeptidic compound. A non-polypeptidic compound will avoid the immunogenicity drawbacks of prior art Gaucher disease drugs such as Cerezyme® whose active ingredient is a protein.

It will be appreciated that, by virtue of its capacity for correcting impaired endogenous glucocerebrosidase activity, the compound of the present invention is distinctly advantageous over prior art Gaucher disease drugs since, unlike prior art compounds such as Cerezyme®, it affords therapeutic glucocerebrosidase activity with optimal spatial (cell type/subcellular location), temporal, and activity level regulation. Evidence for the feasibility of using a compound for correcting an impaired enzymatic activity of a mutant glucocerebrosidase molecule associated with Gaucher disease has been provided in the prior art (Leslie A G W., 1992. Newsletter on Protein Crystallography 26). Examples of suitable chemical structure databases for performing the above-described screening are described hereinbelow.

The compound of the present invention can be used per se or it can be formulated as the active ingredient of a pharmaceutical composition comprising suitable carriers and/or diluents, and an effective concentration of the compound of the present invention so as to be suitable for therapeutically correcting the impaired enzymatic activity of the mutant glucocerebrosidase molecule when administered to a subject in need thereof, in particular a subject having Gaucher disease.

One of ordinary skill in the art, such as for example, a pharmacologist, a veterinarian, or a physician would possess the expertise required for correctly formulating such a pharmaceutical composition for effective disease treatment.

Biochemical Qualification of the Capacity of the Compound to Correct the Impaired Enzymatic Activity of the Mutant Glucocerebrosidase Molecule:

As described hereinabove, following computational identification thereof, the capacity of the compound to correct the impaired enzymatic activity of the mutant glucocerebrosidase molecule is preferably biochemically qualified.

Preferably, biochemically qualifying the capacity of the compound to correct the impaired enzymatic activity of the mutant glucocerebrosidase molecule is effected by measuring the specific glucocerebrosidase enzymatic activity of the mutant glucocerebrosidase molecule in the absence or presence of the compound using a standard glucocerebrosidase activity assay. A compound identified capable of increasing, or optimally increasing, the specific glucocerebrosidase enzymatic activity of the mutant glucocerebrosidase molecule constitutes a candidate Gaucher disease drug, or a candidate optimal Gaucher disease drug, respectively. The specific enzymatic activity of the mutant glucocerebrosidase molecule may be advantageously measured in the presence of varying concentrations of the compound so as to enable identification of concentrations of the compound needed for increasing the specific enzymatic activity of the mutant glucocerebrosidase molecule to an optimal level.

Any of various glucocerebrosidase enzymatic activity assays may be employed.

For example, the specific glucocerebrosidase enzymatic activity of the mutant glucocerebrosidase molecule may be determined using an enzyme assay using as an enzyme substrate either glucosylceramidase, the natural substrate of glucocerebrosidase, or a synthetic glucocerebrosidase substrate, preferably a synthetic beta-glycoside substrate of glucocerebrosidase. Ample art guidance for practicing such methods is provided hereinabove.

Preferably, the compound of the present invention is selected capable of sufficiently correcting the impaired enzymatic activity of the mutant glucocerebrosidase molecule so as to have utility for treating Gaucher disease. Ample guidance regarding normal glucocerebrosidase enzymatic activity levels is provided hereinabove.

As described hereinabove, while reducing the present invention to practice the present inventors produced a computing platform capable of generating a model representing an essentially complete 3D atomic structure of a glucocerebrosidase molecule.

Thus, according to still another aspect of the present invention there is provided a computing platform capable of generating a model representing a 3D structure of a glucocerebrosidase molecule or a portion thereof. The computing platform comprises a data-storage device storing data comprising a set of structure coordinates defining the 3D structure of the glucocerebrosidase molecule or the portion thereof. The computing platform further comprises a processing unit for generating the model representing the 3D structure from the data stored in the data-storage device.

Examples of suitable platforms and software applications for running such platforms are provided hereinbelow.

The computing platform of the present invention can be exploited in various ways.

As described hereinabove, the computing platform of the present invention can be used as described hereinabove for identifying a compound capable of optimally correcting an impaired enzymatic activity of essentially any mutant glucocerebrosidase molecule, and hence for identifying a candidate Gaucher disease drug. It will be appreciated that the computing platform can further be used for optimally elucidating the structural and functional characteristics of normal and mutant glucocerebrosidase molecules, and thereby for generating novel information having significant utility in fields such as medical diagnostics, therapeutics, pharmacology, and applied research. This is abundantly demonstrated by the wealth of novel structural/functional features of normal and mutant glucocerebrosidase molecules which can now be described for the first time using the computing platform of the present invention.

Depending on the application and purpose, the computing platform may be capable of generating a model representing a 3D structure of essentially any normal glucocerebrosidase molecule or portion thereof and/or may be capable of generating a model representing a 3D structure of essentially any mutant glucocerebrosidase molecule or portion thereof.

Normal glucocerebrosidase molecules and mutant glucocerebrosidase molecules of the present invention are described hereinbelow.

Preferably, a computing platform capable of generating a model representing a 3D structure of a portion of a normal glucocerebrosidase molecule of the present invention is capable of generating a model representing a 3D structure of a mutable portion of a normal glucocerebrosidase molecule of the present invention.

Preferably, a computing platform capable of generating a model representing a 3D structure of a portion of a mutant glucocerebrosidase molecule of the present invention is capable of generating a model representing a 3D structure of a mutant portion of a mutable glucocerebrosidase molecule of the present invention.

As described hereinabove, a computing platform capable of generating a model representing a 3D structure of a mutable portion of a normal glucocerebrosidase molecule of the present invention can be used for computationally generating a set of structure coordinates defining a predicted 3D structure of a mutant glucocerebrosidase of the present invention, and for facilitating computational identification of the compound of the present invention.

As described hereinabove, a computing platform capable of generating a model representing a 3D structure of a mutant portion of a mutant glucocerebrosidase molecule of the present invention can be used for identifying the compound of the present invention.

Amino Acid Sequence of Normal Glucocerebrosidase Molecule of Present Invention:

As described hereinabove, a normal glucocerebrosidase molecule of the present invention may have any of various amino acid sequences, and thereby may comprise any of various mutable portions, depending on the application and purpose.

The glucocerebrosidase molecule of the present invention may be characterized by a wild-type amino acid sequence (SEQ ID NO: 8), or by an amino acid sequence in which Arg495 of the wild-type amino acid sequence is substituted with a His residue (SEQ ID NO: 1).

Preferably, the amino acid sequence of the normal glucocerebrosidase molecule of the present invention is composed of 497 amino acid residues.

Preferably, the amino acid sequence of a normal glucocerebrosidase molecule of the present invention is set forth in SEQ ID NO: 1.

A glucocerebrosidase molecule having the amino acid sequence set forth in SEQ ID NO: 1 is widely understood in the art as being capable of displaying wild-type enzymatic activity. For example, as described above, the standard treatment for Gaucher disease is enzyme replacement therapy with the commercial drug Cerezyme® (Genzyme Corporation, Cambridge, Mass., USA) whose active ingredient is a variant of human glucocerebrosidase having the amino acid sequence set forth in SEQ ID NO: 1, and exhibiting an enzymatic activity identical to that of wild-type human glucocerebrosidase (for example, refer to Grabowski G A. et al., 1995. Ann Intern Med. 122:33-9). Substitution of Arg495 to His in Cerezyme® has been documented not to affect the catalytic functions, safety or therapeutic effectiveness of Cerezyme (Genzyme Corporation, on file; Grabowski et al., 1995. Ann Intern Med. 122: 33-39; Grace et al., 1993. J Biol Chem. 265:2283-2291).

Hence, it will be appreciated that a 3D structure of Cerezyme® is essentially identical to that of wild-type human glucocerebrosidase, in particular with respect to mutable portions thereof.

Portion of Normal Glucocerebrosidase Molecule of Present Invention:

As described hereinabove, a normal glucocerebrosidase molecule of the present invention may be characterized by any of various portions depending on the application and purpose.

Preferably, a portion of a normal glucocerebrosidase molecule comprises a set of amino acid residues of the amino acid sequence of the normal glucocerebrosidase molecule having at least one atom positioned within 10 angstroms of at least one atom of a reference amino acid residue of the normal glucocerebrosidase molecule, as described in Example 2 of the Examples section below.

Preferably, a mutable portion of a normal glucocerebrosidase molecule of the present invention having an amino acid sequence composed of 497 amino acid residues comprises an amino acid residue located at position 370, 394, 409, 444, 463, and/or 496 of the amino acid sequence of the normal glucocerebrosidase molecule.

As described in the Examples section below, mutation of an amino acid residue located at position 370, 394, 409, 444, 463, or 496 of the amino acid sequence of a glucocerebrosidase molecule, such as a glucocerebrosidase molecule having the amino acid sequence set forth in SEQ ID NO: 1 or 8, in particular a mutation characterized by a Ser residue at position 370, a Leu residue at position 394, a His residue at position 409, a Pro residue at position 444, or a His residue at position 496, is associated with one of the most common forms of Gaucher disease.

Preferably, the mutable portion comprising the amino acid residue at position 370 of the amino acid sequence of the normal glucocerebrosidase molecule comprises the amino acid residues at positions 76, 81, 285, 312, 314, 320, 324, 325, 336, 364-378, 423, and 433 of the amino acid sequence of the normal glucocerebrosidase molecule.

Preferably, the mutable portion comprising the amino acid residue at position 394 of the amino acid sequence of the normal glucocerebrosidase molecule comprises the amino acid residues at positions 244-247, and 390-397 of the amino acid sequence of the normal glucocerebrosidase molecule.

Preferably, the mutable portion comprising the amino acid residue at position 409 of the amino acid sequence of the normal glucocerebrosidase molecule comprises the amino acid residues at positions 20, 21, 95-100, and 404-411 of the amino acid sequence of the normal glucocerebrosidase molecule.

Preferably, the mutable portion comprising the amino acid residue at position 444 of the amino acid sequence of the normal glucocerebrosidase molecule comprises the amino acid residues at positions 65-67, 440-447, 460-464, 468, and 469 of the amino acid sequence of the normal glucocerebrosidase molecule.

Preferably, the mutable portion comprising the amino acid residue at position 463 of the amino acid sequence of the normal glucocerebrosidase molecule comprises the amino acid residues at positions 360-366, 443-446, 460-467, and 484-89 of the amino acid sequence of the normal glucocerebrosidase molecule.

Preferably, the mutable portion comprising the amino acid residue at position 496 of the amino acid sequence of the normal glucocerebrosidase molecule comprises the amino acid residues at positions 33-35, 69, 71, 450-456, 474-478, and 493-497 of the amino acid sequence of the normal glucocerebrosidase molecule.

3D Structure of Normal Glucocerebrosidase Molecule of Present Invention:

As is described hereinabove, a normal glucocerebrosidase molecule of the present invention, or a portion thereof, may be characterized by any of various 3D structures, depending on the application and purpose.

Preferably, the normal glucocerebrosidase molecule of the present invention is characterized by a 3D structure defined by the set of structure coordinates set forth in Table 4.

Refer to enclosed CD-ROM for Tables 4-22.

As is described in the Examples section which follows, the two sets of structure coordinates corresponding to atom coordinates 1-3929 and 3930-7859 set forth in Table 4 define at atomic resolution two essentially complete, and essentially identical, 3D structures of two distinct co-crystallized glucocerebrosidase molecules of the present invention capable of normal enzymatic activity. As is described in Example 1 of the Examples section which follows, these two structures represent the structures of the two monomers forming the asymmetric unit of crystallized glucocerebrosidase molecules of the present invention capable of normal enzymatic activity generated while reducing the present invention to practice.

While a normal glucocerebrosidase molecule of the present invention whose 3D structure is defined by a set of structure coordinates set forth in Table 4 may have a 3D structure defined by either the set of structure coordinates corresponding to atom coordinates 1-3929 or the set of structure coordinates corresponding to atom coordinates 3930-7859 set forth in Table 4, its 3D structure is preferably defined by the set of structure coordinates corresponding to atom coordinates 1-3929 set forth in Table 4.

As is described and illustrated in Example 1 of the Examples section which follows, the set of structure coordinates corresponding to atom coordinates 1-3929 set forth in Table 4 defines an essentially complete 3D atomic structure of a normal glucocerebrosidase molecule of the present invention.

Hence, as described hereinabove, the set of structure coordinates set forth in Table 4 can be utilized for generating a model representing a 3D structure of a normal glucocerebrosidase molecule of the present invention, or a portion thereof.

3D Structure of Portion of Normal Glucocerebrosidase Molecule of the Present Invention:

As described hereinabove, a portion of a normal glucocerebrosidase molecule of the present invention may be characterized by any of various 3D structures.

Preferably, a mutable portion of a normal glucocerebrosidase molecule of the present invention whose structure is set forth in Table 4 has a 3D structure defined by the set of structure coordinates set forth in Table 5, 6, 7, 8, 9, and/or 10.

As is described and illustrated in Example 2 of the Examples section which follows, the set of structure coordinates set forth in Table 5 defines a 3D structure of a mutable portion of a normal glucocerebrosidase molecule of the present invention having an amino acid sequence composed of 497 amino acid residues where such portion comprises amino acid residues at positions 76, 81, 285, 312, 314, 320, 324, 325, 336, 364-378, 423, and 433 of the amino acid sequence of the normal glucocerebrosidase molecule. Hence, as described hereinbelow, this set of structure coordinates can be utilized for generating a computational model representing at atomic resolution an essentially complete 3D structure of such a portion of such a glucocerebrosidase molecule.

As is described and illustrated in Example 2 of the Examples section which follows, the set of structure coordinates set forth in Table 6 defines at optimally high resolution an essentially complete 3D structure of a portion of a normal glucocerebrosidase molecule of the present invention having an amino acid sequence composed of 497 amino acid residues where such portion comprises amino acid residues at positions 244-247, and 390-397 of the amino acid sequence of the normal glucocerebrosidase molecule. Hence, as described hereinbelow, this set of structure coordinates can be utilized for generating a computational model representing at atomic resolution an essentially complete 3D structure of such a portion of such a glucocerebrosidase molecule.

As is described and illustrated in Example 2 of the Examples section which follows, the set of structure coordinates set forth in Table 7 defines at optimally high resolution an essentially complete 3D structure of a portion of a normal glucocerebrosidase molecule of the present invention having an amino acid sequence composed of 497 amino acid residues where such portion comprises amino acid residues at positions 20, 21, 95-100, and 404-411 of the amino acid sequence of the normal glucocerebrosidase molecule. Hence, as described hereinbelow, this set of structure coordinates can be utilized for generating a computational model representing at atomic resolution an essentially complete 3D structure of such a portion of such a glucocerebrosidase molecule.

As is described and illustrated in Example 2 of the Examples section which follows, the set of structure coordinates set forth in Table 8 defines at optimally high resolution an essentially complete 3D structure of a portion of a normal glucocerebrosidase molecule of the present invention having an amino acid sequence composed of 497 amino acid residues where such portion comprises amino acid residues at positions 65-67, 440-447, 460-464, 468, and 469 of the amino acid sequence of the normal glucocerebrosidase molecule. Hence, as described hereinbelow, this set of structure coordinates can be utilized for generating a computational model representing at atomic resolution an essentially complete 3D structure of such a portion of such a glucocerebrosidase molecule.

As is described and illustrated in Example 2 of the Examples section which follows, the set of structure coordinates set forth in Table 9 defines at optimally high resolution an essentially complete 3D structure of a portion of a normal glucocerebrosidase molecule of the present invention having an amino acid sequence composed of 497 amino acid residues where such portion comprises amino acid residues at positions 360-366, 443-446, 460-467, and 484-89 of the amino acid sequence of the normal glucocerebrosidase molecule. Hence, as described hereinbelow, this set of structure coordinates can be utilized for generating a computational model representing at atomic resolution an essentially complete 3D structure of such a portion of such a glucocerebrosidase molecule.

As is described and illustrated in Example 2 of the Examples section which follows, the set of structure coordinates set forth in Table 10 defines at optimally high resolution an essentially complete 3D structure of a portion of a normal glucocerebrosidase molecule of the present invention having an amino acid sequence composed of 497 amino acid residues where such portion comprises amino acid residues at positions 33-35, 69, 71, 450-456, 474-478, and 493-497 of the amino acid sequence of the normal glucocerebrosidase molecule. Hence, as described hereinbelow, this set of structure coordinates can be utilized for generating a computational model representing at atomic resolution an essentially complete 3D structure of such a portion of such a glucocerebrosidase molecule.

It will be appreciated that mutant glucocerebrosidase molecules having amino acid sequences composed of 497 amino acid residues where such portions have a Ser residue at position 370, a Leu residue at position 394, a His residue at position 409, a Pro residue at position 444, and/or a His residue at position 496 of such amino acid sequences represent the most common mutant glucocerebrosidase molecules associated with Gaucher disease (refer, for example, to Table 3 of the Examples section). It will be further appreciated that the sets of structure coordinates set forth in Tables 5-10 define at atomic resolution essentially complete 3D structures of mutable portions of a normal glucocerebrosidase molecule having an amino acid sequence composed of 497 amino acid residues where such portions comprise the amino acid residue located at position 370, 394, 409, 444, 463, or 496 of the amino acid sequence of such a glucocerebrosidase molecule, respectively. Hence, the set of structure coordinates set forth in Tables 5-10 can respectively be used for the first time for generating computing platforms capable of generating models representing at atomic resolution essentially complete 3D structures of mutable portions comprising amino acid residues located at position 370, 394, 409, 444, 463, and/or 496 of the amino acid sequence of such a normal glucocerebrosidase molecule. As such, as described hereinbelow and in the Examples section below, the set of structure coordinates set forth in Tables 5-10 can be used for the first time for facilitating computational identification of drugs optimally suitable for treating the most prevalent forms of Gaucher disease.

Amino Acid Sequence of Mutant Glucocerebrosidase Molecule of Present Invention:

As described hereinabove, a mutant glucocerebrosidase molecule of the present invention may have any of various amino acid sequences.

Preferably, the amino acid sequence of the mutant glucocerebrosidase molecule is composed of 497 amino acid residues.

Preferably, the amino acid sequence of the glucocerebrosidase molecule is set forth in SEQ ID NO: 2, 3, 4, 5, 6, or 7, depending on the mutant glucocerebrosidase molecule of the present invention of interest.

It will be appreciated that the amino acid sequences set forth in SEQ ID NOs: 2-7 are the amino acid sequences of mutant glucocerebrosidase molecules having an amino acid sequence composed of 497 amino acid residues having an amino acid sequence comprising the mutant amino acid residue Ser at position 370, Leu at position 394, His at position 409, Pro at position 444, and His at position 496, respectively. As described hereinabove, such residues at such positions correspond to the most common single amino acid substitution mutations associated with Gaucher disease.

Alternately, the mutant glucocerebrosidase of the present invention may have the amino acid sequence set forth in SEQ ID NO: 9, 10, 11, 12, 13, or 14.

It will be appreciated that the amino acid sequences set forth in SEQ ID NOs: 9-14 are the amino acid sequences of naturally occurring mutant glucocerebrosidase molecules comprising the mutated amino acid residue Ser at position 370, Leu at position 394, His at position 409, Pro at position 444, and His at position 496, respectively, and that, as described hereinabove, such mutant glucocerebrosidase molecules comprise the single amino acid substitution mutations most commonly associated with Gaucher disease.

Figure 1B:
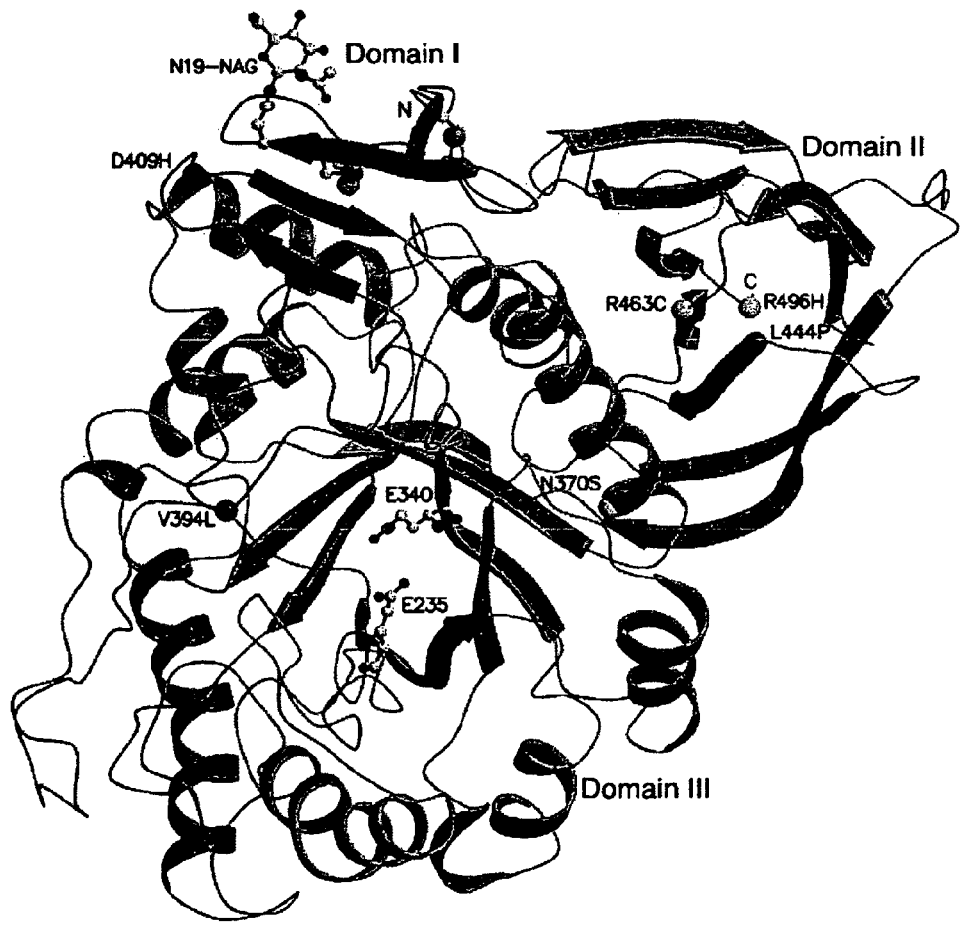
FIG. 1b is a 3D structure diagram depicting the 2.0 angstrom atomic 3D structure of a human glucocerebrosidase molecule capable of displaying normal enzymatic activity. Domain I is shown in magenta and contains the 2 disulfide bridges, whose S-atoms are shown as green balls. The glycosylation site at Asn19 (N19) is depicted as balls and sticks. Domain II, an Ig-like domain, is shown in green. The catalytic domain (domain III), a TIM barrel, is shown in cyan, and the active site residues E235 and E340 shown as balls and sticks. The six most common glucocerebrosidase mutations are shown as balls, with those that predispose to severe (i.e., Type 2 or 3) and mild (i.e., Type 1) disease in red and yellow, respectively.
Figure 1C:
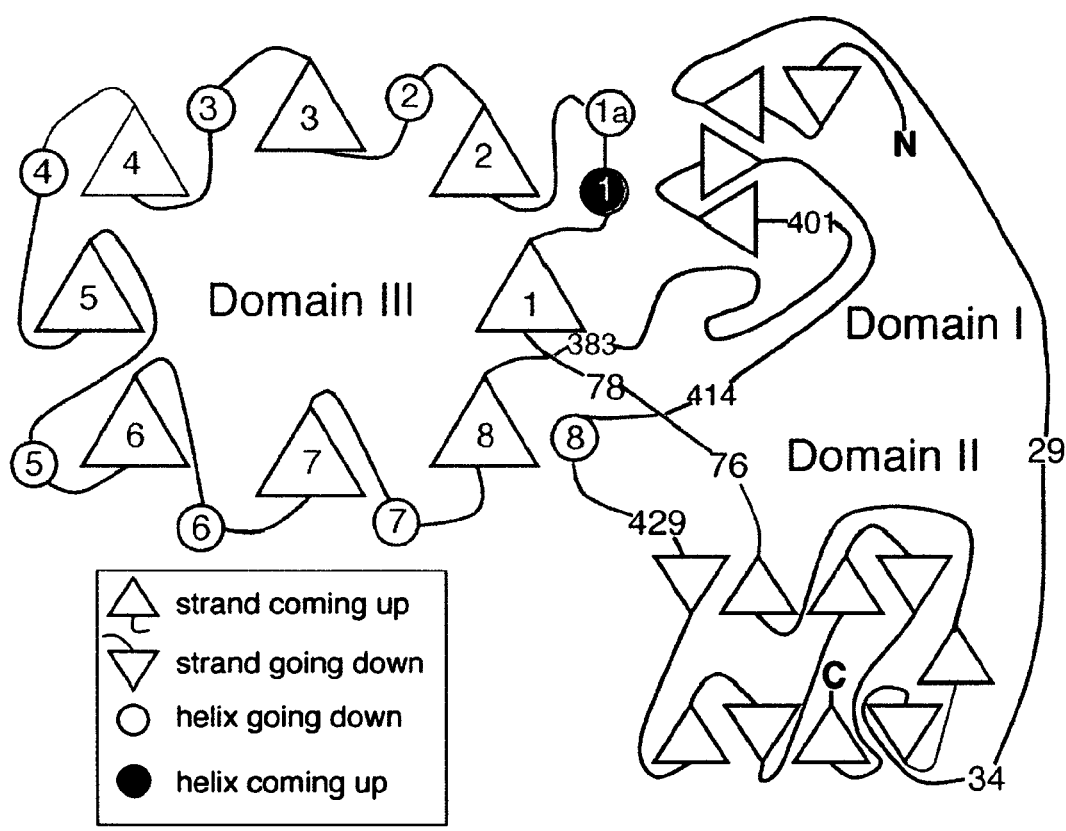
FIG. 1c is a 2D topology diagram depicting the 2D topology map of the structure of a human glucocerebrosidase molecule capable of displaying normal enzymatic activity. The diagram is consistent with a 3D-view looking down the opening of the active site pocket, as in panel A. All connecting loops in the diagram are of arbitrary length. Alpha-helices and beta-strands of Domain III are numbered according to their position in the sequence. For clarity, sequence coordinates for certain key positions are shown in the connecting loops, and secondary elements four residues or smaller are not shown.
Figure 1D:
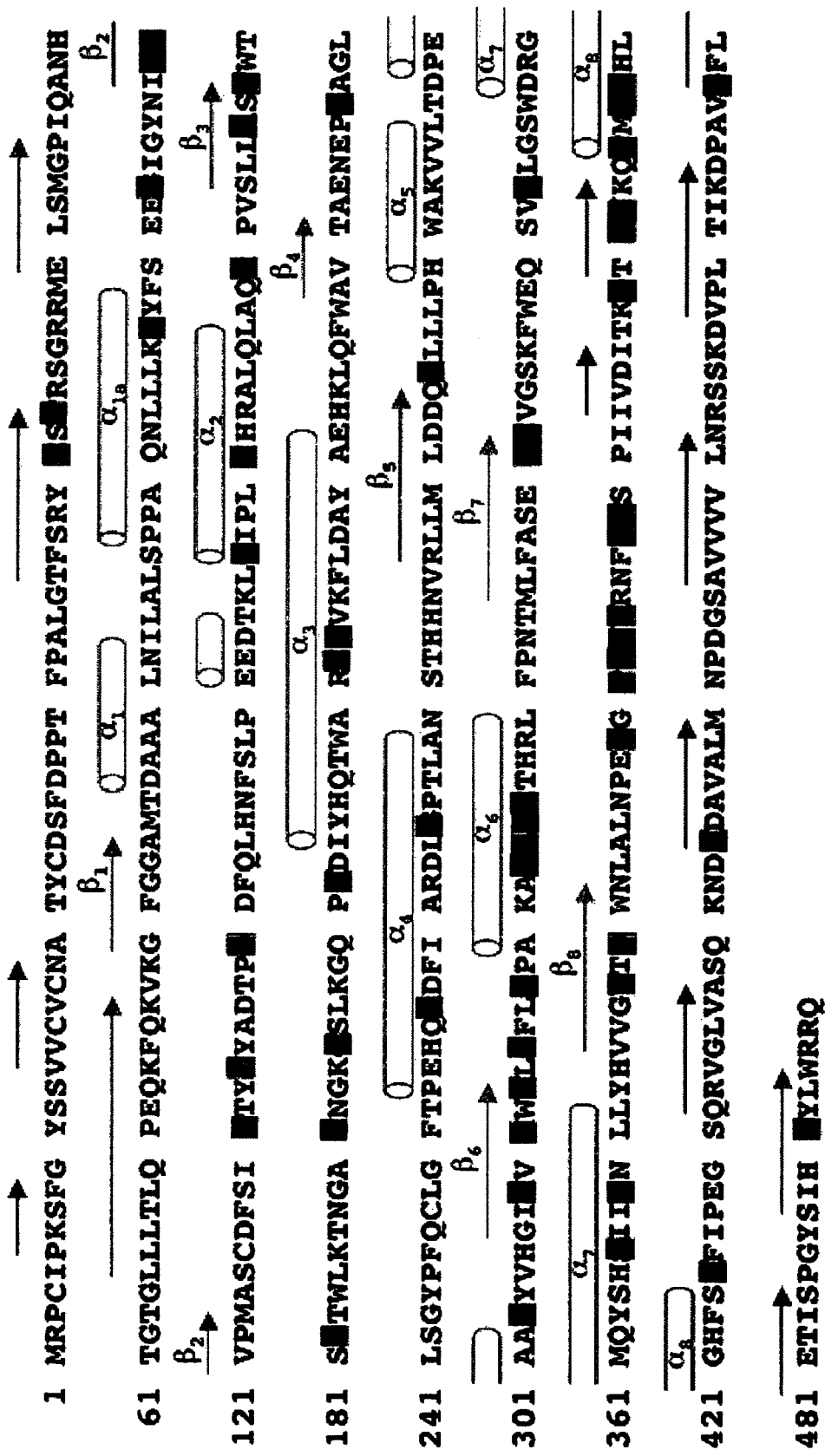
FIG. 1d is a sequence diagram depicting the primary amino acid sequence of the 497 amino acid residues of human glucocerebrosidase with normal enzymatic activity (SEQ ID NO: 8), showing the amino acid positions thereof associated with pathological effects. Positions of mutations associated with severe disease are shown in red, mild disease in yellow, and those for which clinical data documenting disease severity are lacking, in blue. Only single amino acid substitutions are included, with frameshifts and splices excluded as enzyme is not expressed in most of these cases. Helices are indicated by cylinders and beta-strands by arrows and colored according the domains as shown in FIG. 1b, above.
Figure 1E:
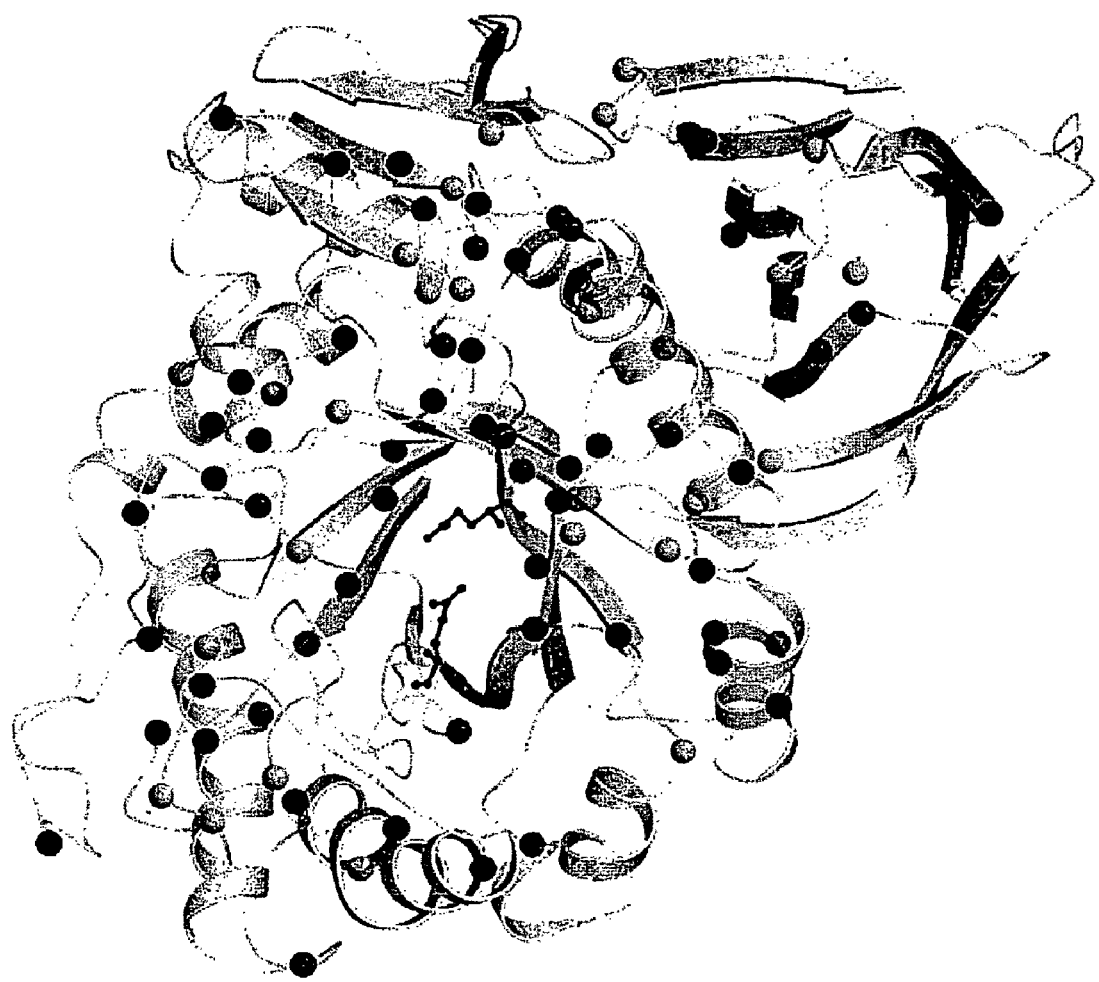
FIG. 1e is a structure diagram depicting the distribution of reported single amino acid substitutions in the 3D structure of glucocerebrosidase that lead to Gaucher disease. Mutations reported to cause severe disease are shown in red, mild disease in yellow, and those for which clinical data documenting disease severity are lacking, in blue, according to the same color code employed in FIG. 1d, above. In some cases, phenotype assignment as mild (type 1) or severe (types 2 and 3) is based on a few, or sometimes only one individual. The phenotype of a number of mutations is not known since the mutation was detected in genomic DNA and data concerning disease severity may not have been available. The active site glutamate residues are shown as black sticks.

Other naturally occurring mutations of human glucocerebrosidase which may be associated with less frequent variants of Gaucher disease are described in FIG. 1d of the Examples section which follows, and in the literature of the art [for example, refer to Beutler E. and Grabowski G A., in: "The Metabolic and Molecular Bases of Inherited Disease", Scriver C R. et al. (eds.), McGraw-Hill Inc., pp. 3635-3668 (2001)].

Portion of Mutant Glucocerebrosidase Molecule of Present Invention:

As described hereinabove, a mutant glucocerebrosidase molecule of the present invention may be characterized by any of various portions depending on the application and purpose.

Preferably, a portion of a mutant glucocerebrosidase molecule comprises a set of amino acid residues of the amino acid sequence of the mutant glucocerebrosidase molecule having at least one atom positioned within 10 angstroms of at least one atom of a reference amino acid residue of the amino acid sequence of the mutant glucocerebrosidase molecule, as described in Example 2 of the Examples section below.

Preferably, a mutant portion of a mutant glucocerebrosidase molecule of the present invention having an amino acid sequence composed of 497 amino acid residues comprises a mutated amino acid residue located at position 370, 394, 409, 444, 463, and/or 496 of the amino acid sequence of the mutant glucocerebrosidase molecule.

Preferably, the mutated amino acid residue is a Ser residue at position 370, a Leu residue at position 394, a His residue at position 409, a Pro residue at position 444, and/or a His residue at position 496.

As described hereinabove, such mutations at such positions in glucocerebrosidase molecules having amino acid sequences composed of 497 amino acid residues represent the single amino acid substitution mutations associated with the most common forms of Gaucher disease.

Preferably, the mutant portion comprising the amino acid residue at position 370 of the amino acid sequence of the mutant glucocerebrosidase molecule comprises the amino acid residues at positions 76, 81, 285, 312, 314, 320, 324, 325, 336, 364-378, 423, and 433 of the amino acid sequence of the mutant glucocerebrosidase molecule.

Preferably, the mutant portion comprising the amino acid residue at position 394 of the amino acid sequence of the mutant glucocerebrosidase molecule comprises the amino acid residues at positions 244-247, and 390-397 of the amino acid sequence of the mutant glucocerebrosidase molecule.

Preferably, the mutant portion comprising the amino acid residue at position 409 of the amino acid sequence of the mutant glucocerebrosidase molecule comprises the amino acid residues at positions 20, 21, 95-100, and 404-411 of the amino acid sequence of the mutant glucocerebrosidase molecule.

Preferably, the mutant portion comprising the amino acid residue at position 444 of the amino acid sequence of the mutant glucocerebrosidase molecule comprises the amino acid residues at positions 65-67, 440-447, 460-464, 468, and 469 of the amino acid sequence of the mutant glucocerebrosidase molecule.

Preferably, the mutant portion comprising the amino acid residue at position 463 of the amino acid sequence of the mutant glucocerebrosidase molecule comprises the amino acid residues at positions 360-366, 443-446, 460-467, and 484-89 of the amino acid sequence of the mutant glucocerebrosidase molecule.

Preferably, the mutant portion comprising the amino acid residue at position 496 of the amino acid sequence of the mutant glucocerebrosidase molecule comprises the amino acid residues at positions 33-35, 69, 71, 450-456, 474-478, and 493-497 of the amino acid sequence of the mutant glucocerebrosidase molecule.

3D Structure of Mutant Glucocerebrosidase Molecule of Present Invention:

As is described hereinabove, a mutant glucocerebrosidase molecule of the present invention, or a portion thereof, may be characterized by any of various 3D structures, depending on the application and purpose.

Preferably, the set of structure coordinates defining the structure of a mutant glucocerebrosidase molecule of the present invention defines the 3D structure of a crystallized form of such a mutant glucocerebrosidase of the present invention.

Preferably, the mutant glucocerebrosidase molecule of the present invention is characterized by a 3D structure defined by the set of structure coordinates set forth in Table 11, 13, 15, 17, 19, or 21.

As is described in the Examples section which follows, the set of structure coordinates set forth in Table 11, 13, 15, 17, 19, or 21 defines at atomic resolution an essentially complete predicted 3D structure of a mutant glucocerebrosidase molecule having the amino acid sequence set forth in SEQ ID NO: 2, 3, 4, 5, 6, or 7, respectively.

Hence, as described hereinabove, the set of structure coordinates set forth in Table 11, 13, 15, 17, 19, or 21 can be utilized for generating a model representing at atomic resolution an essentially complete predicted 3D structure of a mutant glucocerebrosidase molecule of the present invention having the amino acid sequence set forth in SEQ ID NO: 2, 3, 4, 5, 6, or 7, respectively.

3D Structure of Portion of Mutant Glucocerebrosidase Molecule of the Present Invention:

As described hereinabove, a portion of a mutant glucocerebrosidase molecule of the present invention may be characterized by any of various 3D structures, depending on the mutant glucocerebrosidase molecule of interest.

Preferably, a mutant portion of a mutant glucocerebrosidase molecule of the present invention whose structure is set forth in Table 11, 13, 15, 17, 19, or 21 has a 3D structure defined by the set of structure coordinates set forth in Table 12, 14, 16, 18, 20 or 22, respectively.

As is described and illustrated in Example 2 of the Examples section which follows, the set of structure coordinates set forth in Table 12 defines a 3D structure of a mutant portion of a mutant glucocerebrosidase molecule of the present invention having an amino acid sequence composed of 497 amino acid residues where such portion comprises amino acid residues at positions 76, 81, 285, 312, 314, 320, 324, 325, 336, 364-378, 423, and 433 of the amino acid sequence of the mutant glucocerebrosidase molecule. Hence, as described hereinbelow, this set of structure coordinates can be utilized for generating a computational model representing at atomic resolution an essentially complete predicted 3D structure of such a portion of such a glucocerebrosidase molecule.

As is described and illustrated in Example 2 of the Examples section which follows, the set of structure coordinates set forth in Table 14 defines at optimally high resolution an essentially complete 3D structure of a mutant portion of a mutant glucocerebrosidase molecule of the present invention having an amino acid sequence composed of 497 amino acid residues where such portion comprises amino acid residues at positions 244-247, and 390-397 of the amino acid sequence of the mutant glucocerebrosidase molecule. Hence, as described hereinbelow, this set of structure coordinates can be utilized for generating a computational model representing at atomic resolution an essentially complete predicted 3D structure of such a portion of such a glucocerebrosidase molecule.

As is described and illustrated in Example 2 of the Examples section which follows, the set of structure coordinates set forth in Table 16 defines at optimally high resolution an essentially complete 3D structure of a portion of a mutant glucocerebrosidase molecule of the present invention having an amino acid sequence composed of 497 amino acid residues where such portion comprises amino acid residues at positions 20, 21, 95-100, and 404-411 of the amino acid sequence of the mutant glucocerebrosidase molecule. Hence, as described hereinbelow, this set of structure coordinates can be utilized for generating a computational model representing at atomic resolution the essentially complete predicted 3D structure of such a portion of such a glucocerebrosidase molecule.

As is described and illustrated in Example 2 of the Examples section which follows, the set of structure coordinates set forth in Table 18 defines at optimally high resolution an essentially complete 3D structure of a portion of a mutant glucocerebrosidase molecule of the present invention having an amino acid sequence composed of 497 amino acid residues where such portion comprises amino acid residues at positions 65-67, 440-447, 460-464, 468, and 469 of the amino acid sequence of the mutant glucocerebrosidase molecule. Hence, as described hereinbelow, this set of structure coordinates can be utilized for generating a computational model representing at atomic resolution the essentially complete predicted 3D structure of such a portion of such a glucocerebrosidase molecule.

As is described and illustrated in Example 2 of the Examples section which follows, the set of structure coordinates set forth in Table 20 defines at optimally high resolution an essentially complete 3D structure of a portion of a mutant glucocerebrosidase molecule of the present invention having an amino acid sequence composed of 497 amino acid residues where such portion comprises amino acid residues at positions 360-366, 443-446, 460-467, and 484-89 of the amino acid sequence of the mutant glucocerebrosidase molecule. Hence, as described hereinbelow, this set of structure coordinates can be utilized for generating a computational model representing at atomic resolution the essentially complete predicted 3D structure of such a portion of such a glucocerebrosidase molecule.

As is described and illustrated in Example 2 of the Examples section which follows, the set of structure coordinates set forth in Table 22 defines at optimally high resolution an essentially complete 3D structure of a portion of a mutant glucocerebrosidase molecule of the present invention having an amino acid sequence composed of 497 amino acid residues where such portion comprises amino acid residues at positions 33-35, 69, 71, 450-456, 474-478, and 493-497 of the amino acid sequence of the mutant glucocerebrosidase molecule. Hence, as described hereinbelow, this set of structure coordinates can be utilized for generating a computational model representing at atomic resolution the essentially complete predicted 3D structure of such a portion of such a glucocerebrosidase molecule.

As described hereinabove, mutant glucocerebrosidase molecules having an amino acid sequence composed of 497 amino acid residues comprising a Ser residue at position 370, a Leu residue at position 394, a His residue at position 409, a Pro residue at position 444, and/or a His residue at position 496 represent the most common mutant glucocerebrosidase molecules associated with Gaucher disease. It will be appreciated that the set of structure coordinates set forth in Table 12, 14, 16, 18, 20 or 22 respectively defines at atomic resolution an essentially complete 3D structure of a mutant portion of such a glucocerebrosidase molecule where such portion comprises the amino acid residue located at position 370, 394, 409, 444, 463, and/or 496 of the amino acid sequence of such a glucocerebrosidase molecule. Hence, the set of structure coordinates set forth in Table 12, 14, 16, 18, 20 or 22 can respectively be used, for the first time, for generating a computer-generated model representing at atomic resolution an essentially complete predicted 3D structure of such a mutable portion of such a mutant glucocerebrosidase molecule. As such, as described hereinbelow and in the Examples section below, the set of structure coordinates set forth in Table 12, 14, 16, 18, 20 and/or 22 can be used for the first time for facilitating computational identification of drugs optimally suitable for treating the most prevalent forms of Gaucher disease.

Glycosylation:

As described hereinabove, the crystallized glucocerebrosidase molecule of the present invention may have an amino acid sequence comprising any of various glycosylation patterns.

Preferably, the crystallized glucocerebrosidase molecule of the present invention has a partially glycosylated amino acid sequence.

As used herein in relation to a crystallized glucocerebrosidase molecule of the present invention, the phrase "partially glycosylated amino acid sequence" refers to an amino acid sequence of a crystallized glucocerebrosidase molecule of the present invention having a glycosylation pattern in which at least one N-linked glycosylation consensus sequence thereof which is naturally glycosylated is non-glycosylated. It will be understood by the ordinarily skilled artisan that N-linked glycosylation consensus sequences of the amino acid sequence of glucocerebrosidase which are normally glycosylated are located at positions 19, 59, 146, and 270 of the amino acid sequence (for example, refer to Berg-Fussman A. et al., 1993. J Biol Chem. 268:14861-14866).

Preferably, the partially glycosylated amino acid sequence of the crystallized glucocerebrosidase molecule comprises a sugar moiety attached to the first N-linked glycosylation consensus sequence thereof.

As used herein, the term "first" when referring to an N-linked glycosylation consensus sequence of an amino acid sequence of a crystallized glucocerebrosidase molecule corresponds to the N-linked glycosylation consensus sequence of the amino acid sequence located closest to the amino-terminal of the amino acid sequence. For example, in the amino acid sequence set forth in SEQ ID NO: 1 or 8, the first N-linked glycosylation consensus sequence is located at position 19 of the amino acid sequence.

As is widely understood in the art, an N-linked glycosylation consensus sequence corresponds to the amino acid sequence Asn-Xaa-(Ser/Thr) (SEQ ID NO: 15), where the invariant Asn may be glycosylated (Berg-Fussman A. et al., 1993. J Biol Chem. 268:14861-14866). Such an N-linked glycosylation consensus sequence may also be referred to as a "sequon" in the art.

Preferably, the sugar moiety attached to the first N-linked glycosylation consensus sequence of the amino acid sequence of the crystallized glucocerebrosidase molecule comprises a monosaccharide or a disaccharide directly attached to the consensus sequence which is preferably composed of N-acetylglucosamine moieties.

An amino acid sequence of a crystallized glucocerebrosidase molecule having as its sole glycosylation of an N-linked glycosylation consensus sequence, a glycosylation or partial glycosylation of its first N-linked glycosylation consensus sequence is widely understood in the art as being capable of displaying normal enzymatic activity, since glycosylation of the first N-linked glycosylation consensus sequence of glucocerebrosidase is critical for enzymatic activity (for example, refer to Berg-Fussman A. et al., 1993. J Biol Chem. 268:14861-14866).

As described hereinabove, while reducing the present invention to practice, the present inventors unexpectedly devised a method of crystallizing a glucocerebrosidase molecule having optimal X-ray diffraction capacity.

Thus, according to the present invention there is provided a method of crystallizing a glucocerebrosidase molecule. The method is effected by partially deglycosylating the glucocerebrosidase molecule to thereby generate a partially glycosylated glucocerebrosidase molecule, and subjecting the partially glycosylated glucocerebrosidase molecule to crystallization-inducing conditions.

As described hereinabove, the method can be used to generate a crystallized glucocerebrosidase molecule capable of diffracting X-rays so as to enable for the first time generation of a set of structure coordinates defining at atomic resolution an essentially complete 3D structure of a normal glucocerebrosidase molecule of the present invention.

Partially deglycosylating the glucocerebrosidase molecule for crystallization thereof may be effected in various ways, for example using any of various glycosidases. Alternately, it may be achieved via alternate methods, as described hereinbelow.

Preferably, partially deglycosylating the glucocerebrosidase molecule for crystallization thereof is effected according to the protocol set forth in Examples 1 and 3 of the Examples section below, and as further described hereinbelow. Without being bound to a paradigm, the present inventors are of the opinion that the above-described deglycosylation method enabled for the first time crystallization of a glucocerebrosidase molecule having the X-ray diffraction capacity of the crystallized glucocerebrosidase molecule of the present invention by virtue of allowing optimal packing of glucocerebrosidase molecules in the crystal.

Preferably, the crystallization-inducing conditions comprise inducing evaporation of a crystallization solution containing the partially glycosylated glucocerebrosidase molecule at a concentration of about 5 mg/ml, a buffer, a sodium salt, an ammonium salt, a sulfate salt, a chaotropic compound, a potassium salt, and/or a chloride ion. Most preferably, the crystallization-inducing conditions comprise inducing evaporation of a crystallization solution containing a maximal number of the aforementioned components as well as the partially glycosylated glucocerebrosidase molecule.

Inducing evaporation of the crystallization solution may be effected in various ways.

Preferably, inducing evaporation of the crystallization solution is effected by inducing evaporation of a hanging drop thereof.

Preferably, inducing such evaporation is effected at a temperature of about 22 degrees centigrade.

Typically when inducing evaporation of a hanging drop of crystallization solution, a small drop of crystallization mixture containing a macromolecule to be crystallized is placed on a cover slip or glass plate which is inverted over a well of equilibration solution such that the cover slip or glass plate forms a seal over the well. The equilibration solution is initially at a lower volatile component vapor pressure than the crystallization mixture so that evaporation of the volatile component from the crystallization mixture to the equilibration mixture progresses at a rate fixed by the difference in the vapor pressures therebetween and by the distance between the crystallization mixture and the equilibration solution. Thus, as evaporation proceeds, the crystallization mixture becomes supersaturated with the macromolecule to be crystallized and, under the appropriate crystallization mixture conditions-including pH, solute composition and/or concentration, and temperature-crystallization occurs.

Preferably, the buffer is a Zwitterionic buffer or an acetate buffer.

Preferably, the Zwitterionic buffer is 2-morpholinoethanesulfonic acid buffer.

Preferably, the concentration of the Zwitterionic buffer in the crystallization solution is about 0.5 millimolar.

Preferably, the pH of the Zwitterionic buffer is about 6.6.

Preferably, the acetate buffer is sodium acetate buffer.

Preferably, the concentration of the acetate buffer in the crystallization solution is about 0.05 molar.

Preferably, the pH of the acetate buffer is about 4.6.

Preferably, the sodium salt is sodium chloride.

Preferably, the concentration of the sodium salt in the crystallization solution is about 0.05 molar.

Preferably, the ammonium salt is ammonium sulfate.

Preferably, the concentration of the ammonium salt in the crystallization solution is about 0.5 molar.

Preferably, the concentration of the sulfate salt in the crystallization solution is about 0.5 molar.

Preferably, the chaotropic compound is guanidine hydrochloride.

Preferably, the concentration of the chaotropic compound in the crystallization solution is about 0.085 molar.

Preferably, the potassium salt is potassium chloride.

Preferably, the concentration of the potassium salt in the crystallization solution is about 0.01 molar.

Preferably, the concentration of the chloride ion in the crystallization solution is about 0.06 molar.

The crystallization solution may have any of various pH's.

Preferably, the crystallization solution has a pH of about 4.6.

As described hereinabove, while reducing the present invention to practice the present inventors generated a set of structure coordinates defining a 3D structure of a glucocerebrosidase molecule of the present invention or a portion thereof. It will be appreciated that such a set of structure coordinates can be used to produce a computer-readable medium comprising, in a retrievable format, data including such a set of structure coordinates.

Thus, according to the present invention there is provided a computer-readable medium comprising, in a retrievable format, data including a set of structure coordinates defining a 3D structure of a glucocerebrosidase molecule or a portion thereof, wherein the set of structure coordinates defines the 3D structure at a resolution of 2.9 angstroms or higher, and/or wherein the amino acid sequence of the glucocerebrosidase molecule is partially glycosylated.

Such a computer-readable medium can be used for producing a computing platform capable of generating a model representing a 3D structure of a glucocerebrosidase molecule of the present invention or a portion thereof.

Thus, according to the present invention there is provided a computer generated model representing a 3D structure of a glucocerebrosidase molecule or a portion thereof, wherein the model represents the glucocerebrosidase molecule or the portion thereof at a resolution of 2.9 angstroms or higher, and/or wherein the glucocerebrosidase molecule is partially glycosylated.

As described hereinabove, such a computer generated model can be used for facilitating computational identification of an optimal Gaucher disease drug.

As described hereinabove, the method of identifying a compound of the present invention comprises using a set of structure coordinates defining a 3D structure of a normal glucocerebrosidase molecule of the present invention, or a portion thereof, for computationally generating a set of structure coordinates defining a predicted 3D structure of a mutant glucocerebrosidase molecule, or a portion thereof. As described hereinabove, the method of identifying the compound further comprises using a set of structure coordinates defining a 3D structure of the mutant glucocerebrosidase molecule, or portion thereof, and optionally a set of structure coordinates defining a 3D structure of the mutant glucocerebrosidase molecule, or portion thereof, for computationally identifying a compound capable of interacting with the mutant glucocerebrosidase molecule in such a way as to correct the impaired enzymatic activity thereof.

Using a set of structure coordinates defining an experimentally determined 3D structure of a molecule, such as a normal glucocerebrosidase molecule of the present invention, for generating a set of structure coordinates defining a predicted 3D structure of an altered form of such a molecule, such as a mutant glucocerebrosidase molecule of the present invention relative to the normal glucocerebrosidase molecule may be advantageously effected using widely available software applications and widely practiced computational modeling techniques. Ample guidance regarding the selection and exploitation of such computer programs is provided in the literature of the art (for example, refer to Mosyak L. et al., 1995. Nat Struct Biol. 2:537-47). In particular, the set of structure coordinates defining the predicted 3D structure of the mutant glucocerebrosidase molecule or portion thereof may be generated using a program capable of predicting the effect of an amino acid substitution on the 3D structure of a protein whose experimentally determined 3D structure is known. Preferably, generating such a set of structure coordinates is effected according to the method described in Example 2 of the Examples section which follows.

Examples of suitable programs for predicting the 3D structure of a molecule include MODELLER (Marti-Renom M. A. et al., 2000. Annu. Rev. Biophys. Biomol. Struct. 29, 291-325), ESYPRED3D (Lambert C. et al., 2002. Bioinformatics 18, 1250-6), and SWISS-MODEL (Guex N. and Peitsch M C., 1997. Electrophoresis 18, 2714-2723).

Computational identification of the compound of the present invention may be achieved by the ordinarily skilled artisan using the computational methods and software described below. Such computational identification of a compound having a desired biochemical effect on biomolecule may often be referred to in the art as "rational drug design" or "computational drug design".

Computational Drug Design:

Computational drug design is a potent means of identifying molecules capable of regulating enzyme activity which, for example, has notably been used to identify molecules capable of therapeutically regulating pathogenic HIV protease (Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109), and bcr-abl tyrosine kinase enzymatic activity (Mauro M J. et al., 2002. J Clin Oncol. 20, 325-34), and thereby to provide effective pharmacological cures for human acquired immunodeficiency syndrome (AIDS) caused by human immunodeficiency virus (HIV)), and a human cancer (chronic myeloid leukemia), respectively.

As described hereinabove, methods of computationally identifying the compound of the present invention may advantageously comprise screening a chemical structure database ("3D database"). This may be effectively performed using software employing "scanner" type algorithms which employ a set of structure coordinates defining a 3D structure of a mutant glucocerebrosidase molecule of the present invention or a portion thereof, and of a chemical structure of a candidate compound stored in the database to computationally model the "docking" of the screened compound structure with the mutant glucocerebrosidase molecule or portion thereof, and to model the resultant structure of the mutant glucocerebrosidase molecule or portion per se of that of a complex thereof with the screened compound following association of the mutant glucocerebrosidase molecule or portion thereof with the screened compound. Iterating this process with each of a plurality of chemical structures stored in the database therefore enables computational screening of such a plurality to identify a compound having a structure enabling correction of the defective structure of the mutant glucocerebrosidase molecule or portion thereof, and hence to identify a compound potentially correcting the impaired enzymatic activity of the mutant glucocerebrosidase molecule.

Examples of suitable chemical structure databases for identifying the compound of the present invention include ISIS (see the website of MDL Information Systems, San Leandro), MACCS-3D (Martin, Y. C., 1992. J. Med. Chem. 35, 2145-2154), The Cambridge Structural Database (CSD; see the website of the Cambridge Crystallographic Data Center), Fine Chemical Database (reviewed in Rusinko A., 1993. Chem Des Auto. News 8, 44-47), and the NCBI's Molecular Modeling DataBase: MMDB.

To identify the compound of the present invention via de novo computational drug design, or via modification of a known chemical structure, software comprising "builder" type algorithms utilizes a set of structure coordinates defining a 3D structure of a portion of the mutant glucocerebrosidase molecule, preferably a mutant portion thereof, and the 3D structures of basic chemical building blocks to computationally assemble a compound of the present invention. Such an approach may be employed for structurally refining a compound of the present invention identified, for example, via chemical database screening as described above.

Ample guidance for computationally identifying a compound having a desired effect on an enzyme via software employing such "scanner" and "builder" type algorithms is available in the literature of the art (for example, refer to: Halperin I. et al., 2002. Proteins 47, 409-43; Gohlke H. and Klebe G., 2001. Curr Opin Struct Biol. 11, 231-5; Zeng J., 2000. Comb Chem High Throughput Screen. 3, 355-62; and RACHEL: Theory of drug design, see New Drug Design website), and described in further detail hereinbelow.

Criteria employed by software programs used in computational drug design for qualifying the binding of screened compound structures with target portions of enzymes include gap space, hydrogen bonding, electrostatic interactions, van der Waals forces, hydrophilicity/hydrophobicity, etc. Generally, the greater the contact area between the screened chemical structure and the mutant glucocerebrosidase molecule or portion thereof, the lower the steric hindrance, the lower the "gap space", the greater the number of hydrogen bonds, and the greater the sum total of the van der Waals forces between the screened molecule and the mutant portion of the mutant glucocerebrosidase molecule, the greater will be the capacity of the screened molecule to bind with the mutant portion of the glucocerebrosidase molecule. The "gap space" refers to unoccupied space between the van der Waals surface of a screened molecule positioned within a binding pocket and the surface of the binding pocket defined by amino acid residues in the binding pocket. Gap space may be identified, for example, using an algorithm based on a series of cubic grids surrounding the docked chemical structure, with a user-defined grid spacing, and represents volume that could advantageously be occupied by a modifying the docked chemical structure positioned in contact with the mutant portion of the glucocerebrosidase molecule.

Contact area between screened compound structures and the mutant glucocerebrosidase molecule or portion thereof may be directly calculated from the coordinates of the compounds in docked conformation using the MS program (Connolly M L., 1983. Science 221, 709-713).

Suitable software employing "scanner" type algorithms include, for example, docking software such as GRAM, DOCK, or AUTODOCK (reviewed in Dunbrack et al., 1997. Folding and Design 2, 27), AFFINITY software of the INSIGHTII package (Molecular Simulations Inc., 1996, San Diego, Calif.), GRID (Goodford P J., 1985. "A Computational Procedure for Determining Energetically Favorable Binding Sites on Biologically Important Macromolecules", J. Med. Chem. 28, 849-857; GRID is available from Oxford University, Oxford, UK), and MCSS (Miranker A. and Karplus M., 1991. "Functionality Maps of Binding Sites: A Multiple Copy Simultaneous Search Method", Proteins: Structure Function and Genetics 11, 29-34; MCSS is available from Molecular Simulations, Burlington, Mass.).

The AUTODOCK program (Goodsell D S. and Olson A J., 1990. Proteins: Struct Funct Genet. 8, 195-202; available from Scripps Research Institute, La Jolla, Calif.) helps in docking screened compound structures to target portions of target biomolecules in a flexible manner using a Monte Carlo simulated annealing approach. The procedure enables a search without bias introduced by the researcher. This bias can influence orientation and conformation of a screened molecule in the targeted binding pocket.

The DOCK program (Kuntz I D. et al., 1982. J Mol. Biol. 161, 269-288; available from University of California, San Francisco), is based on a description of the negative image of a space-filling representation of the target portion of the target biomolecule, and includes a force field for energy evaluation, limited conformational flexibility and consideration of hydrophobicity in the energy evaluation.

Modeling or docking may be followed by energy minimization with standard molecular mechanics force fields or dynamics with programs such as CHARMM (Brooks B R. et al., 1983. J Comp Chem. 4, 187-217) or AMBER (Weiner S J. et al., 1984. J Am Chem Soc. 106, 765-784).

As used herein, "minimization of energy" means achieving an atomic geometry of a chemical structure via systematic alteration such that any further minor perturbation of the atomic geometry would cause the total energy of the system as measured by a molecular mechanics force-field to increase. Minimization and molecular mechanics force fields are well understood in computational chemistry (for example, refer to Burkert U. and Allinger N L., "Molecular Mechanics", ACS Monograph 177, pp. 59-78, American Chemical Society, Washington, D.C. (1982)).

Programs employing "builder" type algorithms include LEGEND (Nishibata Y. and Itai A., 1991. Tetrahedron 47, 8985; available from Molecular Simulations, Burlington, Mass.), LEAPFROG (Tripos Associates, St. Louis, Mo.), CAVEAT (Bartlett, P A. et al., 1989. Special Pub Royal Chem Soc. 78, 182-196; available from University of California, Berkeley), HOOK (Molecular Simulations, Burlington, Mass.), and LUDI (Bohm H J., 1992. J. Comp Aid Molec Design 6, 61-78; available from Biosym Technologies, San Diego, Calif.).

The CAVEAT program suggests binding structures of screened compound based on desired bond vectors. The HOOK program proposes docking sites by using multiple copies of functional groups in simultaneous searches. LUDI is a program based on fragments rather than on descriptors which proposes somewhat larger fragments to match with a target binding structure and scores its hits based on geometric criteria taken from the Cambridge Structural Database (CSD), the Protein Data Bank (PDB) and on criteria based on binding data. LUDI may be advantageously employed to calculate the inhibition constant of a docked structure. Activation constants (Ka values; opposite of inhibition constant, Ki) of structures of compounds in the final docking positions can be evaluated using LUDI software.

During or following computational selection of a screened structure of a compound, docking of an intermediate chemical structure or of the structure of the screened compound with the mutant glucocerebrosidase molecule or portion thereof may be visualized via structural models, such as 3D models, thereof displayed on a computer screen, so as to advantageously allow user intervention during the rational drug design to optimize a chemical structure.

Software programs useful for displaying such 3D structural models, include RIBBONS (Carson, M., 1997. Methods in Enzymology 277, 25), O (Jones, T A. et al., 1991. Acta Crystallogr. A47, 110), DINO (DINO: Visualizing Structural Biology (2001) see the DINO website); and QUANTA, INSIGHT, SYBYL, MACROMODE, ICM, MOLMOL, RASMOL and GRASP (reviewed in Kraulis, J., 1991. Appl Crystallogr. 24, 946).

Other molecular modeling techniques may also be employed in accordance with this invention (for example, refer to: Cohen N C. et al, 1990. "Molecular Modeling Software and Methods for Medicinal Chemistry", J. Med. Chem. 33:883-894; Navia M. A. and Murcko M. A., 1992. "The Use of Structural Information in Drug Design", Current Opinions in Structural Biology 2, 202-210). For example, where the structures of test compounds are known, a model of the test compound may be superimposed over the model of the structure of the invention. Numerous methods and techniques are known in the art for performing this step, any of which may be used (for example, refer to: Farmer P. S., "Drug Design", Ariens E J. (ed.), Vol. 10, pp 119-143 (Academic Press, New York, 1980); U.S. Pat. No. 5,331,573; U.S. Pat. No. 5,500, 807; Verlinde C., 1994. Structure 2, 577-587; and Kuntz I D., 1992. Science 257, 1078-108).

Thus, using such computational methods a large number of 3D structures of screened compounds may be quickly and easily examined and expensive and lengthy biochemical testing avoided. Moreover, the need for actual synthesis of many compounds is effectively eliminated.

Figure 4:
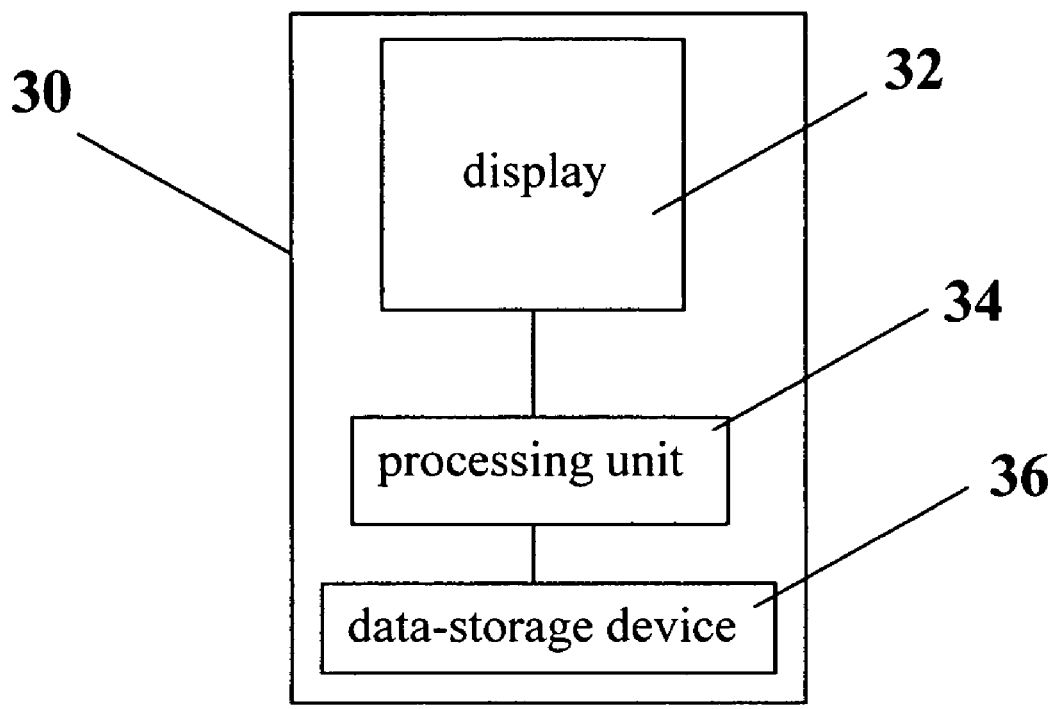
FIG. 4 is a schematic diagram depicting a computing platform for generating a model representing a 3D structure of a glucocerebrosidase molecule or a portion thereof.

Various aspects of the present invention may be advantageously practiced using a computing platform 30 (FIG. 4) which generates a graphic output of a model of a glucocerebrosidase molecule of the present invention or a portion thereof via display 32. The computing platform generates graphic representations of the model via processing unit 34 which processes a set of structure coordinates defining the 3D structure in a retrievable format in data storage device 36. Examples of computer readable media which can be used for storing a set of structure coordinates include conventional computer hard drives, floppy disks, DAT tape, CD-ROM, and other magnetic, magneto-optical, optical, floptical, and other media which may be adapted for use with computing platform 30.

Preferably the set of structure coordinates of the present invention is in PDB format (refer to enclosed CD-ROM) for convenient processing by such software applications. Most or all of these software applications, and others as well, are downloadable from the World Wide Web.

Those of ordinary skill in the art will appreciate that a set of structure coordinates defining a 3D structure of a molecule is a relative set of points that define a shape in three dimensions. Thus, it is possible that a different set of coordinates, for example a set of coordinates utilizing a different frame of reference and/or different units, could define a similar or identical shape. Moreover, it will be understood that slight variations in the individual coordinates will have little effect on overall shape. Such variations in coordinates may result, for example, from mathematical manipulations of the coordinates. For example, coordinates can be manipulated by crystallographic permutations of the atomic coordinates, fractionalization of the coordinates, integer additions or subtractions to sets of the coordinates, inversion of the coordinates or any combination of the above. Alternatively, modifications in a crystal structure from which the coordinates are derived due to mutations, additions, substitutions, or other changes in any of the components that make up the crystal could also account for variations in the coordinates. If such variations are within an acceptable standard error as compared to the original coordinates, the resulting 3D shape is considered to be the same.

Thus, the computational methods, software programs, and algorithms described hereinabove can be used by the ordinarily skilled practitioner for efficiently computationally identifying the compound of the present invention.

Once the compound of the present invention is computationally identified it may be ordered from a commercial chemical library such as, for example, one held by a large chemical company such as Merck, Glaxo Welcome, Bristol Meyers Squib, Monsanto/Searle, Eli Lilly, Novartis, Pharmacia UpJohn, and the like. The compound of the present invention may also be ordered via the World Wide Web (Internet) via companies such as Chemcyclopedia (see the "mediabrains" website). Alternatively, the compound of the present invention may be synthesized de novo using standard chemical and/or biological synthesis techniques, as appropriate to the molecular type. Ample guidance for synthesis of molecules typically identified via the above-described rational drug design methodology is provided in the literature of the art. For biological synthesis of molecules, such as polypeptides and nucleic acids, refer, for example to: Sambrook et al., infra; and associated references in the Examples section which follows. For guidance regarding chemical synthesis of molecules, refer, for example to the extensive guidelines provided by The American Chemical Society (http://www.chemistry.org/portal/Chemistry). One of ordinary skill in the art, such as, for example, a chemist, will possess the required expertise for chemical synthesis of molecules such as the compound of the present invention.

As described hereinabove, following computational identification of the compound of the present invention, the capacity of the compound to correct the impaired enzymatic activity of the mutant glucocerebrosidase molecule is preferably biochemically qualified. Such biochemical qualification may be achieved as described hereinabove.

Thus, the present invention provides a crystallized glucocerebrosidase molecule having a unique X-ray diffraction capacity enabling for the first time generation of structure coordinates defining at atomic resolution an essentially complete 3D structure of a glucocerebrosidase molecule. Such structure coordinates of the present invention enabled for the first time generation of a model representing such a structure. Furthermore, such a computing platform of the present invention enabled for the first time generation of a set of structure coordinates defining at atomic resolution an essentially complete, optimally accurate, predicted 3D structure of a mutant glucocerebrosidase molecule associated with Gaucher disease. Moreover, such computer generated models of the present invention enable for the first time identification of a compound capable of optimally correcting an impaired enzymatic activity of a mutant glucocerebrosidase molecule associated with Gaucher disease, and being characterized by essentially any desired biological, chemical and/or physical characteristics. Hence, the present invention enables identification of optimal Gaucher disease drugs targeted towards essentially any mutant human glucocerebrosidase molecule of interest.

While reducing the present invention to practice the present inventors analyzed the enzymatic activity of a preparation of the PNGaseF-treated glucocerebrosidase molecule of the present invention in order to confirm that the deglycosylation protocol employed for generating the crystallized glucocerebrosidase molecule whose structure is presently disclosed, indeed generates a fully functional human glucocerebrosidase molecule.

The present inventors uncovered that partial deglycosylation of fully deglycosylated human glucocerebrosidase (Cerezyme®) could be used to generate a partially glycosylated glucocerebrosidase preparation having essentially the same capacity to catalyze glucocerebroside hydrolysis as normal fully glycosylated human glucocerebrosidase (Cerezyme®), having the capacity to retain about full enzymatic activity under physiological conditions for a much longer duration than fully glycosylated human glucocerebrosidase having wild-type enzymatic activity levels (Cerezyme®), and having the capacity to undergo uptake by a phagocyte, such as a macrophage.

Thus, according to another aspect of the present invention there is provided a glucocerebrosidase preparation comprising a population of glucocerebrosidase molecules. In such a preparation substantially each of the glucocerebrosidase molecules has an amino acid sequence which, is at least 95 percent homologous to an amino acid sequence set forth by SEQ ID NO: 1 or 8, is glycosylated at, or has an aspartatic acid residue at, glycosylation residue 1 of the amino acid sequence, and is independently unglycosylated at least one of glycosylation residues 2, 3 and/or 4 of the amino acid sequence.

As described in further detail below, the glucocerebrosidase preparation of the present invention can be used for optimally increasing glucocerebrosidase activity in a cell, such as a macrophage, under physiological conditions, and hence can be used for treating a disease associated with glucocerebrosidase deficiency, such as Gaucher disease, with optimal therapeutic efficacy, administration of a minimal drug dose, and optimal economy.

As used herein, the phrase "substantially each of the glucocerebrosidase molecules" when relating to the population of glucocerebrosidase molecules, refers to at least 95 percent of the glucocerebrosidase molecules of the population.

As used herein, "percent homology" between a test amino acid sequence and a reference amino acid sequence (e.g. SEQ ID NO: 1 or 8) corresponds to the "Positives" output obtained for the test sequence when using the reference sequence as input to perform a standard/default search of the protein-protein BASIC LOCAL ALIGNMENT SEARCH TOOL (BLAST) [blastp] software of the National Center for Biotechnology Information (see NCBI website).

The population of glucocerebrosidase molecules may be derived from essentially any species.

Preferably, the population of glucocerebrosidase molecules is of mammalian origin, more preferably of simian origin, and most preferably of human origin.

As described above, SEQ ID NOs: 1 and 8 correspond to the amino acid sequences of Cerezyme®, a fully enzymatically active variant of human glucocerebrosidase, and of wild-type human glucocerebrosidase, respectively.

Preferably, the amino acid sequence which, is at least 95 percent homologous to an amino acid sequence set forth by SEQ ID NO: 1 or 8, has a homology with an amino acid sequence set forth by SEQ ID NO: 1 or 8 of 96 percent, more preferably 97 percent, more preferably 98 percent, more preferably 99 percent, and most preferably 100 percent.

Preferably, the amino acid sequence set forth by SEQ ID NO: 1 or 8 is set forth by SEQ ID NO: 1.

Alternately, the glucocerebrosidase may be chimpanzee (*Pan troglodytes*) glucocerebrosidase, which has an amino acid sequence set forth by SEQ ID NO: 16.

Preferably glycosylation residues 1, 2, 3 and 4 are represented by Asn19, Asn59, Asn146 and Asn270, respectively, of SEQ ID NO: 1, 8 or 16.

It will be appreciated that each of glycosylation residues 1, 2, 3 and 4 (collectively referred to hereinafter as "the glycosylation residues of the present invention") of SEQ ID NOs: 1, 8 and 16 corresponds to an Asn residue of an N-linked glycosylation consensus sequence which is normally glycosylated in human glucocerebrosidase.

Preferably, each of glycosylation residues 1, 2, 3 and 4 is flanked by the same amino acid residues flanking the Asn residue of an N-linked glycosylation sequence. Depending on the application and purpose, any of glycosylation residues 1, 2, 3 and 4 may correspond to a non-Asn amino acid residue.

Examples of glucocerebrosidase molecules having an amino acid sequence which is a variant of the amino acid sequence set forth by SEQ ID NO: 8 in which glycosylation residue 1, 2, 3 or 4 is mutated, and having glucocerebrosidase activity, include the mutant forms N19D, N19E, N59Q, N146Q, and N270Q, as described, for example, in Berg-Fussman A. et al., 1993. J Biol Chem. 268:14861-14866.

It will be appreciated that a glucocerebrosidase molecule of the present invention having an unglycosylated aspartic acid residue at glycosylation residue 1 will be capable of a similar level of glucocerebrosidase activity as one which is glycosylated at this position, as previously described in the art (refer, for example, to Erickson A H et al, 1985. J Biol Chem. 260:14319-24).

The population of glucocerebrosidase molecules having at least 95 percent homology to the amino acid sequence set forth by SEQ ID NO: 1 or 8 (hereinafter referred to as "glucocerebrosidase population of the present invention") may include glucocerebrosidase molecules in which the glycosylation residues of the present invention are separated relative to each other by a minimally varying number of amino acid residues from that separating corresponding the glycosylation residues of the present invention in SEQ ID NOs: 1, 8 or 16. Preferably such minimal variation in amino acid residue number is one of 5 amino acid residues, more preferably 4 amino acid residues, more preferably 3 amino acid residues, more preferably 2 amino acid residues, and most preferably 1 amino acid residue.

A glucocerebrosidase molecule of a glucocerebrosidase molecule population of the present invention may include a glycosylated glycosylation residue which is glycosylated with any of various types of glycosylation moieties, depending on the application and purpose.

Preferably, at least some of the glucocerebrosidase molecules of the glucocerebrosidase population are capable of being internalized by a phagocyte.

It will be appreciated that a glucocerebrosidase molecule capable of being internalized by a phagocyte by virtue of such capacity can be used to increase glucocerebrosidase activity in such a cell, as further described below.

Any of various molecular configurations known to one of ordinary skill in the art can be used to render a glucocerebrosidase molecule capable of being internalized by a phagocyte.

Preferably, according to the present invention, a glucocerebrosidase molecule is rendered capable of being internalized by a phagocyte by including a moiety which can be bound by a surface receptor of the phagocyte capable of inducing internalization of a ligand thereof.

Preferably, at least one glycosylation moiety of each of at least some, more preferably at least half, of the glucocerebrosidase molecules of the glucocerebrosidase population has at least one exposed mannose residue.

Preferably, a carbohydrate moiety of a glucocerebrosidase molecule having at least one exposed mannose residue has a Man3-Man9 structure (described in U.S. Pat. No. 6,451,600 to Genzyme Corporation).

It will be appreciated that glucocerebrosidase molecules having at least one exposed mannose residue will have the capacity to undergo uptake by a cell, such as a macrophage, having mannose-specific receptors, and that such uptake can be used to increase glucocerebrosidase activity in such a cell to any desired level, as further described below.

Preferably, the preparation of glucocerebrosidase molecules has about the same capacity to catalyze hydrolysis of a glucocerebroside as a preparation of fully glycosylated wild-type glucocerebrosidase molecules (e.g. having an amino acid sequence (SEQ ID NO: 1 or 8). Such capacity is referred to herein as "enzymatic capacity", and catalysis of hydrolysis of a glucocerebroside is referred to herein as "glucocerebrosidase activity".

Preferably, the preparation of glucocerebrosidase molecules, following an incubation in phosphate-buffered saline (PBS) solution at a temperature of 25 degrees centigrade for a duration of at least 40 hours, has about the same capacity to catalyze hydrolysis of a glucocerebroside as a preparation of wild-type glucocerebrosidase molecules (e.g. having an amino acid sequence (SEQ ID NO: 1 or 8) which has not been incubated under such conditions.

More preferably, the duration is of at least 45 hours, more preferably of at least 50 hours, more preferably of at least 55 hours, more preferably of at least 60 hours, and most preferably of at least 64 hours.

It will be appreciated that an incubation in PBS solution according to the present invention represents incubation essentially under physiological conditions since this buffer has both a pH and an osmolarity very closely approximating physiological pH and osmolarity. Since such factors are critical in determining an enzyme's catalytic activity and stability of enzymatic capacity, one of ordinary skill in the art will expect that the enzymatic activity and stability of the enzymatic capacity of a glucocerebrosidase molecule in human serum in-vivo will be very similar to that in PBS solution.

As is described and illustrated in Example 3 of the Examples section below, the preparation of the present invention has about the same capacity to catalyze hydrolysis of a glucocerebroside as a fresh preparation of a fully glycosylated wild-type glucocerebrosidase (Cerezyme®), is capable of retaining such capacity for a much longer duration under physiological conditions than such a fully glycosylated wild-type human glucocerebrosidase (Cerezyme®), and has a substantial capacity to undergo internalization by phagocytes, such as macrophages, the cell type affected with deficient glucocerebrosidase activity in Gaucher disease. As such the glucocerebrosidase preparation of the present invention can be used, as described in further detail below, to optimally increase glucocerebrosidase activity in a macrophage under physiological conditions. As such, as also described in further detail below, the glucocerebrosidase preparation of the present invention can be administered to a subject having a disease associated with glucocerebrosidase deficiency, such as Gaucher disease, so as to treat the disease with optimal therapeutic efficacy, with administration of a minimal drug dose, and with optimal economy.

Guidance for producing/obtaining the glucocerebrosidase preparation of the present invention is provided hereinbelow.

Figure 5:
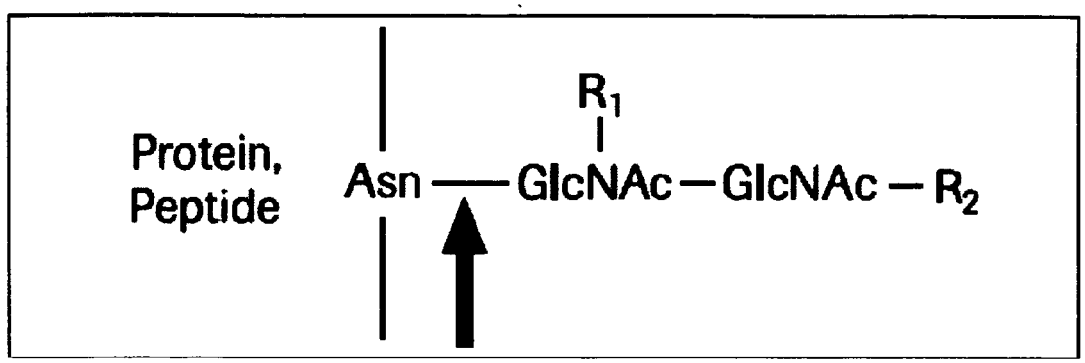
FIG. 5 is a 2-D chemical structure diagram depicting cleavage of Asn-bound N-glycans by the enzyme peptide N-glycosidase F (PNGaseF). R1, fucose alpha-1,3; R2, oligosaccharide. The cleaved chemical bond is indicated by the arrow. PNGaseF removes the whole of the carbohydrate chain by cleaving between the protein backbone (the asparagine residues) and the first sugar in the carbohydrate chain (N-acetylglucosamine).

Preferably, the glucocerebrosidase preparation is obtained by diluting glucocerebrosidase (e.g. Cerezyme®) in PBS solution to a concentration of 1.67 mg/ml, and dialyzing the solution overnight against. PBS solution so as to obtain the enzyme at a concentration of 0.9 to 1.2 mg/ml. Deglycosylation of the enzyme is then performed by treatment with peptide-N-glycosidase F [PNGaseF; peptide-$N^4$-(acetyl-$\beta$-glucosaminyl) asparagine amidase] cloned from *Flavobacterium meningosepticum* and expressed in *E. coli*, EC 3.2.218; 3.5.1.52 (Roche Diagnostics GmbH, Mannheim, Germany). This enzyme cleaves all types of asparagine bound N-glycans (Chu, F. K., 1986. J Biol Chem. 261:172-7; Tarentino, A. L. et al., 1985. Biochemistry. 24:4665-71), as indicated in the reaction scheme shown in FIG. 5 of the Examples section below, but does not necessarily remove all glycan chains from native proteins. PNGaseF is added at a concentration of 50 units/ml of dialyzed glucocerebrosidase. Deglycosylation is allowed to proceed for about 88 hours at 25 degrees centigrade. Preferably, the level of glucocerebrosidase deglycosylation is monitored over time by either SDS-PAGE, or mass spectrometry analysis, and the preparation is halted when the molecular weight of the glucocerebrosidase has been reduced from 1.5-2.5 kDa, more preferably about 2 kDa.

The glucocerebrosidase preparation of the present invention can be used per se, or formulated in a pharmaceutical composition where it is mixed with suitable carriers or excipients.

Thus, according to another aspect of the present invention there is provided a pharmaceutical composition for treating a disease associated with glucocerebrosidase deficiency in a subject in need thereof, the pharmaceutical composition comprising a pharmaceutically acceptable carrier and, as an active ingredient, the glucocerebrosidase preparation of the present invention.

Suitable pharmaceutical compositions for practicing the present invention are described in further detail hereinbelow.

As used herein a "pharmaceutical composition" refers to a preparation of one or more of the active ingredients described herein with other chemical components such as physiologically suitable carriers and excipients. The purpose of a pharmaceutical composition is to facilitate administration of active ingredients to an organism.

Herein the term "active ingredients" refers to the glucocerebrosidase preparation of the present invention accountable for the therapeutic/biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered active ingredients. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols. The pharmaceutical composition may advantageously take the form of a foam or a gel.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject of the present invention.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention are conveniently delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch. The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (glucocerebrosidase preparation of the present invention) effective to prevent, alleviate or ameliorate symptoms of a disorder (e.g., Gaucher disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve a desired biological/therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Thus, according to still a further aspect of the present invention the present invention there is provided an article of manufacture comprising packaging material and the pharmaceutical composition of the present invention, the article of manufacture being identified for treatment of a disease associated with glucocerebrosidase deficiency in a subject in need thereof.

As described above, the preparation of the present invention can be used to increase glucocerebrosidase activity in a phagocyte under physiological conditions.

Thus, according to a further aspect of the present invention there is provided a method of producing a glucocerebrosidase preparation suitable for treatment of a disease associated with glucocerebrosidase deficiency. The method is effected by exposing a plurality of glucocerebrosidase molecules to conditions suitable for partial deglycosylation thereof so as to form a population of partially deglycosylated glucocerebrosidase molecules each characterized by an amino acid sequence which is glycosylated at, or has an aspartic acid residue at, glycosylation residue 1 thereof, and which is lacking glycosylation at one or more glycosylation residues thereof selected from the group consisting of glycosylation residues 2, 3 and 4.

The glucocerebrosidase preparation of the present invention may be prepared in any of various ways, depending on the application and purpose.

Preferably, the glucocerebrosidase preparation is prepared as described in Example 3 of the Examples section below.

While the method may be effected using a plurality of glucocerebrosidase molecules having any of various amino acid sequences, depending on the application and purpose, the amino acid sequence is at least 95 percent homologous to an amino acid sequence set forth by SEQ ID NO: 8, most preferably SEQ ID NO: 1.

Any of various conditions suitable for partial deglycosylation of the plurality of glucocerebrosidase molecules may be employed, including those based on enzymatic deglycosylation, non-enzymatic chemical deglycosylation, and those based on substitution mutation of an amino acid residue at a glycosylation site of the present invention.

Preferably, the conditions suitable for partial deglycosylation of the plurality of glucocerebrosidase molecules include treating the plurality of glucocerebrosidase molecules with a glycosidase. Most preferably, the glycosidase is peptide N-glycosidase F (also referred to herein as "N-glycosidase F" or "PNGaseF").

Preferably, partially deglycosylating the plurality of glucocerebrosidase molecules with PNGaseF is effected as described in Example 3 of the Examples section which follows.

The conditions suitable for partial deglycosylation of the plurality of glucocerebrosidase molecules may include treatment with endoglycosidase H. For guidance regarding deglycosylation of glucocerebrosidase with endoglycosidase H, refer, for example, to Erickson A H et al., 1985. J Biol Chem. 260:14319-24.

One of ordinary skill in the art, such as a chemist, preferably one specialized in the chemistry of glycoproteins, will possess the necessary expertise for suitably deglycosylating glycosylation residues of the present invention. Ample guidance is provided in the art for practicing such deglycosylation (for enzymatic methods, refer, for example, to Mellors A, and Sutherland D R., 1994. Tools to cleave glycoproteins. Trends Biotechnol. 12:15-8; for chemical methods, refer, for example, to Edge A S., 2003. Biochem J. 376(Pt 2):339-50; Tams J W. et al., 1995. Mild chemical deglycosylation of horseradish peroxidase yields a fully active, homogeneous enzyme. Anal Biochem. 228:48-55; Sojar H T, and Bahl O P., 1987. A chemical method for the deglycosylation of proteins. Arch Biochem Biophys. 259:52-7; Sojar H T, and Bahl O P. Chemical deglycosylation of glycoproteins. Methods Enzymol. 138:341-50; for mutation based methods, refer, for example, to Berg-Fussman A. et al., 1993. J Biol Chem. 268:14861-14866).

As described above, a glucocerebrosidase preparation of the present invention preferably includes at least some glucocerebrosidase molecules having at least one glycosylation moiety which includes at least one exposed mannose residue so as to enable uptake by cells having mannose-specific receptors, such uptake facilitating the induction of an increase in glucocerebrosidase activity in such cells.

Any of various methods may be employed for generating glucocerebrosidase molecules having at least one glycosylation moiety which includes at least one exposed mannose residue.

The plurality of glucocerebrosidase molecules used to produce the preparation is preferably obtained commercially, preferably in the form of Cerezyme® (Genzyme Corporation; http://www.cerezyme.com). As described above, Cerezyme® is a human glucocerebrosidase molecule having an amino acid sequence set forth by SEQ ID NO: 1 which is subjected to sequential deglycosylations so as to be glycosylated with carbohydrate moieties having exposed mannose residues.

Alternately, the plurality of glucocerebrosidase molecules may be one which does not include at least some glucocerebrosidase molecules having at least one glycosylation moiety which includes at least one exposed mannose residue, such as, for example, a plurality of normally glycosylated wild-type human glucocerebrosidase molecules having an amino acid sequence as set forth by SEQ ID NO: 8, or more preferably, a plurality of glucocerebrosidase molecules having an amino acid sequence as set forth by SEQ ID NO: 1.

Any of various methods can be used for exposing mannose residues on a glycosylated glucocerebrosidase molecule.

Exposing the mannose residues may be effected by, prior to and/or concomitantly with the step of exposing the plurality of glucocerebrosidase molecules to the conditions suitable for partial deglycosylation of the plurality of glucocerebrosidase molecules, subjecting the plurality of glucocerebrosidase molecules to conditions suitable for exposing at least one mannose residue of at least one glycosylation moiety of each of at least some of the glucocerebrosidase molecules of the plurality of glucocerebrosidase molecules.

More preferably, exposing the mannose residues may be effected by subjecting partially glycosylated glucocerebrosidase molecules to conditions suitable for exposing at least one mannose residue of at least one glycosylation moiety of each at least some of the partially glycosylated molecules. This is preferably effected according to the sequential deglycosylation method employed to generate Cerezyme®, as described by the Genzyme Corporation (http://www.cerezyme.com; U.S. Pat. No. 6,451,600 to Genzyme Corporation), as also described in Example 3 of the Examples section below.

Thus, according to yet another aspect of the present invention there is provided a method of increasing glucocerebrosidase activity in a cell. The method is effected by exposing the cell to the glucocerebrosidase preparation of the present invention.

Depending on the application and purpose, the cell may be exposed to the preparation in any of various ways.

Preferably, the cell is exposed to the preparation as described in Example 3, below.

For example, the cell may be exposed to the preparation in-vitro or, alternately, by administering the glucocerebrosidase preparation to a subject.

It will be appreciated that exposing the cell to varying concentrations of the preparation in-vitro can be used to identify a suitable or optimal concentration of the preparation to which the cell should be exposed to in order to achieve desired levels, such as normal levels, of glucocerebrosidase activity in the cell.

The cell may be any of various types, depending on the application and purpose.

Preferably, the cell is of a type which is affected in Gaucher disease.

Preferably, the cell is of a type having mannose-specific receptors.

It will be appreciated that a cell having mannose-specific receptors will have the capacity to internalize glucocerebrosidase molecules of the present invention having at least one glycosylation moiety having at least one exposed mannose residues, and that such internalization will facilitate inducing an increase in the glucocerebrosidase activity in such a cell.

Preferably, the cell is a phagocyte, more preferably a macrophage. Alternately, the cell may be a neuron.

It will be appreciated that, as described above, macrophages are the principal cell type affected in type 1 Gaucher disease, and neurons are affected in type 2 and type 3 Gaucher disease.

Thus, exposing cells such as macrophages derived from a subject having type 1 Gaucher disease, or neurons derived from a subject having type 2 or 3 Gaucher disease, to varying concentrations of the preparation can be used to identify a suitable/optimal concentration of the preparation to which such cells must exposed in order for such cells to be capable of normal/desired enzymatic activity levels. It will be appreciated that, as described further below, suitably administering the preparation to such subjects so as to expose such cells in such subjects to such suitable/optimal concentrations of the preparation can be used to restore normal levels of glucocerebrosidase activity in-vivo in such subjects, so as to treat the disease in such subjects.

Thus, according to still another aspect of the present invention there is provided a method of treating a disease associated with glucocerebrosidase deficiency in a subject in need thereof, the method comprising administering to the subject in need thereof a therapeutically effective amount of the preparation of the present invention.

As used herein, the term "treating" refers to preventing onset of the disease, alleviating, attenuating, palliating or eliminating the symptoms of a disease, slowing, reversing or arresting the progression of the disease, or curing the disease.

Administering the therapeutically effective amount of the glucocerebrosidase preparation to the subject may be effected in any of various ways, depending on the application and purpose, as further described hereinbelow.

Preferably, the preparation is administered to the subject systemically, most preferably via the injection route.

Alternately, the preparation may be administered to the subject locally.

Preferably, the disease associated with glucocerebrosidase deficiency is Gaucher disease.

Since the preparation of the present invention preferably corresponds identically or essentially identically to a partially glycosylated form of human glucocerebrosidase, such as Cerezyme®, and since administration of Cerezyme® is the standard, widely employed treatment for Gaucher disease, one of ordinary skill in the art, such as a physician, preferably a physician specialized in the treatment of Gaucher disease, will possess the necessary expertise for easily adapting the standard treatment methods towards administering the preparation of the present invention for optimal treatment of Gaucher disease. Ample guidance is available to the ordinarily skilled artisan for adapting the teachings of the present invention for treating a disease associated with glucocerebrosidase deficiency such as Gaucher disease by administration of the preparation of the present invention (refer, for example, to: guidelines provided by the Genzyme Corporation, http://www.cerezyme.com; U.S. Pat. No. 6,451,600 to Genzyme Corporation; Charrow J. et al., 2004. Enzyme replacement therapy and monitoring for children with type 1 Gaucher disease: consensus recommendations. J. Pediatr. 144:112-20; Poll L W. et al., 2002. Response of Gaucher bone disease to enzyme replacement therapy. Br J Radiol. 75 Suppl 1:A25-36; Vellodi A. et al., 2001. Management of neuronopathic Gaucher disease: a European consensus. J Inherit Metab Dis. 24:319-27; Beutler E., 1997. Gaucher disease. Curr Opin Hematol. 4:19-23; Kingma W., 1996. Gaucher disease: an overview of clinical characteristics and therapy. J Intraven Nurs. 9:79-82).

For example, depending on various relevant patient-specific parameters, between 10 and 500 milligrams of a glucocerebrosidase preparation of the present invention may be administered per 70 kg of patient per month for optimal treatment of Gaucher disease.

As described and illustrated in Example 3 of the following Examples section, the preparation of the present invention has about the same capacity to catalyze hydrolysis of a glucocerebroside as a Cerezyme® preparation, has far greater stability of enzymatic capacity than Cerezyme® under physiological conditions, and is capable of undergoing essentially normal levels of internalization/uptake by macrophages. As such, it will be appreciated that the preparation of the present invention can be used for treating Gaucher disease, with optimal therapeutic efficacy, minimal drug administration, and optimal economy, relative to prior art methods employing Cerezyme®.

Relevant guidance regarding various aspects of the present invention may be found in U.S. Pat. No. 6,451,600 to Genzyme Corporation.

Thus, the present invention provides a glucocerebrosidase preparation having normal glucocerebrosidase activity levels, and optimal stability of enzymatic activity under physiological conditions, which by virtue of such unique characteristics, can be used for treating Gaucher disease with optimal therapeutic efficacy, with a minimally low drug dosing regimen, and with optimal economy, thereby overcoming numerous critical limitations of the prior art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

The 3D Atomic Structure of Human Glucocerebrosidase

Gaucher disease is a highly debilitating disease caused by mutant glucocerebrosidase molecules having impaired enzymatic activity, and for which no satisfactory treatment is available. An optimal drug for treatment of Gaucher disease would be of optimally small dimensions, have a non-polypeptidic composition, and would be capable of correcting impaired glucocerebrosidase enzymatic activity in mutant glucocerebrosidase molecules associated with pathogenesis of the disease. Ideally, such compounds could be computationally identified using computing platforms capable of generating atomic resolution models representing 3D atomic structures of glucocerebrosidase molecules. The prior art, however, has failed to provide computing platforms suitable for performing such rational drug design. As described below, while reducing the present invention to practice, the present inventors have overcome the limitations of the prior art by producing a computing platform capable of generating a model representing at atomic resolution the essentially complete, experimentally determined 3D structure of human glucocerebrosidase, thereby enabling computational identification of optimal Gaucher disease drugs.

Materials and Methods:

Crystallization: A 5 mg aliquot of Cerezyme®, a recombinant variant of human glucocerebrosidase having the natural Arg495 residue substituted with a His residue, and oligosaccharide chains of glycosylated N-linked glycosylation sites modified to terminate in mannose sugars, was dialyzed overnight against phosphate-buffered saline (PBS) pH 7.0 and deglycosylated by incubation at 25° C. for 88 hours with 150 units N-glycosidase F. Cerezyme®, which exhibits an enzymatic activity identical to that of natural human glucocerebrosidase (Grabowski G A. et al., 1995. Ann Intern Med. 122:33-9) and is thereby properly folded, was employed due to its availability as the active ingredient of the commercial drug Cerezyme® (Genzyme Corporation, Cambridge, Mass., USA). Deglycosylation was monitored by the reduction in molecular weight of the enzyme by SDS-PAGE, and mass spectrometry revealed removal of 7-14 sugar residues. The concentration of the deglycosylated enzyme was adjusted to 10 mg/ml in 1 millimolar 2-morpholinoethanesulfonic acid (MES) pH 6.6, 0.1 molar NaCl, 0.02% $NaN_3$ using a Centricon YM-10 centrifugal concentrator equipped with a molecular weight cut-off filter of about 10 kDa. Crystals were obtained via the hanging-drop technique at room temperature using a drop composed of 1.5 microliters of the 10 mg/ml glucocerebrosidase solution and 1.5 microliters of mother liquor [1 molar $(NH_2)_2SO_4$ pH 4.6, 0.17 molar guanidine hydrochloride, 0.02 molar KCl, 0.1 molar sodium acetate buffer, pH 4.6]. Crystals were cryo-protected with a gradient of 5-25% glycerol. A heavy-atom derivative was obtained by soaking for 3 days in a 1:125,000 dilution of $KHgI_2$ in mother liquor.

Data collection: X-ray data were collected at 100K at 3 wavelengths around the Hg LIII-edge on beamline ID14-4, and a native data set on beamline BM14 at the European Synchrotron Radiation Facility (Grenoble, France). The enzyme crystallized in a $C222_1$ space group with two molecules in the asymmetric unit. The data was processed using MOSFLM/SCALA (Leslie A G W., 1992. Joint CCP4+ESF-EAMCB Newsletter on Protein Crystallography 26) and DENZO/SCALEPACK (Otwinowski Z. and Minor W., 1997. Methods Enzymol. 276:307-326) software. The space group and cell dimensions obtained were similar to those recently reported for crystals of the glycosylated form of the enzyme which diffracted, however, to significantly lower resolution (Roeber D. et al., 2003. Acta Cryst. D59:343-344). Data collection statistics are shown in Table 1.

TABLE 1

Data collection statistics

|  | Hg inflection | Hg peak | Hg remote | Native |
|---|---|---|---|---|
| Wavelength (angstroms) | 1.0092 | 1.0075 | 1.0015 | 0.8856 |
| Unit cell (angstroms) | 109.2, 286.1, 91.5 | 109.2, 286.7, 91.5 | 108.9, 284.1, 91.2 | 107.7, 285.2, 91.8 |
| Resolution range (angstrom) | 26-2.35 | 26-2.27 | 26-2.27 | 10-2.00 |
| No. of unique reflections | 58,766 | 64,819 | 64,311 | 93,248 |
| Completeness (%) | 97.1 (98.3)* | 96.1 (87.8)* | 97.5 (99.1)* | 98.4 (98.3)* |
| I/σ(I) | 9.6(2.6)* | 9.52(2.1)* | 9.1(2.3)* | 7.4(1.6)* |
| Rsym(I) (%) | 7.0(24.7)* | 7.2(29.0)* | 7.7(29.4)* | 8.4(37.3)* |

*Data for outer shell are in parentheses.

Structure determination and refinement: Three Hg sites were located based on their anomalous difference using SHELXD software (Uson I. and Sheldrick G M., 1999. Curr Opin Struct Biol. 9:643-648). The Hg sites were refined, and experimental phases to 2.3 angstroms were calculated from the MAD data using SHARP software (Fortelle E. and Bricogne G., 1997. Methods Enzymol. 276:472-494), resulting in an overall FOM of 0.403. Phases were improved by applying solvent flipping density modification using SOLOMON software (Abrahams J P. and Leslie A G., 1996. Acta Crystallogr D52:30-42), resulting in an overall FOM of 0.851. Automated tracing procedure performed using ARP/wARP software (Perrakis A. et al., 1999. Nature Struct Biol. 6:458-463), using native amplitudes to 2.0 angstroms, coupled to the experimental phases, resulted in tracing of about 95% of the two polypeptide chains. The σA map shows all 497 residues in both molecules. Final tracing was performed manually using O software (Jones T A. et al., 1991. Acta Cryst A47:110-119). Refinement of the two molecules was performed using REFMAC (Murshudov G N. et al., 1999. Acta Cryst D55:247-255) and CNS (Brunger A T. et al., 1998. Acta Cryst. D54:905-921) software at 2.0 angstroms, with an overall rmsd of 0.29 angstroms for Cα atoms between the two molecules. The maps showed a single glycosylation site at Asn19 with one N-acetylglucosamine moiety on one molecule and two on the other. 809 water molecules and 15 sulfate ions were assigned. Refinement and model statistics are shown in Table 2.

Experimental Results:

Following extensive empirical experimentation, highly purified, highly ordered human glucocerebrosidase polypeptide crystals were successfully grown. X-ray crystallographic analysis of such crystals generated Protein DataBank (PDB) a set of structure coordinates defining the essentially complete 3D atomic structure of human glucocerebrosidase polypeptide at 2.0 angstroms (Table 4, enclosed CD-ROM). The refined structure (R-factor 19.9%, R-free 23.2%) indicated that crystallized glucocerebrosidase contains two enzyme molecules per asymmetric unit. The overall fold of the enzyme comprises 3 domains (FIGS. 1b and 1c). Domain I (residues 1-27 and 383-414) consists of one major 3-stranded anti-parallel beta-sheet flanked by a perpendicular N-terminal strand and a loop. It contains two disulfide bridges (residues 4-16 and 18-23), which may be required for correct folding [Beutler E. and Grabowski G A., in: "The Metabolic and Molecular Bases of Inherited Disease", Scriver C R. et al. (eds.), McGraw-Hill Inc., pp. 3635-3668 (2001)]. Glycosylation, which is essential for catalytic activity in-vivo (Berg-Fussman A. et al., 1993. J Biol Chem. 268:14861-14866), is seen in the crystal structure at Asn19. Domain II (residues 30-75, 431-497) consists of two closely-associated beta-sheets forming an independent domain resembling an immunoglobulin (Ig) fold (Orengo et al., 1997. Structure 5:1093; Westhead et al., 1999. Protein Sci. 8:897). Domain III (residues 76-381, 416-430) is a (beta/α)$_8$ (TIM) barrel containing the catalytic site, consistent with homology to GH-A clan members (Fabrega S. et al., 2002. J Soc Biol. 196:151-60; Henrissat and Bairoch, 1993. Biochem. J. 316:695-696). It contains three free cysteines (residues 126, 248 and 342). Domains II and III appear to be connected by a hinge region located between helix 8 and strand 1 of the TIM-barrel and the loops connecting the two domains, whereas domain 1 tightly interacts with domain III.

Figure 2A:
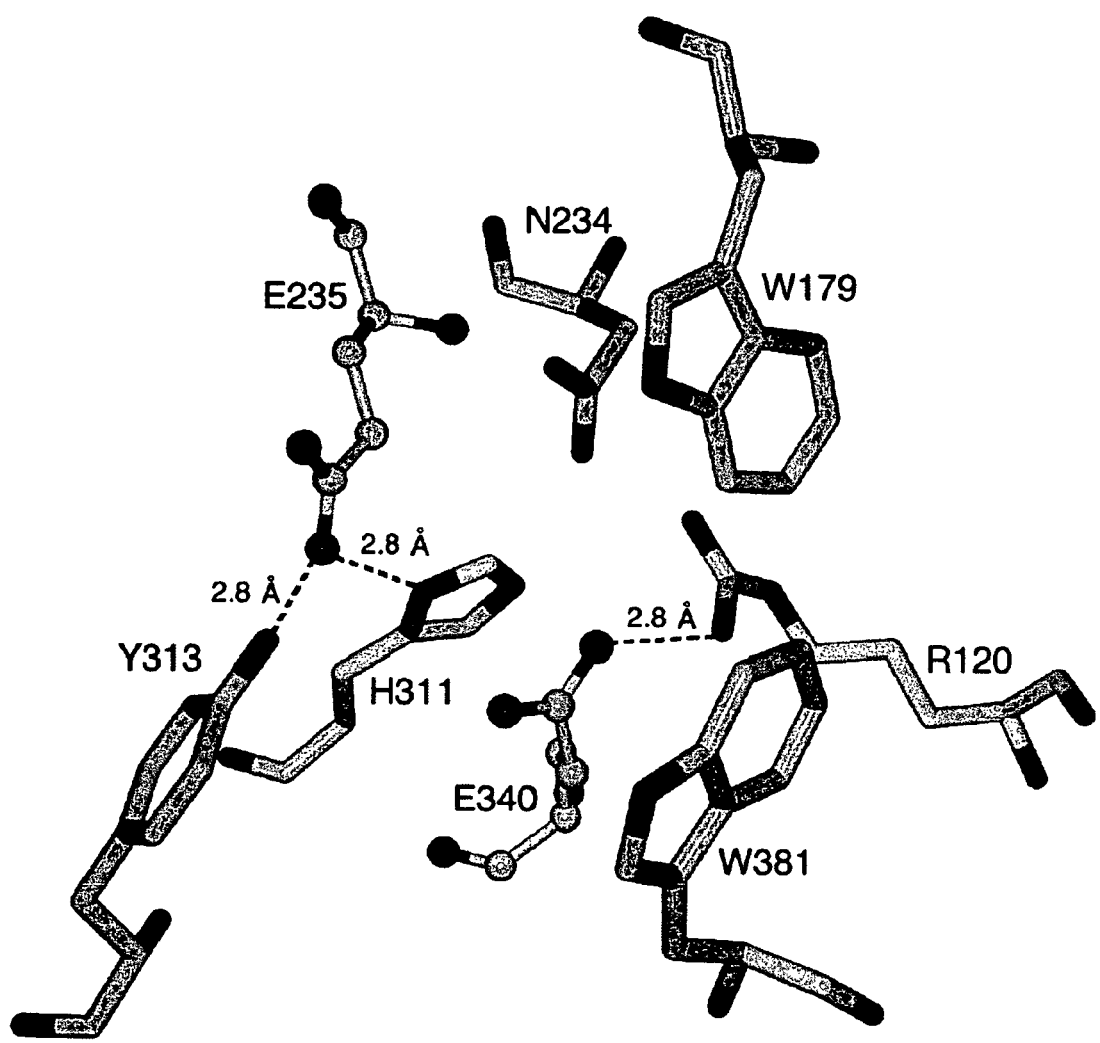
FIG. 2a is a 3D structure diagram depicting the catalytic and glucone binding site of a human glucocerebrosidase molecule capable of displaying normal enzymatic activity. Amino acid residues near the catalytic glutamates (ball-and-stick models) are rendered as stick models. H-bonds are shown as dashed lines for those residues in contact distance to the glutamates. These residues may be directly involved in catalysis or modulate the protonation states of the carboxyl groups. The others are near the docked glucosyl moiety (see FIG. 2b, below), and may thus stabilize its interaction with glucocerebrosidase.
Figure 2B:
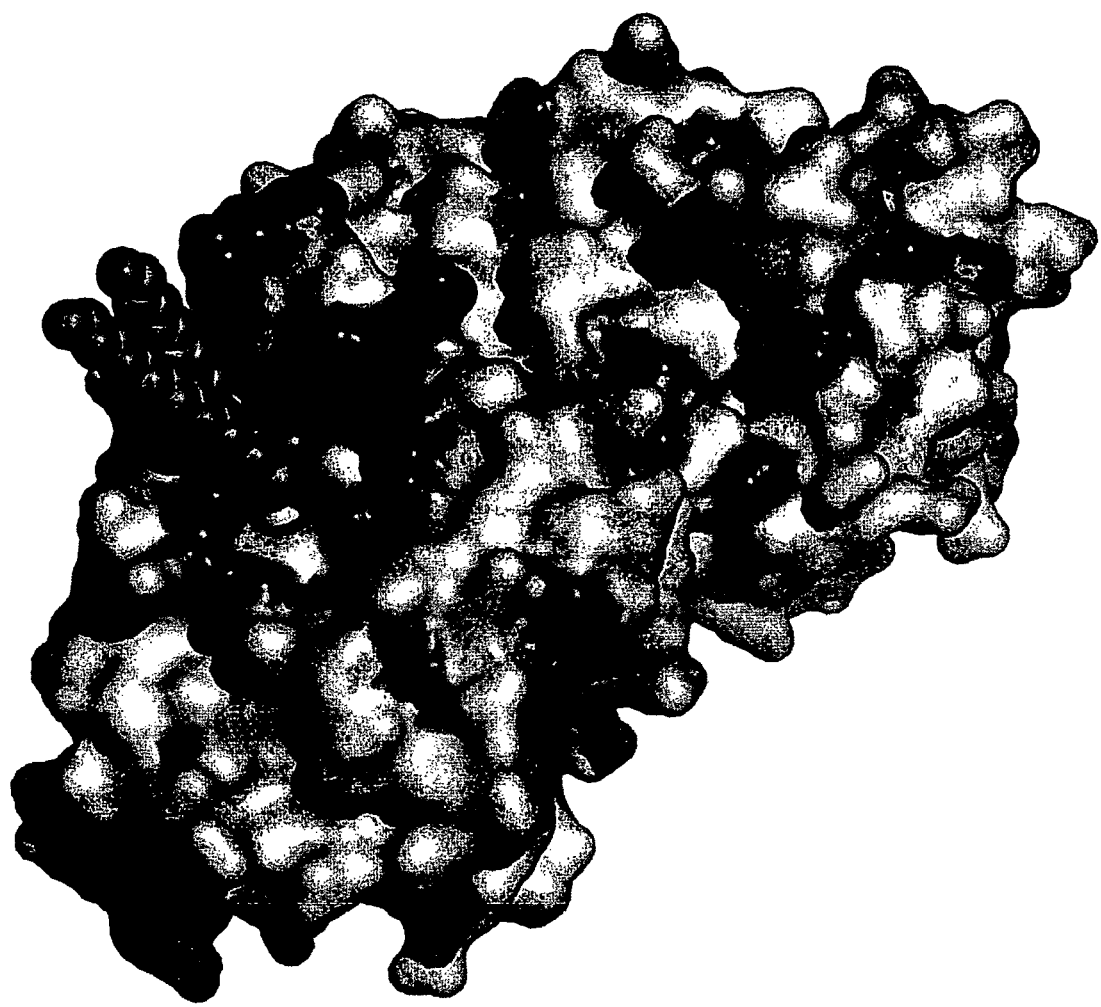
FIG. 2b is a diagram depicting the 3D surface of a human glucocerebrosidase molecule capable of displaying normal enzymatic activity with a model of the docked glucosylceramide substrate. Hydrophobic residues (W, F, Y, L, I, V, M and C; Hopp T P. and Woods K R., 1981. Proc Natl Acad Sci USA. 78:3824-8) are shown in blue, and the active site residues (E235 and E340) in yellow. Glucosylceramide is shown in CPK format (carbon and oxygen atoms in green and red, respectively). The model of the docked substrate was based on the coordinates of galactosylceramide (Nyholm P G. et al., 1990. Chem Phys Lipids 52:1-10) modified for glucosylceramide. The surface diagram of glucocerebrosidase was rendered using PYMOL software (http://www.pymol.org).

Site-directed mutagenesis and homology modeling of glucocerebrosidase (Fabrega S. et al., 2000. Glycobiology 10:1217-24; Fabrega S. et al., 2002. J Soc Biol. 196:151-60) suggested that E235 is the acid/base catalyst and E340 the nucleophile (Miao S. et al., 1994. J Biol Chem. 269:10975-10978). These two residues are located near the C-termini of strands 4 and 7 (FIGS. 1b and 2a) in domain III, with an average distance between their carboxyl oxygens of 5.2 angstroms for the two glucocerebrosidase molecules in the structure, consistent with retention of the anomeric carbon upon cleavage, rather than inversion (Davies G. and Henrissat B., 1995. Structure 3:853-859). Thus residues D443 and D445, now known to be located in the Ig-like domain (FIG. 1b), cannot be directly involved in catalysis even though they are covalently labeled (Dinur T. et al., 1986. Proc Natl Acad Sci USA. 83:1660-1664) by the irreversible glucocerebrosidase inhibitor, conduritol-B-epoxide (Legler G., 1977. Methods Enzymol. 46:368-381). Substrate docking shows that only the glucose moiety and adjacent glycoside bond of glucosylceramide fit within the active site pocket (FIG. 2b), implying that the two glucosylceramide hydrocarbon chains either remain embedded in the lipid bilayer during catalysis or alternatively interact with saposin C. In addition, an annulus of hydrophobic residues surrounds the entrance to the active site (FIG. 2b), and may facilitate interaction of glucocerebrosidase with the lysosomal membrane or with saposin C (Legler G., 1977. Methods Enzymol. 46:368-381).

TABLE 2

Refinement and model statistics

| | |
|---|---|
| Resolution range (angstroms) | 14.4-2.0 |
| No. of reflections | 88,501 |
| R-factor (%) work, free | 19.5, 23.0 |
| No. of atoms: | |
| Protein (994 residues) | 7,859 |
| Hetero (carbohydrate, solvent) | 1,056 |
| Average B-factors (square angstroms) | 28.4 |
| RMSD from ideal values: | |
| Bond length (angstroms) | 0.005 |
| Bond angle (degrees) | 1.3 |
| Dihedral angles (degrees) | 23.8 |
| Improper torsion angles (degrees) | 0.86 |
| Estimated coordinate error: | |
| Low resolution cutoff (angstroms) | 5.0 |
| ESD from Luzzati plot (angstroms) | 0.23 |
| ESD from sigmaA (angstroms) | 0.32 |
| Ramachandran outliers (%) | 3.1 |

Figure 3:
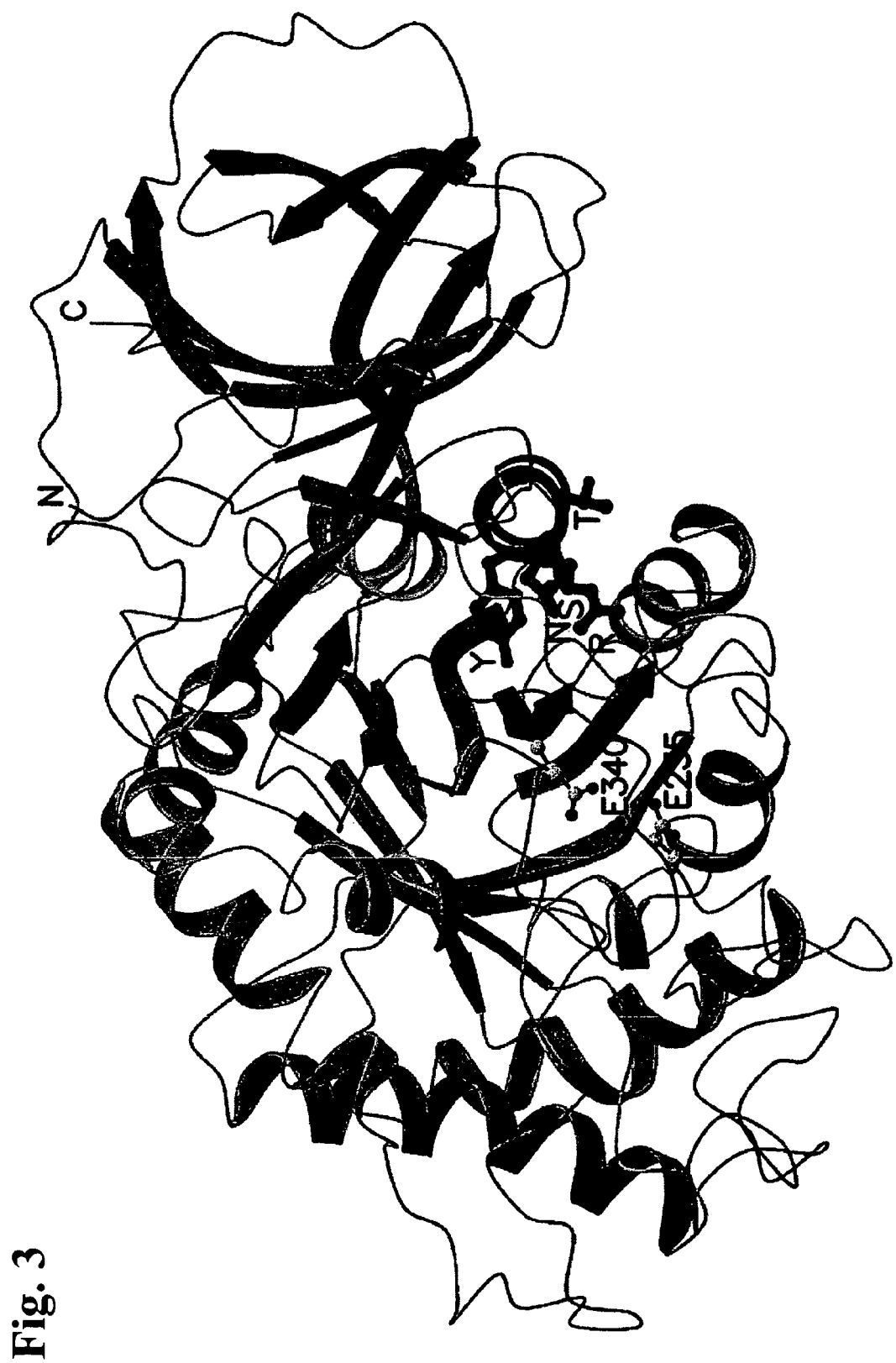
FIG. 3 is a 3D structure diagram depicting a cluster of mutations in helix 7 in human glucocerebrosidase. The transparent ribbon diagram shows the three domains of glucocerebrosidase as in FIG. 1a, but rotated by about 90 degrees around the x-axis to look down helix 7 (colored red). The amino acids mutated in Gaucher disease on this helix (R359, Y363, S366, T369, N370) are depicted as red balls and sticks. The active site residues E235 and E340 are depicted with carbon atoms as yellow balls and oxygen atoms as red balls.

Of the approximately 200 known glucocerebrosidase mutations (FIGS. 1d-e), many are rare and restricted to a few individuals. Most mutations partially or entirely decrease catalytic activity (Meivar-Levy, I. et al., 1994. Biochem. J. 303:377-382) or are believed to reduce glucocerebrosidase stability (Grace M E. et al., 1994. J Biol Chem. 269:2283-2291). The most common mutation, N370S, accounts for 70% of the mutant alleles in Ashkenazi Jews and 25% of non-Jewish patients [Beutler E. and Grabowski G A., in: "The Metabolic and Molecular Bases of Inherited Disease", Scriver C R. et al. (eds.), McGraw-Hill Inc., pp. 3635-3668 (2001)]. This mutation predisposes to Type 1 disease and always precludes neurological involvement, implying that it causes relatively minor changes in glucocerebrosidase structure, and hence catalytic activity. Consistent with this is the localization of N370 to the longest α-helix (helix 7) in glucocerebrosidase, which is located at the interface of domains II and III, but is too far from the active site to directly participate in catalysis. Interestingly, a number of other mutations are found in this helix, all of which appear to point into the TIM-barrel (FIG. 3).

Seven aromatic side chains (F128, W179, Y244, F246, Y313, W381, F397) line one side of the active site pocket, which may be involved in substrate recognition and has been observed in other beta-glycosidases (Chi Y I. et al., 1999. FEBS Lett. 445:375-383; Henrissat B. and Bairoch A., 1993. Biochem J. 293:781-788). The common mutation V394L [Beutler E. and Grabowski G A., in: "The Metabolic and Molecular Bases of Inherited Disease", Scriver C R. et al. (eds.), McGraw-Hill Inc., pp. 3635-3668 (2001); Table 3] might perturb this lining as the bulkier leucine side chain could cause a conformational change in 2 members of the lining, Y244 and F246.

hexosaminidase and other family 20 glycosidases have a similar non-catalytic domain whose role is unknown (Mark B L. et al., 2001. J Biol Chem. 276:10330-7).

The saposin C structure has recently been determined by NMR (PDB ID code 1M12), but its coordinates are on hold. However, the structure of its homolog saposin B (Ahn V E. et al., 2003. Proc Natl Acad Sci USA. 100:38-43), reveals that the putative active form is a dimer in which a large hydrophobic cavity sequesters the acyl chains of cerebroside sulfate, and may serve to present it appropriately for hydrolysis by arysulfatase A. It cannot yet be established whether such a mechanism would explain the role of saposin C as an activator

TABLE 3

Most common single amino acid substitutions in glucocerebrosidase associated with Gaucher disease.

| Mutation* | Phenotype | Features | Enzyme activity | Structural features |
|---|---|---|---|---|
| N370S | Mild | 70% of mutant alleles in Ashkenazi Jews; invariably predisposes to mild (type 1) disease | Reduced activity; stable protein | On longest helix (helix 7) in protein at interface of domains II and III. Several other mutations are found on this helix (see FIG. 3) |
| V394L | Severe | | Reduced activity; stable protein | Near aromatic residues that line one side of the active site pocket; may disrupt this lining and thus catalytic activity |
| D409H | Severe | | Highly reduced activity; unstable protein | On domain I, suggesting regulatory or structural role for this domain |
| L444P | Severe | Most common mutation predisposing to severe (type 2/3) disease | Reduced activity; unstable protein | Hydrophobic core of Ig-like domain (domain II), which may lead to unstable protein due to disruption of the hydrophobic core and altered folding of this domain |
| R463C | Mild | | Reduced activity; stable protein | On Ig-like domain, distant from the active site |
| R496H | Mild | | | On Ig-like domain, distant from the active site |

*For references pertaining to each of these mutations, refer to Beutler E. and Grabowski G A., in: "The Metabolic and Molecular Bases of Inherited Disease", Scriver C R. et al. (eds.), McGraw-Hill Inc., pp. 3635-3668 (2001)]

Several other mutations occur near the active site, i.e., H311, R341 and C342, and may directly affect catalytic activity. In contrast, two relatively common mutations (Table 3), R463C and R496H, which predispose to mild disease [Beutler E. and Grabowski G A., in: "The Metabolic and Molecular Bases of Inherited Disease", Scriver C R. et al (eds.), McGraw-Hill Inc., pp. 3635-3668 (2001)], are located in the Ig-like domain at a considerable distance from the active site (FIG. 1b).

Unexpectedly, L444, which is mutated relatively frequently to proline or arginine, and invariably predisposes to severe neuronopathic disease [Beutler E. and Grabowski G A., in: "The Metabolic and Molecular Bases of Inherited Disease", Scriver C R. et al. (eds.), McGraw-Hill Inc., pp. 3635-3668 (2001); Erikson, A. et al. in "Gaucher Disease", Zimran, A. (ed.), Vol. 10, Bailliere Tindall, London, pp. 711-723 (1997)], is located in the hydrophobic core of the Ig-like domain (FIG. 1b). Either of the two L444 mutations would likely cause a local conformational change by disrupting the hydrophobic core, resulting in altered folding of this domain (Morel N. et al., 1999. Mol Pharmacol. 55:982-992), consistent with the assumption that these mutations produce unstable protein (Grace M E. et al., 1994. J Biol Chem. 269:2283-2291). This implies an important regulatory or structural function for domain II, perhaps in interacting with saposin C and/or acidic phospholipids. Interestingly, betaof glucocerebrosidase since the limited sequence homology (less than 14%) between saposins B and C does not permit accurate modeling of the latter. However, the Ig-like domain of glucocerebrosidase may regulate the interaction of glucocerebrosidase with either the lipid bilayer, with saposin C, or both. Finally, the lack of known viable mutations in residues 14-20 of domain I and in the connecting strand (1-10) and loop (21-27), with the exception of the conserved mutation V15L, together with the 7 known mutations in the C-terminal strand of this domain (401-414), including the common severe mutation D409H which results in unstable protein [Beutler E. and Grabowski G A., in: "The Metabolic and Molecular Bases of Inherited Disease", Scriver C R. et al. (eds.), McGraw-Hill Inc., pp. 3635-3668 (2001)], suggests that domain I also has an important regulatory or structural role.

In summary, the catalytic domain of glucocerebrosidase consists of a $(\beta/\alpha)_8$ (TIM) barrel found also in the GH-A glycosidase clan. The catalytic residue E235 is H-bonded to H311 and Y313, and E340 is H-bonded to R120. The catalytic residues, E340 and E235, are hydrogen-bonded to R120 and to Y313 and H311, respectively, with the distance between the two glutamates consistent with a catalytic mechanism of retention. N370 is located on helix 7, which is at the interface of the TIM-barrel and a separate immunoglobulin-like domain on which L444 is located, implying a key regulatory or structural role for this non-catalytic domain.

The above described data is presented and discussed in Dvir, H. et al., 2003. EMBO Rep. 4:704-709; Futerman, A. H. et al., 2004. *Trends in Pharmacological Science*, in press.

Conclusion: The presently described crystallization method enabled for the first time relative to the prior art generation of crystals of human glucocerebrosidase having an X-ray diffraction capacity enabling generation of sets of structure coordinates defining at atomic resolution the essentially complete 3D structure of human glucocerebrosidase. Such sets of structure coordinates were used for the first time for generating computer-generated models representing at an essentially complete 3D atomic structure of human glucocerebrosidase. As such, the presently described computing platforms enable computational identification of compounds optimally capable of correcting impaired enzymatic activity of mutant glucocerebrosidase molecules associated with pathogenesis of Gaucher disease, and thereby identification of Gaucher disease drugs overcoming all shortcomings of prior art Gaucher disease drugs.

Example 2

The Essentially Complete, Optimally Accurate, Predicted 3D Atomic Structure of Human Glucocerebrosidase Mutants Associated with Gaucher Disease As described above, whole enzyme replacement therapy using recombinant glucocerebrosidase is currently the treatment of choice for treatment of Gaucher disease. Such treatment, however, suffers from numerous significant drawbacks, as described above. Hence, novel and improved Gaucher disease drugs are urgently required. Optimal Gaucher disease drugs, would be compounds having optimally small dimensions and a non-polypeptidic chemical composition, and would be capable of interacting with mutant glucocerebrosidase molecules associated with Gaucher disease in such a way as to correct impaired enzymatic activity thereof. Ideally, such compounds could be computationally identified using computing platforms capable of generating essentially complete, experimentally determined, models representing 3D atomic structures of human glucocerebrosidase molecules. The prior art has, however, failed to provide such computing platforms. While reducing the present invention to practice, the present inventors have provided computing platforms overcoming such prior art limitations, as follows.

Materials and Methods:

Set of PDB structure coordinates defining the essentially complete predicted structure of common human glucocerebrosidase mutants: Sets of structure coordinates defining the predicted, essentially complete, 3D structure of human glucocerebrosidase mutants Asn370Ser, Val394Leu, Asp409His, Leu444Pro, Arg463Cys, and Arg496His were generated using the set of structure coordinates corresponding to atom coordinates 1-3929 set forth in Table 4 (enclosed CD-ROM) which define an essentially complete, experimentally determined, 3D structure of normal human glucocerebrosidase, as described in Example 1 of the Examples section above. Briefly, structure coordinates were generated using SHELXD software to locate the positions of the heavy atoms, SHARP and SOLOMON to get an initial electron density map, and CNS and O to refine and fit the chain into the map.

A set of structure coordinates defining the predicted structure of the set of amino acid residues predicted to have at least one atom positioned within 10 angstroms of at least one atom of a mutated amino acid were also identified for each of the aforementioned human glucocerebrosidase mutants associated with Gaucher disease. The structure of such a set of amino acid residues located within 10 angstroms of the mutated amino acid residue is hereinafter referred to as "10-angstrom radius structure". A similar 10-angstrom radius structure was defined for each mutation within the structure of the non-mutated enzyme. These non-mutated 10-angstrom radius structures are defined by sets of Table 4 (enclosed CD-ROM) coordinates defining the structures of sets of amino acid residues from the amino acid sequence of the non-mutated glucocerebrosidase molecule located at the same positions within the amino acid sequence of the non-mutated glucocerebrosidase molecule (SEQ ID NO: 1) as the amino acid residues included in the 10-angstrom radius structures of the corresponding mutant glucocerebrosidase molecule within the amino acid sequence of the mutated glucocerebrosidase molecule.

Results:

Structure coordinates defining the predicted, essentially complete, 3D structures of human glucocerebrosidase (Cerezyme®) mutants Asn370Ser (SEQ ID NO: 2), Val394Leu (SEQ ID NO: 3), Asp409His (SEQ ID NO: 4), Leu444Pro (SEQ ID NO: 5), Arg463Cys (SEQ ID NO: 6), and Arg496His (SEQ ID NO: 7) at 2.0 angstrom resolution were generated (Tables 11, 13, 15, 17, 19, and 21, respectively, enclosed CD-ROM). These structure coordinates were used to generate:

(i) a set of structure coordinates defining the 10-angstrom radius structure defined in relation to Ser370 in human glucocerebrosidase mutant Asn370Ser (Table 12, enclosed CD-ROM);

(ii) a set of structure coordinates defining the 10-angstrom radius structure defined in relation to Leu394 in human glucocerebrosidase mutant Val394Leu (Table 14, enclosed CD-ROM);

(iii) a set of structure coordinates defining the 10-angstrom radius structure defined in relation to His409 in human glucocerebrosidase mutant Asp409His (Table 16, enclosed CD-ROM);

(iv) a set of structure coordinates defining the 10-angstrom radius structure defined in relation to Pro444 in human glucocerebrosidase mutant Leu444Pro (Table 18, enclosed CD-ROM);

(v) a set of structure coordinates defining the 10-angstrom radius structure defined in relation to Cys463 in human glucocerebrosidase mutant Arg463Cys (Table 20, enclosed CD-ROM); and (vi) a set of structure coordinates defining the 10-angstrom radius structure defined in relation to His496 in human glucocerebrosidase mutant Arg496His (Table 22, enclosed CD-ROM).

The amino acid residues forming the 10-angstrom radius structures of the human glucocerebrosidase mutants were identified as having the following amino acid residue coordinates according to the amino acid sequences of the mutant polypeptides:

(i) 76, 81, 285, 312, 314, 320, 324, 325, 336, 364-378, 423, and 433 for human glucocerebrosidase mutant Asn370Ser (SEQ ID NO: 2);

(ii) 244-247, and 390-397 for human glucocerebrosidase mutant Val394Leu (SEQ ID NO: 3);

(iii) 20, 21, 95-100, and 401-411 for human glucocerebrosidase mutant Asp409His (SEQ ID NO: 4);

(iv) 65-67, 440-447, 460-464, 468, and 469 for human glucocerebrosidase mutant Leu444Pro (SEQ ID NO: 5);

(v) 360-366, 443-446, 460-467, and 484-89 for human glucocerebrosidase mutant; Arg463Cys (SEQ ID NO: 6); and (vi) 33-35, 69, 71, 450-456, 474-478, and 493-497 for human glucocerebrosidase mutant Arg496His (SEQ ID NO: 7).

The relevant above-described structure coordinates were used to computationally generate models representing the predicted, essentially complete, structure of human glucocerebrosidase mutants Asn370Ser, Val394Leu, Asp409His, Leu444Pro, Arg463Cys, and Arg496His at 2.0 angstrom resolution.

The relevant above-described sets of structure coordinates were used to computationally generate models representing the predicted 10-angstrom radius structure defined in relation to mutant amino acid residues Ser370, Leu394, His409, Pro444, Cys463, and His496 in human glucocerebrosidase mutants Asn370Ser, Val394Leu, Asp409His, Leu444Pro, Arg463Cys, and Arg496His, respectively.

For comparison of the mutant 10-angstrom radius structures with corresponding structures of normal human glucocerebrosidase, the coordinates defining the structure of amino acid residues of the normal human glucocerebrosidase [(SEQ ID NO: 1), whose structure is defined by atom coordinates 1-3929 of Table 4 (enclosed CD-ROM)] having the same amino acid sequence position coordinates in the normal glucocerebrosidase polypeptide as those of the amino acid residues forming the mutant 10-angstrom radius structure in the mutant polypeptide were employed. Hence, the structures of the portions of the normal glucocerebrosidase corresponding to the 10-angstrom radius structures of the human glucocerebrosidase mutants Asn370Ser, Val394Leu, Asp409His, Leu444Pro, Arg463Cys, and Arg496His are defined by the sets of structure coordinates set forth in Tables 5-10 (enclosed CD-ROM), respectively.

Conclusion: The presently disclosed method enables for the first time generation of sets of structure coordinates defining with optimal accuracy essentially complete predicted 3D atomic structures of mutant human glucocerebrosidase molecules associated with Gaucher disease, in particular those of the most prevalent mutants Asn370Ser (SEQ ID NO: 2), Val394Leu (SEQ. ID NO: 3), Asp409His (SEQ ID NO: 4), Leu444Pro (SEQ ID NO: 5), Arg463Cys (SEQ ID NO: 6), and Arg496His (SEQ ID NO: 7). The presently-described sets of structure coordinates were used for generating for the first time essentially complete optimally accurate computer-generated models representing such 3D structures. Hence, by virtue of such capacity, the presently described computing platforms enable for the first time computational identification of compounds capable of correcting in-vivo, with optimal efficacy and safety, the impaired enzymatic activity of essentially any given mutant glucocerebrosidase molecule associated with Gaucher disease. Hence, the presently disclosed method enables identification of optimal Gaucher disease drugs.

Example 3

Partially Glycosylated Human Glucocerebrosidase has Greatly Increased Stability Under Physiological Conditions Relative to Fully Glycosylated Glucocerebrosidase, While Retaining Full Biological Functionality: Optimal Gaucher Disease Drug Background: As described above, whole enzyme replacement therapy using fully glycosylated human glucocerebrosidase, such as Cerezyme®, is currently the treatment of choice for treatment of Gaucher disease. Such treatment, however, is suboptimal since it does not satisfactorily alleviate the symptoms of the disease. Treatment of Gaucher disease with such a fully glycosylated glucocerebrosidase has the additional disadvantages of requiring administration with suboptimally high frequency, and of concomitantly being suboptimally expensive. One potential strategy to overcome these limitations would be to identify/design novel glucocerebrosidase molecules having enhanced stability under physiological conditions relative to fully glycosylated glucocerebrosidase, such as Cerezyme®, and having the capacity to undergo uptake by cells affected in Gaucher disease. By virtue of such enhanced stability under physiological conditions, such molecules would enable Gaucher disease treatment with optimal therapeutic efficacy, with an optimally mild dosing regimen, and thereby with optimal economy. While reducing the present invention to practice the present inventors generated a novel form of modified human glucocerebrosidase unexpectedly having such characteristics, as described below, thereby overcoming the limitations of the prior art.

Materials and Methods:

Partial deglycosylation of human glucocerebrosidase: Human glucocerebrosidase (Cerezyme®) was diluted in PBS to a concentration of 1.67 mg/ml, and dialyzed overnight against phosphate-buffered saline (PBS) so as to obtain the enzyme at a concentration of 0.9 to 1.2 mg/ml. Deglycosylation of the enzyme was performed by treatment with peptide-N-glycosidase F [PNGaseF; peptide-$N^4$-(acetyl-$\beta$-glucosaminyl) asparagine amidase] cloned from *Flavobacterium meningosepticum* and expressed in *E. coli*, EC 3.2.218; 3.5.1.52 (Roche Diagnostics GmbH, Mannheim, Germany). This enzyme cleaves all types of asparagine bound N-glycans (Chu, F. K., 1986. J Biol Chem. 261:172-7; Tarentino, A. L. et al., 1985. Biochemistry. 24:4665-71), as indicated in the reaction scheme shown in FIG. 5, but does not necessarily remove all glycan chains from native proteins. PNGaseF was added at a concentration of 50 units/ml of dialyzed glucocerebrosidase. Corresponding buffer (100 millimolar sodium phosphate, 25 millimolar EDTA, pH 7.2) was added to a control sample. Deglycosylation was allowed to proceed for 88 hours at 25 degrees centigrade, and was confirmed by either SDS-PAGE, or mass spectrometry analysis of the fully glycosylated and PNGaseF-treated glucocerebrosidase.

Glucocerebrosidase enzyme activity assay: Glucocerebrosidase activity was assayed in-vitro via a fluorescence assay using an artificial substrate, as previously described (refer to Meivar-Levy et al., 1994. Biochem J. 303:377-382), with modifications, using N-[6-[(7-nitrobenzo-2-oxa-1,3-diazol-4-yl)amino]hexanoyl]-D-erythro-glucosylsphingosine ($C_6$-NBD-GlcCer) as a substrate. $C_6$-NBD-GlcCer was obtained either from Avanti Polar Lipids, Inc. (Alabama, U.S.), or synthesized by N-acylation of glucosylsphingosine using succinimidyl 6-(7-nitrobenzo-2-oxa-1,3-diazol-4-yl) aminohexanoate, as previously described (Schwarzmann and Sandhoff, 1987. Methods Enzymol. 138:319-41). The dialyzed glucocerebrosidase (1:400 dilution, approximately 0.5-0.6 µg per reaction) was incubated with 1.5 nmol of $C_6$-NBD-GlcCer in a final volume of 200 µl of MES buffer (50 millimolar, pH 5.5). No other components were added to the reaction mixture. Reactions were allowed to proceed for 5 minutes at 37 degrees centigrade and stopped by addition of 2 ml of chloroform/methanol (1:2, v/v). Lipids were extracted according to the Bligh and Dyer procedure (Bligh and Dyer, 1959. Can. J. Biochem. Physiol. 37:911-917) and separated by thin layer chromatography (TLC) using chloroform/methanol/9.8 millimolar $CaCl_2$ (60:35:8, by volume) as the developing solvent. $C_6$-NBD-sphingolipids, the catalytic products of $C_6$-NBD-GlcCer, were identified using authentic standards as positive controls. $C_6$-NBD-fluorescence was quantified in the TLC plates using a Fluor-S Max fluorescent plate reader. In some cases, for quantification of C6-NBD fluorescence, lipids were recovered from TLC plates by scraping, followed by extraction, and NBD fluorescence ($\lambda$ex–468 nm, $\lambda$em=530 nm) was measured using a luminescence spectrometer (Perkin-Elmer Instruments, LS-5B).

Fluorescent glucocerebrosidase uptake assays: Fluorescent glucocerebrosidase was prepared by conjugating Cerezyme® with the fluorescent dye rhodamine, and used to perform cellular uptake assays in macrophages, as previously described for neurons (Pelled, D. et al., 2000. J. Inherit. Metab. Dis. 23:175-184).

Figure 6A:
Figure 6A:
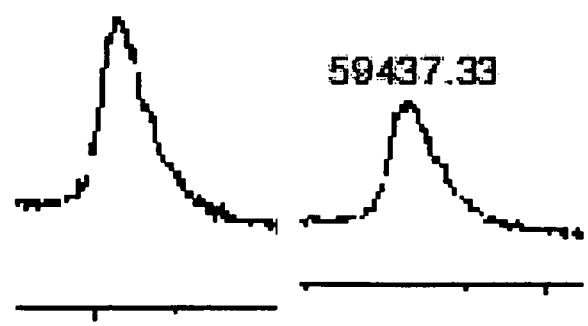

Experimental Results:

Treatment of 5 mg of glucocerebrosidase with 150 units of N-glycosidase F for 88 hours at 25 degrees centigrade resulted in generation of enzyme glycoforms displaying a reduction in molecular weight of between 1.5-2.5 kDa, as shown via SDS-PAGE analysis (FIG. 6a), and mass spectrometry analysis of the control and PNGaseF-treated enzyme (FIGS. 6b-c, respectively). Such reduction in molecular weight indicates that the glycosylation moiety of at least one N-linked glycosylation consensus sequences of the glucocerebrosidase polypeptide were removed by PNGaseF treatment. The glycosylation moiety was not removed from Asn19, the first N-linked glycosylation consensus sequences of the glucocerebrosidase polypeptide, by the treatment since the glycosylation moiety at this position following such treatment was detected in the crystal structure of the enzyme (Dvir, H. et al., 2003. EMBO Rep. 4:704-9). Glycosylation of Asn19 was previously shown to be required for full enzymatic activity (Berg-Fussman, A. et al., 1993. J. Biol. Chem. 268:14861-14866). Thus, PNGaseF treatment generated a glucocerebrosidase preparation in which substantially all glucocerebrosidase molecules are glycosylated at Asn19, and are deglycosylated at least one of amino acid residues Asn59, Asn146 and Asn270 Since the presently described partially glycosylated glucocerebrosidase preparation had never been reported, and hence functionally characterized, it was unclear at this stage whether the enzyme would be fully active and stable.

Figure 7:
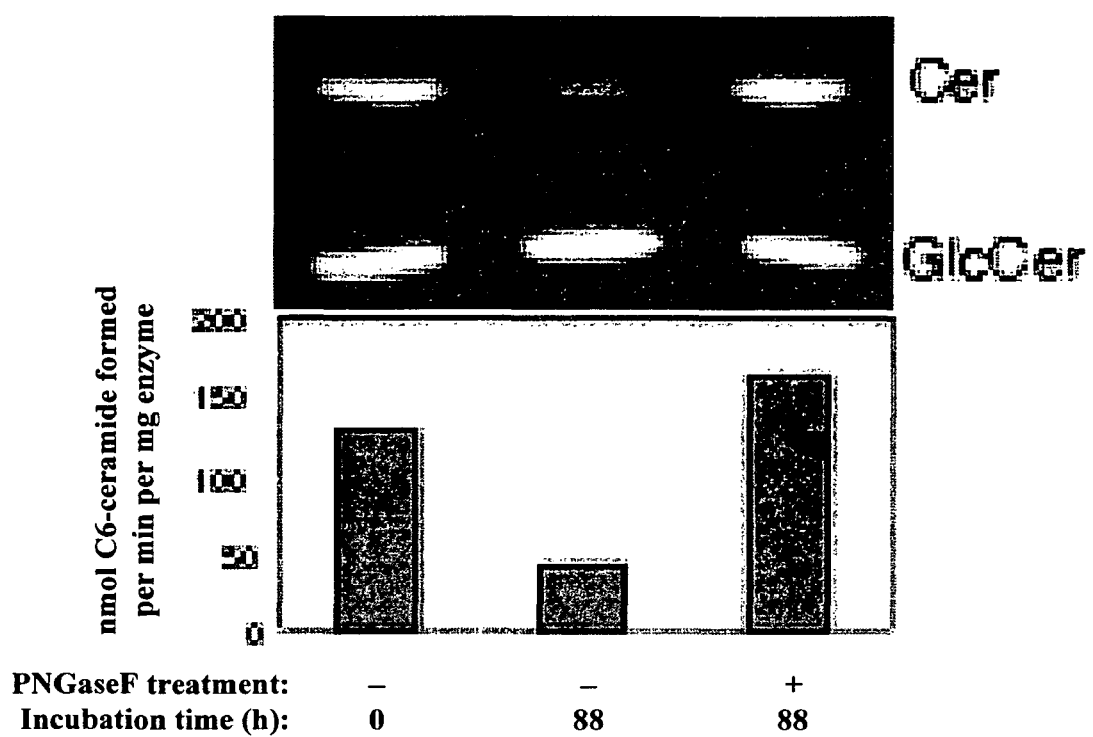
FIG. 7 depicts the highly enhanced stability of the partially glycosylated human glucocerebrosidase incubated for 40-64 hours under physiological conditions over that of the fully glycosylated enzyme. The top panel is a fluorescence photograph of a thin layer chromatography (TLC) assay used to measure enzymatic activity using a fluorescent GlcCer substrate (GlcCer) from which ceramide (Cer) is formed. The lower panel is a bar-graph, in which the bars depicting quantitation of the enzymatic activity measured in the assay. Enzymatic activity of the fully glycosylated and partially glycosylated enzyme was measured at time zero and after the 88-hour deglycosylation reaction (corresponding to a 40-64 hour incubation under physiological conditions). The enzymatic activity of the PNGaseF-treated enzyme at time zero (data not shown) was similar to that of the untreated enzyme. Note that the enzymatic activity of the partially glycosylated enzyme after the 40-64 hour incubation under physiological conditions remained unchanged, whereas the fully glycosylated enzyme lost about two-thirds of its activity.
Figure 8A:
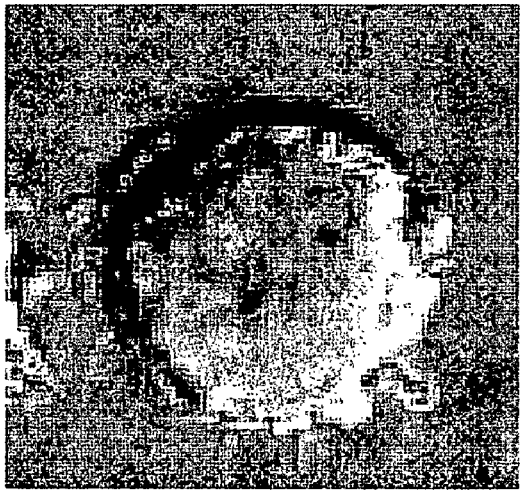
FIGS. 8a-d are photomicrographs depicting retention of capacity of partially glycosylated human glucocerebrosidase to undergo internalization by macrophages.
Figure 8B:
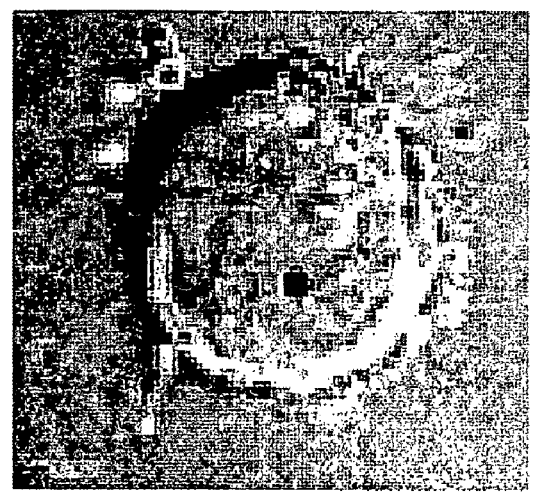
Figure 8C:
Figure 8D:

The enzymatic activity of the partially glycosylated enzyme was analyzed via a fluorescence enzymatic activity assay prior to, and following the 88-hour deglycosylation reaction in PBS described above. Since the partial deglycosylation of the glucocerebrosidase was found to be essentially complete after 24 to 48 hours of reaction time (data not shown), the 88-hour deglycosylation reaction corresponds to an incubation of the partially glycosylated glucocerebrosidase for 40-64 hours in PBS at 25 degrees centigrade. As shown in FIG. 7 and Table 23, after such a 40- to 64-hour incubation under physiological conditions, the partially glycosylated enzyme was quite unexpectedly and remarkably found to retain essentially all (93.5 percent) of its original enzymatic activity whereas by this time the fully glycosylated enzyme retained only about two-thirds (35.4 percent) of its original enzymatic activity. The fully and partially glycosylated forms of the enzyme displayed essentially identical enzymatic activity levels prior to incubation, and the enzymatic activity levels of the partially glycosylated enzyme displayed were unaffected by the dialysis. These experiments were performed with essentially identical results by incubation of the drug Cerezyme® in its liquid injection form (200 unit vial formulation: 212 units imiglucerase, 170 mg mannitol, 52 mg trisodium citrate, 18 mg disodium hydrogen citrate, 0.53 mg polysorbate 80, NF; data not shown). These results therefore surprisingly demonstrated that partially glycosylated human glucocerebrosidase is remarkably more enzymatically stable under physiological conditions than the fully glycosylated enzyme.

TABLE 23

Enzymatic activity assays of partially versus fully glycosylated human glucocerebrosidase.

| Batch | Activity (nmol/min/µg) | | | | | | | | | |
|---|---|---|---|---|---|---|---|---|---|---|
| | DG 5 | DG 6 | DG 7 | DG 8 | DG 9 | DG 10 | DG 11 | DG 12 | DG 8(2) | DG 13 |
| Before dialysis | 0.21 | 0.23 | 0.068 | 0.097 | 0.11 | 0.186 | 0.178 | | | |
| After dialysis | 0.19 | 0.32 | 0.058 | 0.067 | 0.05 | | 0.208 | | | |
| Control (untreated) at 88 hours | 0 | 0.19 | 0.019 | 0.016 | 0.003 | 0.059 | 0.053 | 0.07 | 0.17 | 0.13 |
| PNGaseF-treated at 88 hours | 0.081 | 0.33 | 0.053 | 0.059 | 0.058 | 0.139 | 0.247 | 0.104 | 0.24 | 0.21 |
| | Percent enzymatic activity compared to after deglycosylation | | | | | | | | | |
| Control | 0 | 59.4* | 32.8* | 23.9* | 0.06 | | 25.5* | | | |
| Deglycosylated | 42.6 | 103.1* | 91.4* | 60.8* | 116 | | 119* | | | |
| | Fold increase in enzymatic activity compared to control at 88 hours | | | | | | | | | |
| Deglycosylated | 81 | 1.73§ | 2.78§ | 3.69§ | 19.3 | 2.36§ | 4.66§ | 1.48§ | 1.41§ | 1.62§ |

| | Percent original enzymatic activity remaining at 88 hours | |
|---|---|---|
| | Average | SD |
| Control | 35.4 | 16.5 |
| Deglycosylated | 93.5 | 24.5 |

| Fold-increase in activity of deglycosylated enzyme compared to control enzyme at 88 hours | |
|---|---|
| Average | SD |
| 2.47 | 1.18 |

*data points used to generate "Percent enzymatic activity compared to after deglycosylation" figures
§data points used to generate "Food increase in enzymatic activity compared to control at 88 hours" figures In order to obtain Cerezyme®, the source human glucocerebrosidase employed in these experiments, the carbohydrate residues on glucocerebrosidase are subjected to sequential enzymatic modification using sialidase, beta-galactosidase and beta-N-acetylglucosaminidase so as to expose mannose residues which can be recognized by macrophages, allowing Cerezyme® to be internalized by macrophages (Genzyme. 2000. Product Monograph on Cerezyme®), the main cell type affected in Gaucher disease. Thus, since the carbohydrate residues of human glucocerebrosidase, in particular the terminal mannose residues of Cerezyme®, are essential for targeting the enzyme to macrophages, it was expected that removal of such moieties by PNGaseF would have a detrimental effect on the capacity of the enzyme to target to, and be internalized by, cells affected in Gaucher disease having mannose-specific receptors, such as macrophages. The ability of the partially glycosylated glucocerebrosidase to be internalized by cultured human macrophages was therefore examined by treating macrophages with the partially or fully glycosylated forms of the enzyme conjugated to rhodamine, and analyzing internalization of the fluorescent enzyme via fluorescence microscopy. Unexpectedly, as is shown in FIGS. 8a-d, the partially glycosylated glucocerebrosidase was found to retain the capacity to undergo very significant uptake by macrophages.

The presently disclosed results were highly unpredictable and unexpected for various reasons. It is well known to the ordinarily skilled artisan that deglycosylation of a glycoenzyme, such as glucocerebrosidase, can result in significant reduction of the stability of the enzyme (refer, for example, to: Khan R H. et al., 2003. J Biosci. 28:709-14; and Berg-Fussman, A. et al., 1993. J. Biol. Chem. 268:14861-14866). Moreover, these results were highly unexpected in light of PNGaseF-treated glucocerebrosidase, nor enhancement of glucocerebrosidase stability via deglycosylation having been reported, described or suggested in the art. The observed retention of full enzymatic activity was highly unexpected since, prior to the making of the present invention, it had been demonstrated that glycosylation of human glucocerebrosidase is essential for enzymatic activity (Grace, M. E., and G. A. Grabowski. 1990. Human acid beta-glucosidase: glycosylation is required for catalytic activity. Biochem Biophys Res Commun. 168:771-7; Berg-Fussman, A. et al., 1993. J. Biol. Chem. 268:14861-14866).

Conclusion: The presently described experimental results disclose the highly unexpected and surprising capacity of the partially glycosylated human glucocerebrosidase molecule of the present invention to display full enzymatic activity levels, to display much greater stability under physiological conditions than fully glycosylated human glucocerebrosidase, such as Cerezyme®, and to retain essentially full capacity to undergo internalization by cells affected by Gaucher disease, such as macrophages. By virtue of being fully enzymatically active, optimally stable and of being essentially fully internalizable by macrophages, the presently described partially glycosylated human glucocerebrosidase is far superior as a drug for enzyme replacement therapy of Gaucher disease than fully glycosylated human glucocerebrosidase, such as Cerezyme®, the state-of-the-art treatment for this disease. Enzyme replacement therapy using the presently disclosed partially glycosylated human glucocerebrosidase clearly represents the optimal treatment for Gaucher disease since the presently disclosed enzyme will display optimal in-vivo stability, and thereby optimal therapeutic effectiveness, relative to fully glycosylated human glucocerebrosidase, such as Cerezyme®. The optimal stability of the presently disclosed partially glycosylated enzyme under physiological conditions will moreover enable treatment of Gaucher disease by a significantly reduced dosing regimen, as well as significantly less expensive treatment of Gaucher disease than treatment regimens employing fully glycosylated human glucocerebrosidase, such as Cerezyme® which require suboptimally intensive dosing regimens and are suboptimally economical by virtue of the suboptimal stability of such an prior art enzyme under physiological conditions.

Example 4

Figure 9:
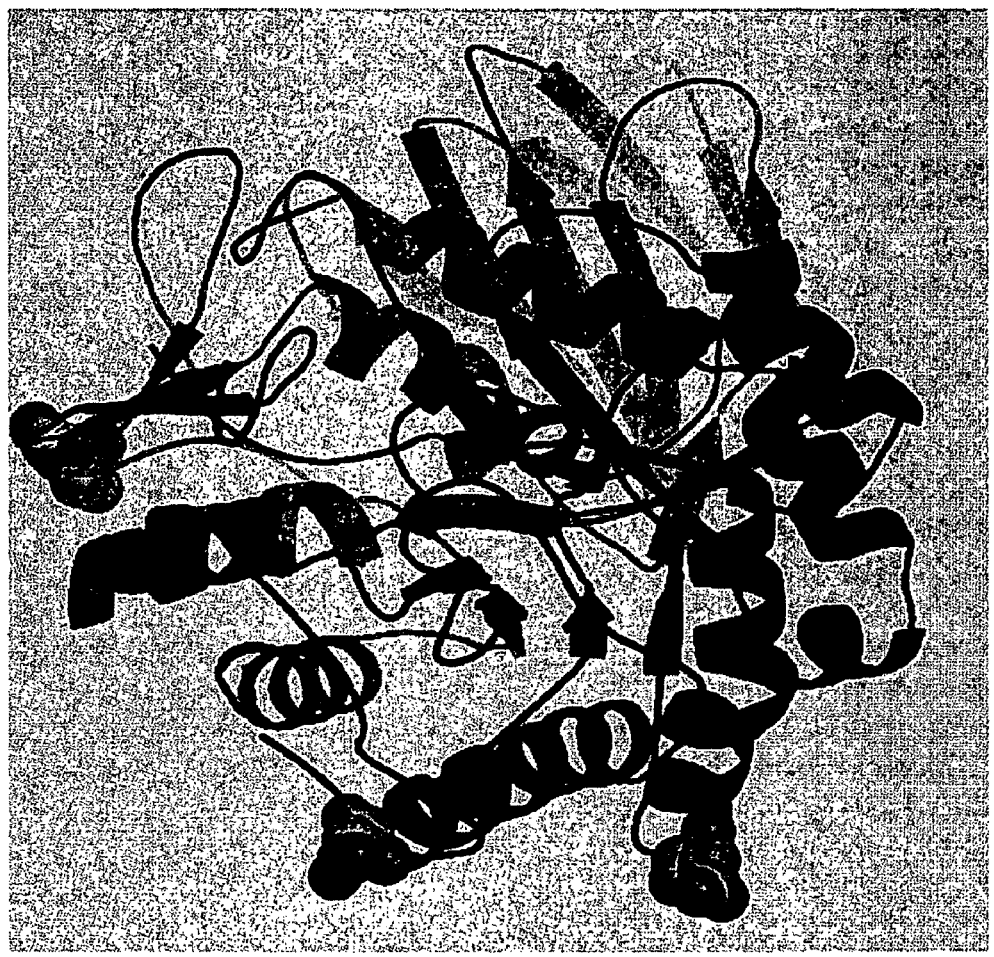
FIG. 9. is a 3-D structure diagram of crystallized human glucocerebrosidase treated with PNGaseF depicting that the PNGaseF treatment did not affect the structure of Asn19 (Dvir, H. et al., 2003. EMBO Rep. 4:704-9). The first, third and fourth glycosylation residues of human glucocerebrosidase, Asn19, Asn146 and Asn270 (shown as colored spheres), are shown to be exposed on the surface of the enzyme, as is the second glycosylation residue, Asn59, which cannot be seen in this figure.

Characterization of Partially Glycosylated Glucocerebrosidase Glycoforms Optimal for Gaucher Disease Treatment, and Determination of Optimal Conditions for Generation Thereof As described above, Cerezyme® is obtained by subjecting the carbohydrate residues of the molecule to sequential enzymatic modification so as to expose mannose residues which can be recognized by cells displaying mannose-specific receptors, such as macrophages, so as to allow internalization of Cerezyme® by such cells. Cerezyme® has five potential glycosylation sites, of which only four are actually glycosylated (Berg-Fussman, A. et al., 1993. J. Biol. Chem. 268: 14861-14866; Grace, M. E., and G. A. Grabowski. 1990. Biochem Biophys Res Commun. 168:771-7). Thus, human glucocerebrosidase glycosylated at these four sites is considered to be fully glycosylated. As described above, only glycosylation at Asn19, the first N-linked glycosylation residue of the glucocerebrosidase polypeptide, is apparently absolutely required for catalytic activity, and, as detected in the crystal structure, PNGaseF treatment does not affect the structure of Asn19 (Dvir, H. et al., 2003. EMBO Rep. 4:704-9). The second, third and fourth N-linked glycosylation residues of glucocerebrosidase, Asn59, Asn146 and Asn270, are all exposed on the surface of the enzyme (FIG. 9). These residues could not be detected in the crystal structure, and it is not known if this was due to lack of resolution in the respective areas of the crystal, or due to their removal by PNGaseF. Thus, studies are performed in order to identify which glycosidase moieties are removed by the above described PNGaseF treatment to generate partially glycosylated glucocerebrosidase glycoforms optimal for treatment of Gaucher disease, and the optimum conditions for generating such glycoforms are identified.

Materials and Methods:

The following deglycosylation reaction condition parameters are systematically manipulated to obtain partially glycosylated human glucocerebrosidase glycoforms with the highest stability and catalytic activity: ratio of glycosidase (e.g. PNGaseF) to glucocerebrosidase (e.g. Cerezyme®), reaction time, pH, and temperature. The change in molecular weight between fully glycosylated and PNGaseF-treated glucocerebrosidase is analyzed by mass spectrometry and by SDS-PAGE, and the PNGaseF-treated enzymes are analyzed for enzymatic activity using a radioactive or fluorescent analog of GlcCer, as previously described (Meivar-Levy, I. et al., 1994. Biochem. J. 303:377-382), and as described above.

Analyses are performed to identify which of the four carbohydrate chains have been removed by the glucocerebrosidase molecules deglycosylated under the different PNGaseF treatments. This is simply and conveniently analyzed since PNGaseF removes the whole glycosylation moiety attached to an Asn residue by cleaving the bond between the residue and the first sugar in the carbohydrate chain (N-acetylglucosamine; see FIG. 5). Tryptic digests of the partially and fully glycosylated glucocerebrosidase are prepared, and the identity of the cleaved carbohydrate moieties is determined by mass spectrometry. These analyses are performed in the Weizmann Institute Center for Biological Mass Spectrometry, a unit established with three state of the art mass spectrometers.

Results:

The glycosylation patterns of, and optimal reaction conditions for generating, partially glycosylated glucocerebrosidase glycoforms having optimal enzymatic activity and/or stability under physiological conditions are identified. Such partially glycosylated glucocerebrosidase glycoforms are therefore identified as potentially optimal Gaucher disease enzyme replacement therapy drugs.

Example 5

Comparison of the Ability of Partially Glycosylated Glucocerebrosidase to Reduce the Lipid (GlcCer) Storage Burden in Cells Affected in Gaucher Disease Compared to Fully Glycosylated Glucocerebrosidase Although, as described above, the presently disclosed partially glycosylated glucocerebrosidase is highly stable, active, and capable of undergoing essentially normal uptake by macrophages, the internalized enzyme must be capable of displaying the capacity to significantly reduce the GlcCer storage burden in affected cells of Gaucher disease patients in order to enable disease treatment. Therefore, the ability of partially glycosylated glucocerebrosidase to reduce the lipid (GlcCer) storage burden in macrophages compared to fully glycosylated glucocerebrosidase is analyzed.

Materials and Methods:

The extent and rate of uptake of partially glycosylated glucocerebrosidase (e.g. Cerezyme®) is examined by incubating macrophages, obtained from either healthy control individuals or from Gaucher disease patients (treated in the National Gaucher Clinic in Jerusalem under the supervision of Prof. Ari Zimran), with radioactive or fluorescent glucocerebrosidase. Fluorescent glucocerebrosidase is prepared by conjugating the enzyme with rhodamine, as described above, and radioactive glucocerebrosidase is prepared by iodination with $^{125}$I. The rate and extent of uptake of partially glycosylated glucocerebrosidase is compared with that of the fully glycosylated enzyme, and the internalization of both forms of the enzyme to lysosomes is analyzed using lysosomal markers.

The ability to reduce the storage burden of GlcCer in macrophages from Gaucher disease patients is measured by incubating the macrophages with fully or partially glycosylated glucocerebrosidase, and analyzing the resultant levels of GlcCer in these cells using two new techniques recently developed in the laboratory of the present inventors, as previously described (Bodennec, J. et al., 2003. J. Lipid. Res. 44:1413-1419; Bodennec, J. et al., 2003. 44:218-26). These techniques allow simple and reliable quantification of GlcCer levels in macrophages in the concentration range that it is found in these cells.

Results:

Partially glycosylated glucocerebrosidase is found to have a capacity to reduce the lipid (GlcCer) storage burden in macrophages from Gaucher disease patients so as to enable optimal disease treatment in such patients, thereby validating the presently disclosed partially glycosylated glucocerebrosidase as an optimal candidate drug for treatment of Gaucher disease.

Example 6

Industrial-Scale Production of Partially Glycosylated Glucocerebrosidase Drug for Optimal Treatment of Gaucher Disease Site-directed mutagenesis of the glycosylated Asn residues of partially glycosylated glucocerebrosidase (i.e. Asn59, Asn146 and/or Asn270) is used to generate a glucocerebrosidase having an optimal partial glycosylation pattern (see for instance, Berg-Fussman, A. et al., 1993. J. Biol. Chem. 268: 14861-14866) for use as a Gaucher disease drug. Replacement of Asn residues which are found to be deglycosylated by PNGaseF in forms of partially glycosylated glucocerebrosidase optimal for Gaucher disease treatment are replaced with non-glycosylated amino acid residues, thereby obviating the cumbersome requirement of employing enzymatic deglycosylation to generate such partially glycosylated glucocerebrosidase molecules. Additionally, site-directed mutagenesis is used to mutagenize Asn residues which are found to be glycosylated in partially glycosylated glucocerebrosidase glycoforms optimal for Gaucher disease treatment so as insert at such positions amino acid residues which obviate the need for glycosylation at such positions. This is exemplified by the previously described N19D substitution mutation (Berg-Fussman, A. et al., 1993. J. Biol. Chem. 268:14861-14866). Currently available methods for producing industrial quantities of fully glycosylated glucocerebrosidase (e.g. Cerezyme®) can then be employed to efficiently and reliably produce for therapeutic use industrial quantities of recombinant, mutagenized partially glycosylated glucocerebrosidase molecules optimal for treatment of Gaucher disease.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications, and sequences identified by their accession numbers mentioned in this specification are herein incorporated in their entirety by reference into the specification, to the same extent as if each individual publication, patent, patent application or sequence identified by its accession number was specifically and individually indicated to be incorporated herein by reference. In addition, citation or identification of any reference in this application shall not be construed as an admission that such reference is available as prior art to the present invention.

CD-ROM Content

The following CD-ROM is attached herewith:

Information provided as: File name/byte size/date of creation/operating system/machine format The material included in the CD ROM is hereby entirely incorporated into the specification by reference CD-ROM1 (19 files):

1. Table 4.txt/696,500 bytes/May 25, 2003/Microsoft Windows Word 2000/PC.
2. Table 5.txt/15,562 bytes/May 25, 2003/Microsoft Windows Word 2000/PC.
3. Table 6.txt/7,676 bytes/May 25, 2003/Microsoft Windows Word 2000/PC.
4. Table 7.txt/8,220 bytes/May 25, 2003/Microsoft Windows Word 2000/PC.
5. Table 8.txt/9,920 bytes/May 25, 2003/Microsoft Windows Word 2000/PC.
6. Table 9.txt/13,252 bytes/May 25, 2003/Microsoft Windows Word 2000/PC.
7. Table 10.txt/12,288 bytes/May 25, 2003/Microsoft Windows Word 2000/PC.
8. Table 11.txt/283,630 bytes/May 25, 2003/Microsoft Windows Word 2000/PC.
9. Table 12.txt/16,156 bytes/May 25, 2003/Microsoft Windows Word 2000/PC.
10. Table 13.txt/283,846 bytes/May 25, 2003/Microsoft Windows Word 2000/PC.
11. Table 14.txt/8,168 bytes/May 25, 2003/Microsoft Windows Word 2000/PC.
12. Table 15.txt/283,918 bytes/May 25, 2003/Microsoft Windows Word 2000/PC.
13. Table 16.txt/8,672 bytes/May 25, 2003/Microsoft Windows Word 2000/PC.
14. Table 17.txt/283,702 bytes/May 25, 2003/Microsoft Windows Word 2000/PC.
15. Table 18.txt/10,256 bytes/May 25, 2003/Microsoft Windows Word 2000/PC.
16. Table 19.txt/283,414 bytes/May 25, 2003/Microsoft Windows Word 2000/PC.
17. Table 20.txt/13,568 bytes/May 25, 2003/Microsoft Windows Word 2000/PC.
18. Table 21.txt/283,702 bytes/May 25, 2003/Microsoft Windows Word 2000/PC.
19. Table 22.txt/11,986 bytes/May 25, 2003/Microsoft Windows Word 2000/PC.

What is claimed is:

1. A composition-of-matter comprising a crystal of a glucocerebrosidase polypeptide, wherein the crystal has unit cell dimensions of a=about 107.7 angstroms, b=about 285.2 angstroms and c=about 91.8 angstroms and a crystal space group of $C222_1$, wherein the amino acid sequence of said glucocerebrosidase polypeptide consists of SEQ ID NO: 1, and wherein the amino acid sequence is glycosylated at Asn19 and unglycosylated at Asn59, Asn146 and Asn270 of SEQ ID NO:1.

2. The composition-of-matter of claim 1, wherein said crystal diffracts X-rays to a resolution of 2.9 angstroms or greater resolution.

* * * * *